United States Patent
Rajagopal et al.

(10) Patent No.: US 9,470,612 B2
(45) Date of Patent: Oct. 18, 2016

(54) SYSTEMS AND METHODS FOR DETECTING AN ANALYTE OF INTEREST IN A SAMPLE USING FILTERS AND MICROSTRUCTURED SURFACES

(75) Inventors: Raj Rajagopal, Woodbury, MN (US); Kurt J. Halverson, Lake Elmo, MN (US); Ramasubramani Kuduva Raman Thanumoorthy, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 267 days.

(21) Appl. No.: 14/122,373

(22) PCT Filed: Jun. 26, 2012

(86) PCT No.: PCT/US2012/044133
§ 371 (c)(1),
(2), (4) Date: Nov. 26, 2013

(87) PCT Pub. No.: WO2013/003309
PCT Pub. Date: Jan. 3, 2013

(65) Prior Publication Data
US 2014/0106397 A1 Apr. 17, 2014

Related U.S. Application Data

(60) Provisional application No. 61/503,356, filed on Jun. 30, 2011.

(51) Int. Cl.
*G01N 1/40* (2006.01)
*B01L 3/00* (2006.01)
(Continued)

(52) U.S. Cl.
CPC ........... *G01N 1/4077* (2013.01); *B01L 3/5021* (2013.01); *C12Q 1/04* (2013.01);
(Continued)

(58) Field of Classification Search
CPC ................... G01N 1/4077; G01N 2001/4083; G01N 2001/4088
See application file for complete search history.

(56) References Cited

U.S. PATENT DOCUMENTS

| | | | |
|---|---|---|---|
| 4,539,256 | A | 9/1985 | Shipman |
| 4,632,761 | A | 12/1986 | Bowers |

(Continued)

FOREIGN PATENT DOCUMENTS

| | | |
|---|---|---|
| CN | 102095626 | 6/2011 |
| EP | 0370238 | 5/1990 |

(Continued)

OTHER PUBLICATIONS

Ingham et al., "The micro-Petri dish, a million-well growth chip for the culture and high throughput screening of microorganisms", PNAS, Nov. 2007, vol. 104, No. 46, 18217-18222.

(Continued)

*Primary Examiner* — Paul West
(74) *Attorney, Agent, or Firm* — Qiang Han

(57) ABSTRACT

Systems and methods for detecting an analyte of interest in a sample. The system can include a first container comprising a filter portion. The filter portion can include a filter comprising a filtrand of the sample on a first side of the filter. The system can further include a second container comprising the filter portion coupled to a detection portion comprising a microstructured surface. The method can include providing the first container, coupling the filter portion to the detection portion to form the second container where the first side of the filter faces the microstructured surface, and centrifuging the second container toward the microstructured surface. The method can further include inverting the second container after centrifuging to decant the supernatant from the detection portion, such that a concentrate comprising a sediment of the sample is retained in the microstructured surface, which can be interrogated for an analyte of interest.

21 Claims, 26 Drawing Sheets

(51) Int. Cl.
*G01N 15/04* (2006.01)
*C12Q 1/04* (2006.01)

(52) U.S. Cl.
CPC ...... *G01N 15/042* (2013.01); *B01L 2300/042* (2013.01); *B01L 2300/047* (2013.01); *B01L 2300/069* (2013.01); *B01L 2300/0681* (2013.01); *B01L 2400/0409* (2013.01); *G01N 2001/4083* (2013.01); *G01N 2001/4088* (2013.01)

(56) References Cited

U.S. PATENT DOCUMENTS

| | | | |
|---|---|---|---|
| 4,698,311 | A | 10/1987 | Hall |
| 4,726,989 | A | 2/1988 | Mrozinski |
| 4,755,301 | A | 7/1988 | Bowers et al. |
| 4,867,881 | A | 9/1989 | Kinzer |
| 4,956,298 | A | 9/1990 | Diekmann |
| 4,959,301 | A | 9/1990 | Weaver |
| 5,120,594 | A | 6/1992 | Mrozinski |
| 5,234,667 | A | 8/1993 | Radtke |
| 5,260,360 | A | 11/1993 | Mrozinski |
| 5,620,662 | A | 4/1997 | Perlman |
| 5,716,798 | A | 2/1998 | Monthony |
| 5,770,440 | A | 6/1998 | Berndt |
| 5,820,767 | A | 10/1998 | Kane |
| 5,824,272 | A | 10/1998 | Uchida |
| 5,833,860 | A | 11/1998 | Kopaciewicz |
| 5,888,594 | A | 3/1999 | David |
| 6,143,247 | A | 11/2000 | Sheppard, Jr. |
| 6,197,579 | B1 | 3/2001 | Van Vlasselaer |
| 6,221,655 | B1 | 4/2001 | Fung |
| 6,386,699 | B1 | 5/2002 | Ylitalo |
| 6,391,578 | B2 | 5/2002 | Williams |
| 6,420,622 | B1 | 7/2002 | Johnston |
| 6,458,553 | B1 | 10/2002 | Colin |
| 6,566,508 | B2 | 5/2003 | Bentsen |
| 6,617,002 | B2 | 9/2003 | Wood |
| 6,627,159 | B1 | 9/2003 | Bedingham |
| 6,696,286 | B1 | 2/2004 | Halverson |
| 6,720,187 | B2 | 4/2004 | Bedingham |
| 6,730,397 | B2 | 5/2004 | Melancon |
| 6,734,401 | B2 | 5/2004 | Bedingham |
| 6,814,935 | B2 | 11/2004 | Harms |
| 6,867,342 | B2 | 3/2005 | Johnston |
| 6,869,666 | B2 | 3/2005 | Deeb |
| 6,987,253 | B2 | 1/2006 | Bedingham |
| 7,026,168 | B2 | 4/2006 | Bedingham |
| 7,164,107 | B2 | 1/2007 | Bedingham |
| 7,223,364 | B1 | 5/2007 | Johnston |
| 7,435,933 | B2 | 10/2008 | Bedingham |
| 7,445,752 | B2 | 11/2008 | Harms |
| 2001/0024805 | A1 | 9/2001 | Williams |
| 2002/0128578 | A1 | 9/2002 | Johnston |
| 2003/0036054 | A1 | 2/2003 | Ladisch |
| 2003/0235677 | A1 | 12/2003 | Hanschen |
| 2004/0038425 | A1 | 2/2004 | Ferguson |
| 2004/0058408 | A1 | 3/2004 | Thomas |
| 2004/0132208 | A1 | 7/2004 | Burshteyn |
| 2004/0179974 | A1 | 9/2004 | Bedingham |
| 2005/0079259 | A1* | 4/2005 | Gao .................... A23C 11/103 426/422 |
| 2006/0188396 | A1 | 8/2006 | Bedingham |
| 2006/0189000 | A1 | 8/2006 | Bedingham |
| 2006/0228811 | A1 | 10/2006 | Bedingham |
| 2006/0269451 | A1 | 11/2006 | Bedingham |
| 2007/0003441 | A1 | 1/2007 | Wohleb |
| 2007/0134784 | A1 | 6/2007 | Halverson |
| 2007/0151924 | A1 | 7/2007 | Mir |
| 2007/0196884 | A1 | 8/2007 | Bodini |
| 2010/0012589 | A1 | 1/2010 | Ribault et al. |
| 2010/0055790 | A1* | 3/2010 | Simon ................. C12M 23/08 435/383 |
| 2010/0297691 | A1 | 11/2010 | Ribeiro et al. |
| 2011/0039220 | A1 | 2/2011 | Zhou |
| 2011/0198282 | A1* | 8/2011 | Chu ................. B01D 39/1615 210/500.29 |

FOREIGN PATENT DOCUMENTS

| | | |
|---|---|---|
| FR | 2625691 | 7/1989 |
| JP | 2005-238158 | 9/2005 |
| WO | WO 00/57178 | 9/2000 |
| WO | WO 01/87486 | 11/2001 |
| WO | WO 02/00347 | 1/2002 |
| WO | WO 02/01180 | 1/2002 |
| WO | WO 02/01181 | 1/2002 |
| WO | WO 02/086454 | 10/2002 |
| WO | WO 02/090091 | 11/2002 |
| WO | WO 2004/000569 | 12/2003 |
| WO | WO 2004/013604 | 2/2004 |
| WO | WO 2004/058405 | 7/2004 |
| WO | WO 2005/108950 | 11/2005 |
| WO | WO 2007/070310 | 6/2007 |
| WO | WO 2007/137257 | 11/2007 |
| WO | WO 2010/071764 | 6/2010 |
| WO | WO 2010/078234 | 7/2010 |
| WO | WO 2010/080232 | 7/2010 |
| WO | WO 2010/080236 | 7/2010 |
| WO | WO 2011/063332 | 5/2011 |
| WO | WO 2011/152967 | 12/2011 |
| WO | WO 2011/153085 | 12/2011 |
| WO | WO 2011/156251 | 12/2011 |
| WO | WO 2011/156258 | 12/2011 |
| WO | WO 2013/003308 | 1/2013 |

OTHER PUBLICATIONS

Chilvers et al., "Synthesis and evaluation of novel fluorogenic substrates for the detection of bacterial β-galactosidase", Journal of Applied Microbiology,(2001), 91, 1118-1130.

Stettler et al. "New Disposable Tubes for Rapid and Precise Biomass Assessment for Suspension Cultures of Mammalian Cells". Biotechnology and Bioengineering 95:6, Dec. 20, 2006, pp. 1228-1233.

Standard Methods for the Examination of Water and Wastewater; Membrane Filter Technique for Members of the Coliform. American Public Health Association, American Water Works Association, Water Environment Federation. Washington DC (1999), 8 pages.

"Fast, reproducible and reliable determination of biomass in suspension cell cultures with VoluPAC tubes", Nature Methods Oct. 3, 2006, [retrieved from the internet on Oct. 20, 2008] URL www.nature.com/app_notes/nmeth/2006/061710/full/nmeth942.html, 7 pages.

International Search Report PCT/US2012/044133 Aug. 31, 2012, 3 pgs.

Wu, Guibiao, et al. "Effect of surfactant on sludge settling and dewaterability," China Water and Wastewater, Dec. 31, 2001, pp. 68-70, vol. 17, No. 1.

Garrido, L. B., et al., "Pressure Filtration and slip casting of mixed alumina-zircon suspensions," Journal of European Ceramic Society, Dec. 31, 2001, pp. 2259-2266.

Mu, Yizhou, et al., "Approach to Pre-Treatment Method of Heavy Metal Monitoring of Water Sample with High Sediment Concentration," Yellow River, Apr. 30, 2007, vol. 29, No. 4.

* cited by examiner

US 9,470,612 B2

SYSTEMS AND METHODS FOR DETECTING AN ANALYTE OF INTEREST IN A SAMPLE USING FILTERS AND MICROSTRUCTURED SURFACES

CROSS REFERENCE TO RELATED APPLICATIONS

This is a national stage filing under 35 U.S.C. 371 of PCT/US2012/044133, filed Jun. 26, 2012, which claims priority to Provisional Application No. 61/503,356, filed Jun. 30, 2011, the disclosure of which is incorporated herein by reference in its entirety.

FIELD

The present disclosure generally relates to methods for detecting an analyte of interest, such as bacteria, in a sample, and particularly, to rapid detection of an analyte of interest in a relatively large sample volume.

BACKGROUND

Testing aqueous samples for the presence of microorganisms (e.g., bacteria, viruses, fungi, spores, etc.) and/or other analytes of interest (e.g., toxins, allergens, hormones, etc.) can be important in a variety of applications, including food and water safety, infectious disease diagnostics, and environmental surveillance. For example, comestible samples, such as foods, beverages, and/or public water consumed by the general population may contain or acquire microorganisms or other analytes, which can flourish or grow as a function of the environment in which they are located. This growth may lead to the proliferation of pathogenic organisms, which may produce toxins or multiply to infective doses. By way of further example, a variety of analytical methods can be performed on samples of non-comestible samples (e.g., groundwater, urine, etc.) to determine if a sample contains a particular analyte. For example, groundwater can be tested for a microorganism or a chemical toxin; and urine can be tested for a variety of diagnostic indicators to enable a diagnosis (e.g., diabetes, pregnancy, etc.).

SUMMARY

Some aspects of the present disclosure provide a method for detecting an analyte of interest in a sample. The method can include providing a first container comprising a filter portion. The filter portion can include a filter configured to retain the analyte of interest from the sample, the filter having a first side and comprising a filtrand of the sample on the first side. The method can further include coupling the filter portion to a detection portion to form a second container. The detection portion can include a microstructured surface, and the filter portion and the detection portion can be coupled together such that the first side of the filter faces the microstructured surface of the detection portion. The method can further include centrifuging the second container toward the microstructured surface to move the filtrand from the filter to the microstructured surface of the detection portion to form a sediment and a supernatant of the sample. The method can further include inverting the second container, after centrifuging the second container, to decant at least a portion of the supernatant from the detection portion, such that a concentrate of the sample is retained in the microstructured surface of the detection portion of the second container, the concentrate comprising the sediment.

Some aspects of the present disclosure provide a method for detecting the presence of an analyte of interest in a sample. The method can include providing a first container comprising a receptacle portion adapted to contain the sample and a filter portion adapted to be removably coupled to the receptacle portion. The filter portion can include a filter configured to retain the analyte of interest from the sample, the filter having a first side. The method can include filtering the sample by moving the sample in a first direction from the receptacle portion toward the first side of the filter to form a filtrand of the sample on the first side of the filter, while removing a filtrate of the sample. The method can further include decoupling the receptacle portion and the filter portion of the first container, and coupling the filter portion to a detection portion to form a second container. The detection portion can include a microstructured surface, and the filter portion and the detection portion can be coupled together such that the first side of the filter faces the microstructured surface of the detection portion. The method can further include centrifuging the second container to move the filtrand in a second direction from the filter to the microstructured surface of the detection portion of the second container to form a sediment and a supernatant of the sample, the second direction being different from the first direction. The method can further include inverting the second container, after centrifuging the second container, to decant at least a portion of the supernatant of the sample from the detection portion, such that a concentrate of the sample is retained in the microstructured surface of the detection portion, the concentrate comprising the sediment. The method can further include interrogating the concentrate in the microstructured surface for the analyte of interest.

Some aspects of the present disclosure provide a system for detecting an analyte of interest in a sample. The system can include a first container comprising a filter portion. The filter portion can include a filter, the filter having a first side and comprising a filtrand of the sample on the first side. The system can further include a second container comprising the filter portion coupled to a detection portion. The detection portion can include a microstructured surface, and the filter portion and the detection portion can be coupled together such that the first side of the filter portion faces the microstructured surface of the detection portion. The microstructured surface of the detection portion can be adapted to receive a concentrate of the sample when the second container is exposed to a centrifugal force, and the microstructured surface of the detection portion can be further adapted to retain at least a portion of the concentrate of the sample under normal gravitational forces.

Some aspects of the present disclosure provide a system for detecting an analyte of interest in a sample. The system can include a first container comprising a receptacle portion adapted to contain the sample, and a filter portion. The filter portion can be adapted to be removably coupled to the receptacle portion and can include a filter, the filter having a first side and comprising a filtrand of the sample on the first side. The system can further include a second container comprising the filter portion coupled to a detection portion. The detection portion can include a microstructured surface, and the filter portion and the detection portion can be coupled together such that the first side of the filter portion faces the microstructured surface of the detection portion. The microstructured surface of the detection portion can be adapted to receive a concentrate of the sample when the second container is exposed to a centrifugal force, and the microstructured surface of the detection portion can be further adapted to retain at least a portion of the concentrate of the sample under normal gravitational forces.

Other features and aspects of the present disclosure will become apparent by consideration of the detailed description and accompanying drawings.

DETAILED DESCRIPTION

Figure 1:
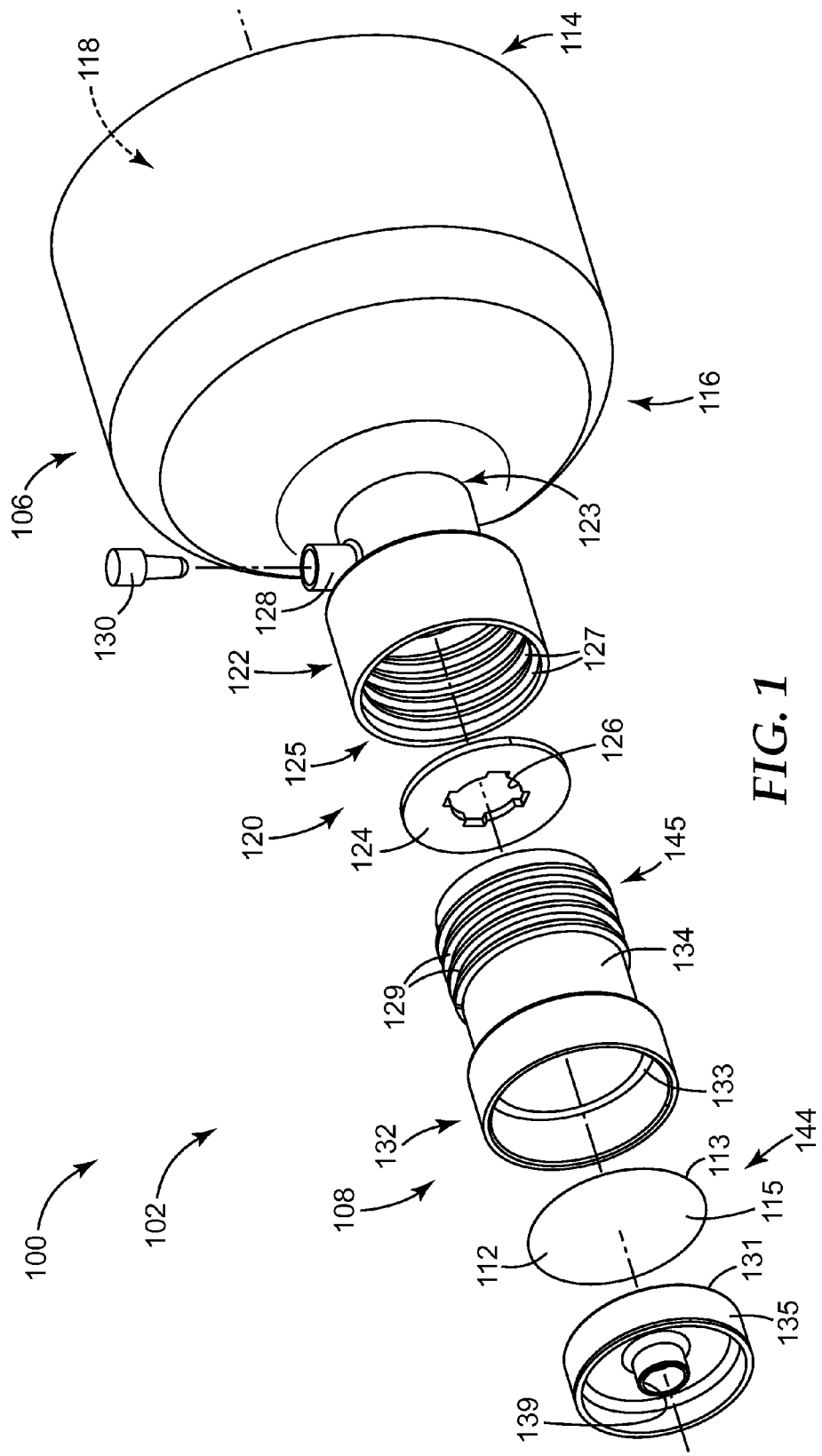
FIG. 1 is an exploded perspective view of a first container according to one embodiment of the present disclosure, the first container comprising a receptacle portion and a filter portion.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. It is to be understood that other embodiments may be utilized, and structural or logical changes may be made without departing from the scope of the present disclosure. Furthermore, terms such as "top," "bottom," and the like are only used to describe elements as they relate to one another, but need not recite specific orientations of the apparatus, to indicate or imply necessary or required orientations of the apparatus, or to specify how the invention described herein will be used, mounted, displayed, or positioned in use.

In a variety of samples that are desired to be tested for an analyte of interest, the analyte can be present in the sample at a low concentration, which can require that the sample be concentrated into a smaller volume in order to reach an appropriate concentration of an analyte of interest so as to achieve a detection threshold of an analytical technique.

In some existing systems and methods, centrifugation is used for samples having a high enough analyte concentration (e.g., bacterial concentration) to form a visible, packed "pellet" in the base of the centrifugation flask. The supernatant resulting from the centrifugation process can then be removed by decanting or aspiration. Visual inspection can be used in both decanting and aspiration to determine the appropriate volume of supernatant to be removed, and significant analyte loss can occur at the interface between the supernatant and the pellet. In addition, in samples having a particularly low concentration of the analyte of interest, the analyte may migrate to the base of the centrifugation flask during centrifugation but does not form a visible pellet and is not tightly packed. In such situations, the analyte can be easily dislodged during decanting or aspiration, which can decrease the overall collection efficiency of the analyte of interest, and can reduce the accuracy of the sample testing procedure.

As a result, in some existing systems and methods, filtration alone can be employed to concentrate low-concentration samples. While filtration can increase the concentration of the analyte of interest in the sample, retrieving the concentrated sample from the filter can be difficult and/or time-consuming. For example, in some situations, large elution volumes (e.g., 5-100 mL) can be required to backflush or wash the concentrated sample off of the filter, particularly for large initial sample volumes that may have required a filter having a large diameter. However, in the systems and methods of the present disclosure, even if such large volumes are required for elution, the eluted filtrand sample (i.e., the filtrand retained from filtering plus any diluents such as elution solutions) can be further concentrated by centrifuging into microstructures to achieve high-concentration, small-volume (e.g., on the order of nanoliters) aliquots of the sample for relatively faster detection of an analyte of interest.

In addition, in some existing systems and methods, portions of the sample can become irreversibly trapped in the filter during filtration. Trapping can be overcome using isoporous filters, however, filtration through isoporous filters can be slow, and the pores of the isoporous filter can be easily and rapidly plugged during filtration. However, the present inventors have discovered that certain filters allow for better recovery of the analyte of interest (e.g., of microorganisms, such as bacteria). For example, as described in greater detail below, "multi-zone" filter membranes (i.e., filters comprising multiple zones of porosity) can be particularly useful for recovering bacteria from the filter. This is because the porosity of the filter changes with its z dimension (i.e., depth). The present inventors discovered that by using such multi-zone filters and using the side of the filter having the smallest pore size as the "first side" of the filter (i.e., the side of the filter through which the sample passes first and on which the filtrand is collected), particular advantages in recovering the analyte of interest can be achieved.

However, as described above, even if such multi-zone filters are not used, the systems and methods of the present disclosure are still more effective than prior filtration-only systems and methods, because the systems and methods of the present disclosure further concentrate the eluted filtrand sample into a microstructured surface by centrifugation, for example, to improve the time-to-detect an analyte of interest.

The present disclosure generally relates to systems and methods for detecting the presence or absence of (and/or enumerating) an analyte of interest in a sample, particularly, in liquid samples, and more particularly, in dilute aqueous samples. Furthermore, the present disclosure generally relates to systems and methods for rapidly detecting the analyte. In some embodiments, the analyte is selected for detecting (e.g., the presence or absence of) *Escherichia coli* or other coliforms, for example, in a water sample. Detection of microorganisms (or other analytes) of interest in a water sample can be difficult, because of the low concentration of these microorganisms. As a result of the low concentration, detection in existing systems and methods can be very slow, because the microorganism(s) need to be grown (or the analyte concentration needs to be increased) to a detectable level, which can take time. The present inventors, however, have invented systems and methods for greatly decreasing the time needed to detect an analyte of interest in a water sample, and particularly, a dilute water sample.

Particularly, the present disclosure relates to systems and methods that employ a combination of filtration and centrifugation into microstructures in order to isolate and detect an analyte of interest from a sample, if present. For example, a large dilute aqueous sample can be filtered to retain the analyte(s) of interest, if present, by size, charge and/or affinity. The analyte(s) can be retain on a first side of a filter, which can then be oriented to face a microstructured surface during a subsequent centrifugation process. A diluent (e.g., nutrient media, or the like) can be added to the filter, and the analyte(s) can be forced into microstructured wells or recesses by centrifugation. In such embodiments, the filtrand on the filter plus any additional diluent that is added can form the "sample," and the sample can be sedimented (e.g., by centrifugation) into the microstructures, such that a concentrate of the sample (i.e., a portion of the sample having a higher concentration than the starting sample) can be retained in the microstructures, where the concentrate comprises a sediment of the sample (i.e., higher density matter), which would include the analyte(s), if present. The microstructures can then be interrogated to detect the analyte(s), either by detecting the presence/absence of the analyte(s), and/or by quantifying the analyte(s). Systems of the present disclosure can include container assemblies that are configured to facilitate the processes of filtering and centrifuging, as well as the transition between the filtration step and the centrifugation step. In addition, the systems and methods of the present disclosure allow for concentration of a large volume sample down to a very small volume, for example, from about 1 L down to about 1 nL (e.g., in one recess).

The present inventors have invented systems and methods for greatly decreasing the time needed to detect an analyte of interest in a sample, such as a water sample, and particularly, a dilute water sample. Particularly, the systems and methods of the present disclosure can include performing a first concentration step comprising filtering an original sample using a filter that is configured to retain one or more analyte(s) of interest to form a filtrand on one side of the filter; optionally adding a diluents to the filtrand and using the filtrand and any added diluents as the new or second sample; and performing a second concentration step comprising concentrating the second sample (e.g., based on density) into a microstructured surface comprising microstructured recesses or wells, wherein each microstructured recess can serve as an individual "test tube" of a small volume (e.g., on the scale of microliters or nanoliters), resulting in a high concentration of the analyte(s) of interest, if present, in the sample. This increase in concentration of the analyte(s) of interest can facilitate and expedite detection of the analyte(s), for example, for detecting the presence/absence of the analyte(s) and/or for enumerating the analyte(s) in a sample. The high-concentration, low-volume aliquots of the sample that are present in the microstructures can also facilitate enumerating the analyte(s) of interest.

In some embodiments, the analyte of interest can be a microorganism of interest itself, and in some embodiments, the analyte can be an indicator of a viable microorganism of interest. In some embodiments, the present disclosure can include systems and methods for determining the presence/absence of microorganism(s) of interest in a sample by interrogating the sample for analyte(s) of interest that are representative of the microorganism(s).

In some embodiments, rapid detection can refer to detection in no greater than 8 hours, in some embodiments, no greater than 6 hours, in some embodiments, no greater than 5 hours, in some embodiments, no greater than 4 hours, and in some embodiments, no greater than 3 hours. The detection time, however, can be dependent upon the type of analyte being detected because some microorganisms grow more quickly than others and will therefore reach a detectable threshold more rapidly. One of skill in the art will understand how to identify the appropriate assays (e.g., including the appropriate enzymes and enzymes substrates) to detect an analyte (e.g., microorganism) of interest. However, no matter which assay is used, or which analyte is selected, for a given analyte of interest, the systems and methods of the present disclosure will generally achieve a time-to-result more quickly than that achieved with standard culture techniques (e.g., growth-based detection in a microtiter plate (e.g., 96-well). That is, the systems and methods of the present disclosure can detect the analyte at least 25% faster than standard culture techniques (e.g., where each well contains 100 microliters of a sample), in some embodiments, at least 50% faster, in some embodiments, at least 75% faster, and in some embodiments, at least 90% faster.

Such samples to be analyzed for an analyte of interest can be obtained in a variety of ways. For example, in some embodiments, the sample to be analyzed itself is a liquid sample, such as a dilute liquid sample and/or a dilute aqueous sample. In some embodiments, the sample can include the liquid resulting from washing or rinsing a source of interest (e.g., a surface, fomite, etc.) with a diluent. In some embodiments, the sample can include the filtrate resulting from filtering or settling a liquid composition resulting from combining a source of interest with an appropriate diluent. That is, large insoluble matter and/or matter having a lower or higher density than the analyte(s) of interest, such as various foods, fomites, or the like, can be removed from a liquid composition in a first filtration or settling step to form the sample that will be analyzed using a method of the present disclosure.

The term "source" can be used to refer to a food or nonfood desired to be tested for analytes. The source can be a solid, a liquid, a semi-solid, a gelatinous material, and combinations thereof. In some embodiments, the source can be provided by a substrate (e.g., a swab or a wipe) that was used, for example, to collect the source from a surface of interest. In some embodiments, the liquid composition can include the substrate, which can be further broken apart (e.g., during an agitation or dissolution process) to enhance retrieval of the source and any analyte of interest. The surface of interest can include at least a portion of a variety of surfaces, including, but not limited to, walls (including doors), floors, ceilings, drains, refrigeration systems, ducts (e.g., airducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. All or a portion of the source can be used to obtain a sample that is to be analyzed using the methods of the present disclosure. For example, a "source" can be a water supply or water moving through a pipeline, and a relatively large volume sample can be taken from that source to form a sample that will be tested with the systems and methods of the present disclosure. Therefore, the "sample" can also be from any of the above-described sources.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, drinking water, other suitable comestible materials, and combinations thereof.

The term "nonfood" is generally used to refer to sources of interest that do not fall within the definition of "food" and are generally not considered to be comestible. Examples of nonfood sources can include, but are not limited to, clinical samples, cell lysates, whole blood or a portion thereof (e.g., serum), other bodily fluids or secretions (e.g., saliva, sweat, sebum, urine), feces, cells, tissues, organs, biopsies, plant materials, wood, soil, sediment, medicines, cosmetics, dietary supplements (e.g., ginseng capsules), pharmaceuticals, fomites, other suitable non-comestible materials, and combinations thereof.

The term "fomite" is generally used to refer to an inanimate object or substrate capable of carrying infectious organisms and/or transferring them. Fomites can include, but are not limited to, cloths, mop heads, towels, sponges, wipes, eating utensils, coins, paper money, cell phones, clothing (including shoes), doorknobs, feminine products, diapers, etc., portions thereof, and combinations thereof.

The term "analyte" is generally used to refer to a substance to be detected (e.g., by a laboratory or field test). A sample can be tested for the presence, quantity and/or viability of particular analytes. Such analytes can be present within a source (e.g., on the interior), or on the exterior (e.g., on the outer surface) of a source. Examples of analytes can include, but are not limited to, microorganisms, biomolecules, chemicals (e.g. pesticides, antibiotics), metal ions (e.g. mercury ions, heavy metal ions), metal-ion-containing complexes (e.g., complexes comprising metal ions and organic ligands), enzymes, coenzymes, enzyme substrates, indicator dyes, stains, adenosine triphophate (ATP), adenosine diphophate (ADP), adenylate kinase, luciferase, luciferin, and combinations thereof.

A variety of testing methods can be used to identify or quantitate an analyte of interest, including, but not limited to, microbiological assays, biochemical assays (e.g. immunoassay), or a combination thereof. In some embodiments, analytes of interest can be detected genetically; immunologically; colorimetrically; fluorimetrically; luminetrically; by detecting an enzyme released from a live cell in the sample; by detecting light that is indicative of the analyte of interest; by detecting light by absorbance, reflectance, fluorescence, or combinations thereof; or combinations thereof. That is, in some embodiments, interrogating the sample (or a concentrate of the sample) includes optically interrogating the sample, which can include any of the above-described types of optical interrogation, or any described below.

Specific examples of testing methods that can be used include, but are not limited to, antigen-antibody interactions, molecular sensors (affinity binding), thermal analysis, microscopy (e.g., light microscopy, fluorescent microscopy, immunofluorescent microscopy, scanning electron microscopy (SEM), transmission electron microscopy (TEM)), spectroscopy (e.g., mass spectroscopy, nuclear magnetic resonance (NMR) spectroscopy, Raman spectroscopy, infrared (IR) spectroscopy, x-ray spectroscopy, attenuated total reflectance spectroscopy, Fourier transform spectroscopy, gamma-ray spectroscopy, etc.), spectrophotometry (e.g., absorbance, reflectance, fluorescence, luminescence, calorimetric detection etc.), electrochemical analysis, genetic techniques (e.g., polymerase chain reaction (PCR), transcription mediated amplification (TMA), hybridization protection assay (HPA), DNA or RNA molecular recognition assays, etc.), adenosine triphosphate (ATP) detection assays, immunological assays (e.g., enzyme-linked immunosorbent assay (ELISA)), cytotoxicity assays, viral plaque assays, techniques for evaluating cytopathic effect, other suitable analyte testing methods, or a combination thereof.

The term "microorganism" is generally used to refer to any prokaryotic or eukaryotic microscopic organism, including without limitation, one or more of bacteria (e.g., motile or vegetative, Gram positive or Gram negative), viruses (e.g., Norovirus, Norwalk virus, Rotavirus, Adenovirus, DNA viruses, RNA viruses, enveloped, non-enveloped, human immunodeficiency virus (HIV), human Papillomavirus (HPV), etc.), bacterial spores or endospores, algae, fungi (e.g., yeast, filamentous fungi, fungal spores), prions, mycoplasmas, and protozoa. In some cases, the microorganisms of particular interest are those that are pathogenic, and the term "pathogen" is used to refer to any pathogenic microorganism. Examples of pathogens can include, but are not limited to, members of the family Enterobacteriaceae, or members of the family Micrococaceae, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., and *Corynebacterium* spp. Particular examples of pathogens can include, but are not limited to, *Escherichia coli* including enterohemorrhagic *E. coli* e.g., serotype O157:H7, O129:H11; *Pseudomonas aeruginosa; Bacillus cereus; Bacillus anthracia; Salmonella enteritidis; Salmonella enterica serotype Typhimurium; Listeria monocytogenes; Clostridium botulinum; Clostridium perfringens; Staphylococcus aureus*; methicillin-resistant *Staphylococcus aureus; Campylobacter jejuni; Yersinia enterocolitica; Vibrio vulnificus; Clostridium difficile*; vancomycin-resistant *Enterococcus; Enterobacter [Cronobacter] sakazakiil*; and coliforms. Environmental factors that may affect the growth of a microorganism can include the presence or absence of nutrients, pH, moisture content, oxidation-reduction potential, antimicrobial compounds, temperature, atmospheric gas composition and biological structures or barriers.

The term "biomolecule" is generally used to refer to a molecule, or a derivative thereof, that occurs in or is formed by an organism. For example, a biomolecule can include, but is not limited to, at least one of an amino acid, a nucleic acid, a polypeptide, a protein, a polynucleotide, a lipid, a phospholipid, a saccharide, a polysaccharide, and combinations thereof. Specific examples of biomolecules can include, but are not limited to, a metabolite (e.g., staphylococcal enterotoxin), an allergen (e.g., peanut allergen(s), egg allergen(s), pollens, dust mites, molds, danders, or proteins inherent therein, etc.), a hormone, a toxin (e.g., *Bacillus* diarrheal toxin, aflatoxin, *Clostridium difficile* toxin etc.), RNA (e.g., mRNA, total RNA, tRNA, etc.), DNA (e.g., plasmid DNA, plant DNA, etc.), a tagged protein, an antibody, an antigen, ATP, and combinations thereof.

The terms "soluble matter" and "insoluble matter" are generally used to refer to matter that is relatively soluble or insoluble in a given medium, under certain conditions. Specifically, under a given set of conditions, "soluble matter" is matter that goes into solution and can be dissolved in the solvent (e.g., diluent) of a system. "Insoluble matter" is matter that, under a given set of conditions, does not go into solution and is not dissolved in the solvent of a system. A source, or a sample taken from that source, can include soluble matter and insoluble matter (e.g., cell debris). Insoluble matter is sometimes referred to as particulate(s), precipitate(s), or debris and can include portions of the source material itself (i.e., from internal portions or external portions (e.g., the outer surface) of the source) or other source residue or debris resulting from an agitation process. In addition, a liquid composition comprising the source and a diluent can include more dense matter (i.e., matter having a higher density than the diluent and other matter in the mixture) and less dense matter (i.e., matter having a lower density than the diluent and other matter in the mixture). As a result, a diluent of the sample can be selected, such that the analyte(s) of interest is(are) more dense than the diluent and can be concentrated via settling (e.g., centrifugation).

The term "diluent" is generally used to refer to a liquid added to a source material to disperse, dissolve, suspend, emulsify, wash and/or rinse the source. A diluent can be used in forming a liquid composition, from which a sample to be analyzed using the methods of the present disclosure can be obtained. In some embodiments, the diluent is a sterile liquid. In some embodiments, the diluent can include a variety of additives, including, but not limited to, surfactants, or other suitable additives that aid in dispersing, dissolving, suspending or emulsifying the source for subsequent analyte testing; rheological agents; antimicrobial neutralizers (e.g., that neutralize preservatives or other antimicrobial agents); enrichment or growth medium comprising nutrients (e.g., that promote selective growth of desired microorganism(s)) and/or growth inhibitors (e.g., that inhibit the growth of undesired microorganism(s)); pH buffering agents; enzymes; indicator molecules (e.g. pH or oxidation/reduction indicators); spore germinants; an agent to neutralize sanitizers (e.g., sodium thiosulfate neutralization of chlorine); an agent intended to promote bacterial resuscitation (e.g., sodium pyruvate); stabilizing agents (e.g., that stabilize the analyte(s) of interest, including solutes, such as sodium chloride, sucrose, etc.); or a combination thereof. In some embodiments, the diluent can include sterile water (e.g., sterile double-distilled water (ddH$_2$O)); one or more organic solvents to selectively dissolve, disperse, suspend, or emulsify the source; aqueous organic solvents, or a combination thereof. In some embodiments, the diluent is a sterile buffered solution (e.g., Butterfield's Buffer, available from Edge Biological, Memphis Tenn.). In some embodiments, the diluent is a selective or semi-selective nutrient formulation, such that the diluent may be used in the selective or semi-selective growth of the desired analyte(s) (e.g., bacteria). In such embodiments, the diluent can be incubated with a source for a period of time (e.g., at a specific temperature) to promote such growth and/or development of the desired analyte(s).

Examples of growth medium can include, but are not limited to, Tryptic Soy Broth (TSB), Buffered Peptone Water (BPW), Universal Pre-enrichment Broth (UPB), *Listeria* Enrichment Broth (LEB), Lactose Broth, Bolton broth, or other general, non-selective, or mildly selective media known to those of ordinary skill in the art. The growth medium can include nutrients that support the growth of more than one desired microorganism (i.e., analyte of interest).

Examples of growth inhibitors can include, but are not limited to, bile salts, sodium deoxycholate, sodium selenite, sodium thiosulfate, sodium nitrate, lithium chloride, potassium tellurite, sodium tetrathionate, sodium sulphacetamide, mandelic acid, selenite cysteine tetrathionate, sulphamethazine, brilliant green, malachite green oxalate, crystal violet, Tergitol 4, sulphadiazine, amikacin, aztreonam, naladixic acid, acriflavine, polymyxin B, novobiocin, alafosfalin, organic and mineral acids, bacteriophages, dichloran rose bengal, chloramphenicol, chlortetracycline, certain concentrations of sodium chloride, sucrose and other solutes, and combinations thereof.

The term "agitate" and derivatives thereof is generally used to describe the process of giving motion to a liquid composition, for example, to mix or blend the contents of such liquid composition. A variety of agitation methods can be used, including, but not limited to, manual shaking, mechanical shaking, ultrasonic vibration, vortex stirring, manual stirring, mechanical stirring (e.g., by a mechanical propeller, a magnetic stirbar, or another agitating aid, such as ball bearings), manual beating, mechanical beating, blending, kneading, and combinations thereof.

The term "filtering" is generally used to refer to the process of separating matter by size, charge and/or function. For example, filtering can include separating soluble matter and a solvent (e.g., diluent) from insoluble matter, or filtering can include separating soluble matter, a solvent and relatively small insoluble matter from relatively large insoluble matter. As a result, a liquid composition can be "pre-filtered" to obtain a sample that is to be analyzed using the methods of the present disclosure. A variety of filtration methods can be used, including, but not limited to, passing the liquid composition (e.g., comprising a source of interest, from which a sample to concentrated can be obtained) through a filter, other suitable filtration methods, and combinations thereof.

"Settling" is generally used to refer to the process of separating matter by density, for example, by allowing the more dense matter in the liquid composition (i.e., the matter having a higher density than the diluent and other matter in the mixture) to settle or sink and/or by allowing the less dense matter in the liquid composition (i.e., the matter having a lower density than the diluent and other matter in the mixture) to rise or float. Settling may occur by gravity or by centrifugation. The more dense matter can then be separated from the less dense matter (and diluent) by aspirating the less dense (i.e., unsettled or floating) and diluent from the more dense matter, decanting the less dense matter and diluent, or a combination thereof. Pre-settling steps can be used in addition to or in lieu of pre-filtering steps to obtain a sample that is to be concentrated using the sample detection systems and methods of the present disclosure.

A "filter" is generally used to describe a device used to separate the soluble matter (or soluble matter and relatively small insoluble matter) and solvent from the insoluble matter (or relatively large insoluble matter) in a liquid composition and/or to filter a sample during sample concentration. Examples of filters can include, but are not limited to, a woven or non-woven mesh (e.g., a wire mesh, a cloth mesh, a plastic mesh, etc.), a woven or non-woven polymeric web (e.g., comprising polymeric fibers laid down in a uniform or nonuniform process, which can be calendered), a surface filter, a depth filter, a membrane (e.g., a ceramic membrane (e.g., ceramic aluminum oxide membrane filters available under the trade designation ANOPORE from Whatman Inc., Florham Park, N.J.), a polycarbonate membrane (e.g., track-etched polycarbonate membrane filters available under the trade designation NUCLEOPORE from Whatman, Inc.)), a polyester membrane (e.g., comprising track-etched polyester, etc.), a sieve, glass wool, a frit, filter paper, foam, etc., and combinations thereof.

In some embodiments, the filter can be configured to separate a microorganism of interest from a sample, for example, by size, charge, and/or affinity. For example, in some embodiments, the filter can be configured to retain a microorganism of interest, such that a filtrand retained on the filter comprises the microorganism of interest.

In some embodiments, the filter can be configured to retain at least 30% of the analyte(s) of interest in a sample (e.g., microorganisms of interest), in some embodiments, at least 50%, in some embodiments, at least 80%, in some embodiments, at least 85%, in some embodiments, at least 90%, and in some embodiments, at least 95%.

Additional examples of suitable filters are described in co-pending PCT Publication No. WO2011/156251 (Rajagopal, et al.), which claims priority to U.S. Patent Application No. 61/352,229; PCT Publication No. WO2011/156258 (Mach et al.), which claims priority to U.S. Patent Application No. 61/352,205; PCT Publication No. WO2011/152967 (Zhou), which claims priority to US Patent Application Nos. 61/350,147 and 61/351,441; and PCT Publication No. WO2011/153085 (Zhou), which claims priority to US Patent Application Nos. 61/350,154 and 61/351,447, all of which are incorporated herein by reference in their entirety.

In some embodiments, the term "filtrate" is generally used to describe the liquid remaining after the insoluble matter (or at least the relatively large insoluble matter) has been separated or removed from a liquid composition. In some embodiments, the term "supernatant" is generally used to describe the liquid remaining after the more dense matter has been separated or removed from a liquid composition. Such a filtrate and/or supernatant can form a sample to be used in the present disclosure. In some embodiments, the filtrate and/or supernatant can be incubated for a period of time to grow a microorganism of interest, and the resulting incubated filtrate and/or supernatant can form a sample to be used in the present disclosure. In some embodiments, growth media can be added to aid in growing the microorganism of interest.

In some embodiments, the term "filtrand" is generally used to describe the solid remaining after a liquid source (e.g., water to be tested) has been filtered to separate insoluble matter from soluble matter. Such a filtrand can be further diluted, and optionally agitated, grown (e.g., by adding growth media), and/or incubated, to form a sample to be used in the present disclosure. The filtrand may be present on one surface or side of the filter, and/or may have penetrated at least partially into the depth of the filter. As a result, in some embodiments, a diluent comprising an elution solution, a wash solution, or the like can be used to facilitate removing the filtrand from the filter. In some embodiments, surface filters can be preferred (e.g., over depth filters) for facilitating and enhancing removal of the filtrand from the filter.

In some embodiments, the g-force exerted on the filtrand in the subsequent centrifugation step can aid in removing the filtrand from the filter. In some cases, the retained analyte(s) of interest (e.g., microorganisms) can be eluted from the filter by repositioning the filter so that the force of gravity causes the retained biological organisms to dislodge and thereby elute from the filter. In other cases, retained analyte(s) may be eluted from the filter by manually shaking the filter to dislodge the retained analyte(s) from the filter. In other cases, retained analyte(s) may be eluted by vortexing the filter to dislodge the retained analyte(s) from the filter. In other cases, analyte(s) may be eluted from the filter by foam elution.

In some embodiments in which the analyte(s) of interest (e.g., microorganisms) are detected and/or quantified following recovery from the filter, methods of the present disclosure can include eluting at least 50% of the retained analyte(s) of interest from the filter, although the method may be performed after eluting less than 50% of the retained analyte(s) from the filter. In some embodiments, at least 60% of the retained analyte(s) can be eluted from the filter, in some embodiments, at least 70%, in some embodiments, at least 75%, in some embodiments, at least 80%, in some embodiments, at least 90%, and in some embodiments, at least 95%.

In some embodiments, no matter what form the starting sample is in, or how it was obtained, the sample can be agitated, grown (e.g., by adding growth media), and/or incubated, to form a sample to be analyzed by systems and methods of the present disclosure. In some embodiments, various reagents can be added at various stages of the process, including, but not limited to being added to the original sample, being added to the filtrand (e.g., with a diluent) or supernatant used to form the sample to be tested, being coated and/or dried in microstructured recesses that will serve as the detection vessels for a concentrate of the sample, or combinations thereof.

In some embodiments, the term "sediment" is generally used to describe the "pellet" or solid that is separated from the supernatant after the more dense matter has been separated or removed from a liquid composition, for example via centrifugation.

The term "microstructure" or "microstructured feature," and derivatives thereof, is generally used to refer to a structure or a feature having a structure that is a recognizable geometric shape that either protrudes (e.g., a wall) or is depressed (e.g., a well defined at least partially by the wall). For example, a microstructure can include a microstructured well formed to retain a liquid, a solid, a semi-solid, a gelatinous material, another suitable material, or a combination thereof. A microstructure can also include a wall or a base that at least partially defines a microstructured well. Furthermore, a microstructure can include a protrusion, a recess, or the like that is present on any of the above-described microstructures. For example, a microstructured well or wall can be textured, and such textures can also be referred to as microstructures.

In some embodiments, "microstructured" can refer to features that are no greater than 1000 micrometers in at least two of the possible dimensions, in some embodiments, no greater than 500 micrometers, and in some embodiments, no greater than 200 micrometers. However, in some embodiments of the present disclosure, "microstructured features" can be any features that are sufficient to retain a portion of a sample (e.g., a liquid concentrate of a sample after centrifugation toward a microstructured surface comprising the microstructured features) under normal gravitational forces, at any orientation. Therefore, the microstructured features of the present disclosure can have a sufficient depth (e.g., z dimension), or ratio (i.e., "aspect ratio") of a z dimension to an x-y dimension (or vice versa), that provides sufficient capillary force to retain a sample (e.g., a concentrated liquid comprising a sediment of a sample) of a given surface tension. The surface energy of the microstructured feature can be controlled (e.g., modified with a surface treatment) to enhance retention, however, generally, microstructured features of the present disclosure, such as wells, recesses or depressions, can have an aspect ratio that provides the necessary capillary forces to retain a sample of interest.

In some embodiments, the aspect ratio can be at least about 0.1, in some embodiments, at least about 0.25, in some embodiments, at least about 0.5, in some embodiments, at least about 1, in some embodiments, at least about 2, in some embodiments, at least about 5, and in some embodiments, at least about 10. Because, in some embodiments, the x-y dimension of a microstructured feature (e.g., a recess) can change along its depth or z dimension (e.g., if the feature includes a draft angle), the aspect ratio can be the ratio of a z dimension to a "representative" x-y dimension. The representative x-y dimension can be a top dimension (i.e., the x-y dimension at the opening of a recess), a bottom dimension (e.g., the x-y dimension at the base of a recess), a middle dimension (e.g., the x-y dimension at the half-depth position), an average x-y dimension (e.g., averaged along the depth), another suitable representative dimension, or the like.

The term "microstructured surface" is generally used to refer to a surface that comprises microstructures or microstructured features.

The term "microreplicate" and derivatives thereof, is generally used to refer to the production of a microstructured surface through a process where positive structured surface features are formed in a tool (e.g., as posts, pins, protrusion, or the like) that is used to form negative features (e.g., recesses, wells, depressions, or the like) in a material.

The term "primary," when used with reference to a microstructure, is generally used to refer to a microstructure having the largest scale of any microstructure on the same surface.

The term "secondary," when used with reference to a microstructure, is generally used to refer to a microstructure having a smaller scale microstructure relative to one or more primary microstructures on the same surface.

The phase "substantially transparent" is generally used to refer to a body or substrate that transmits at least 50% of electromagnetic radiation having wavelengths at a selected wavelength or within a selected range of wavelengths in the ultraviolet to infrared spectrum (e.g., from about 200 nm to about 1400 nm; "UV-IR"), in some embodiments, at least about 75% of a selected wavelength (or range) in the UV-IR spectrum, and in some embodiments, at least about 90% of a selected wavelength (or range) in the UV-IR spectrum.

The phrase "substantially non-transparent" is generally used to refer to a body or substrate that transmits less than 50% of electromagnetic radiation having wavelengths at a selected wavelength or within a selected range of wavelengths in the ultraviolet to infrared spectrum (e.g., from about 200 nm to about 1400 nm; "UV-IR"), in some embodiments, less than 25% of a selected wavelength (or range) in the UV-IR spectrum, and in some embodiments, less than 10% of a selected wavelength (or range) in the UV-IR spectrum.

Various details of "substantially transparent" and "substantially non-transparent" materials are described in PCT Patent Publication No. WO 2011/063332, which is incorporated herein by reference in its entirety.

The terms "hydrophobic" and "hydrophilic" are generally used as commonly understood in the art. Thus, a "hydrophobic" material has relatively little or no affinity for water or aqueous media, while a "hydrophilic" material has relatively strong affinity for water or aqueous media. The required levels of hydrophobicity or hydrophilicity may vary depending on the nature of the sample, but may be readily adjusted based on simple empirical observations of a liquid sample when applied to various hydrophobic or hydrophilic surfaces.

In some embodiments, contact angle measurements (e.g., static and/or dynamic) can be used to characterize the hydrophobicity/hydrophilicity of a surface. Such surface characteristic may be attributable to the material makeup of the surface itself, which can be independent of the bulk material. That is, in some embodiments, even if the bulk material forming a structure is largely hydrophobic, the surface that will contact a sample can be modified to be hydrophilic so that aqueous samples, for example, will have a greater affinity for the modified surface. Exemplary static and dynamic contact angle measurement methods are described in Examples 12 and 13.

In some embodiments, the static water surface contact angle of the material from which the microstructured surface of the present disclosure is formed (e.g., which can be measured on the structured surface, or on a smooth unstructured surface of the same material) can be at least about 50 degrees, in some embodiments, at least about 65 degrees, in some embodiments, at least about 75 degrees, in some embodiments, at least about 85 degrees, in some embodiments, at least about 95 degrees, in some embodiments, at least about 100 degrees, and in some embodiments, at least about 130 degrees.

In some embodiments, the dynamic advancing surface contact angle of the material from which the microstructured surface of the present disclosure is formed (e.g., which can be measured on the structured surface, or on a smooth unstructured surface of the same material) can be at least about 50 degrees, in some embodiments, at least about 65 degrees, in some embodiments, at least about 75 degrees, in some embodiments, at least about 85 degrees, in some embodiments, at least about 95 degrees, in some embodiments, at least about 100 degrees, and in some embodiments, at least about 130 degrees.

In some embodiments, the dynamic receding surface contact angle of the material from which the microstructured surface of the present disclosure is formed (e.g., which can be measured on the structured surface, or on a smooth unstructured surface of the same material) can be at least about 25 degrees, in some embodiments, at least about 35 degrees, in some embodiments, at least about 45 degrees, in some embodiments, at least about 65 degrees, in some embodiments, at least about 75 degrees, in some embodiments, at least about 90 degrees, and in some embodiments, at least about 100 degrees.

FIGS. 1-3 and 4-6 illustrate a sample detection system 100 according to one embodiment of the present disclosure. The sample detection system 100 can include a first container (or "first container assembly") 102 (see FIGS. 1, 2 and 5) and a second container (or "second container assembly") 104 (see FIGS. 3, 4 and 5). In some embodiments, the sample detection system 100 can be used to concentrate a sample to form a concentrate (e.g., in microstructured recesses 136, as described below), and can be further used to interrogate the concentrate for an analyte of interest, that is, for detecting the presence or absence of an analyte of interest.

Various details and features of detection systems and methods that employ centrifugation as a means to concentrate a sample into microstructured volumes for detection are described in co-pending U.S. Patent Application No. 61/503, 328, filed on Jun. 30, 2011, which is incorporated herein by reference in its entirety.

Various details and features of concentration systems and methods for increasing the concentration of a dilute sample via a first centrifugation step and then pelleting the resulting concentrate via a second centrifugation step are described in PCT Application Publication No. WO2010/080232 (Halverson), which claims priority to U.S. Patent Application No. 61/139,144, both of which are incorporated herein by reference in their entirety. Other systems and methods for increasing the concentration of a dilute sample using an upfront filtration process are described in PCT Application Publication No. WO2010/080236 (Halverson), which claims priority to U.S. Patent Application No. 61/139,158, both of which are incorporated herein by reference in their entirety.

In some embodiments, the sample detection system 100 can be used to determine the presence or absence of a microorganism of interest in a sample by interrogating the sample for the microorganism itself, or for an analyte of interest that is representative of the presence of the microorganism. For example, in some embodiments, the microorganisms themselves can be concentrated (e.g., sedimented into microstructures by centrifugation) in the sample and then detected in the microstructures, and in some embodiments, analytes that are representative of the presence of microorganisms can be concentrated (e.g., sedimented into microstructures by centrifugation) in the sample and detected in the microstructures. For example, in some embodiments, substrates can be added to the sample (e.g., X-gal sugar substrates, as described in Example 24) that precipitate after cleavage by the appropriate enzyme. Such precipitated substrates can be concentrated (e.g., sedimented into microstructures by centrifugation, along with the microorganisms/cells) and detected and/or quantified more quickly than they otherwise could be at a low concentration in a large volume sample.

Various examples of analytes are given above, including indicator dyes. In some embodiments, such an indicator dye can include a precipitating dye and/or an internalized dye. In the case of precipitated dyes, often the dyes are small molecules that diffuse out of the cells and which may need sufficient incubation time to reach a detectable concentration, even when concentrated in microstructures. However, in the case of internalized dyes, the cells (i.e., microorganisms) themselves can be 'marked' by the dye, and detection (e.g., presence/absence and/or quantification) can occur as soon as the cells have been concentrated into microstructures.

Another specific example of detection that could be performed using the systems and methods of the present disclosure involves detecting (e.g., for presence/absence and/or quantifying) microorganisms using chemiluminescence by concentrating the sample into the microstructures and adding the reagents for performing ATP-based detection. The reagents can be added either before or after centrifugation, or by having the reagents coated and/or dried in the microstructured recesses 136. In such embodiments, the reagents can include a lysis reagent, luciferin (substrate) and luciferase (enzyme). The lysis reagent can be used to break open the cells to release ATP, which the luciferase needs to cause luciferin to chemiluminesce. As a result, a microstructured recess 136 containing a microorganism of interest would be "marked" (e.g., would light up), whereas recesses not containing the microorganism would not be "marked" (e.g., would be dark), and the microorganisms can be detected indirectly.

Figure 2:
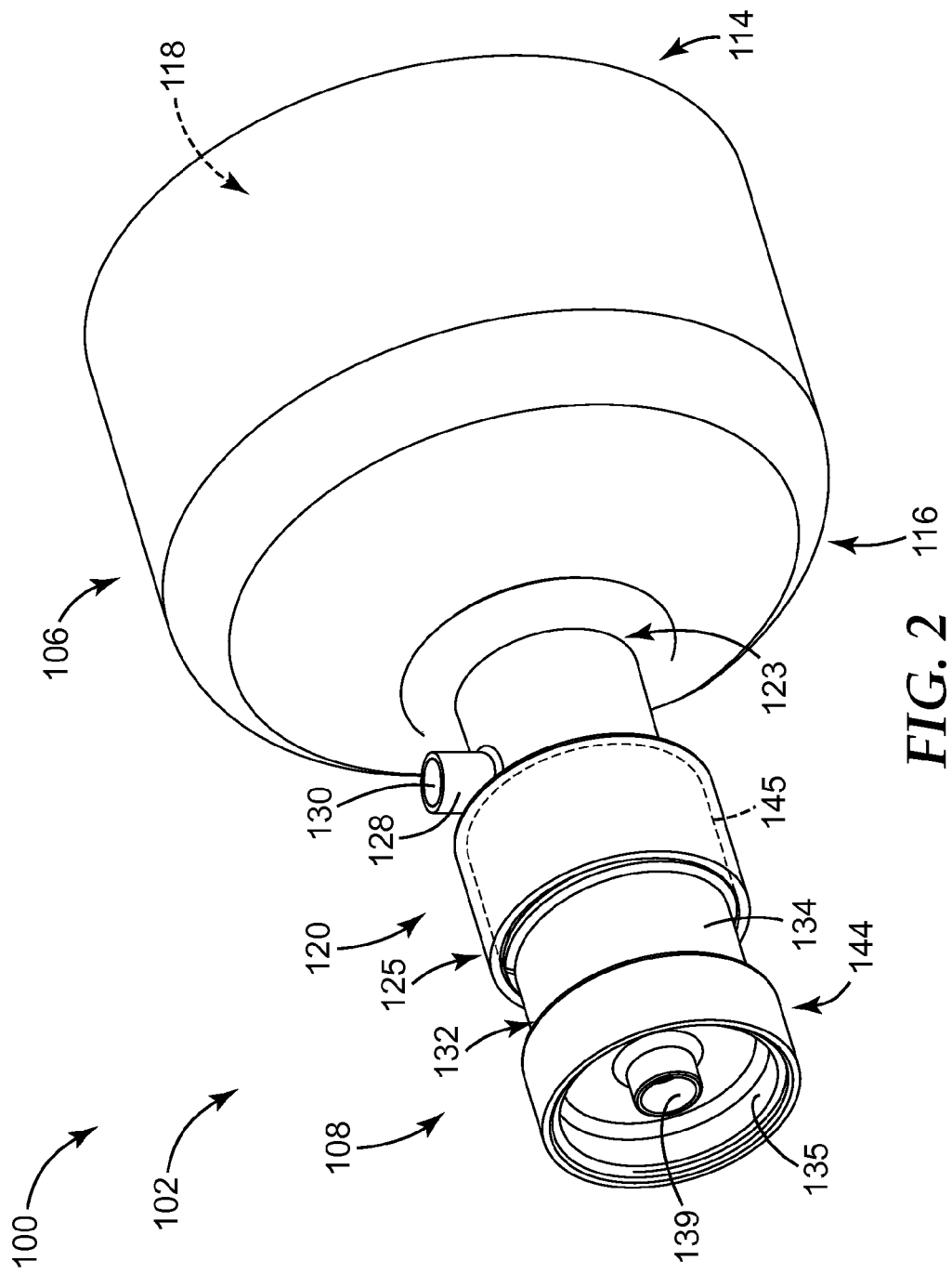
FIG. 2 is an assembled perspective view of the first container of FIG. 1.
Figure 5:
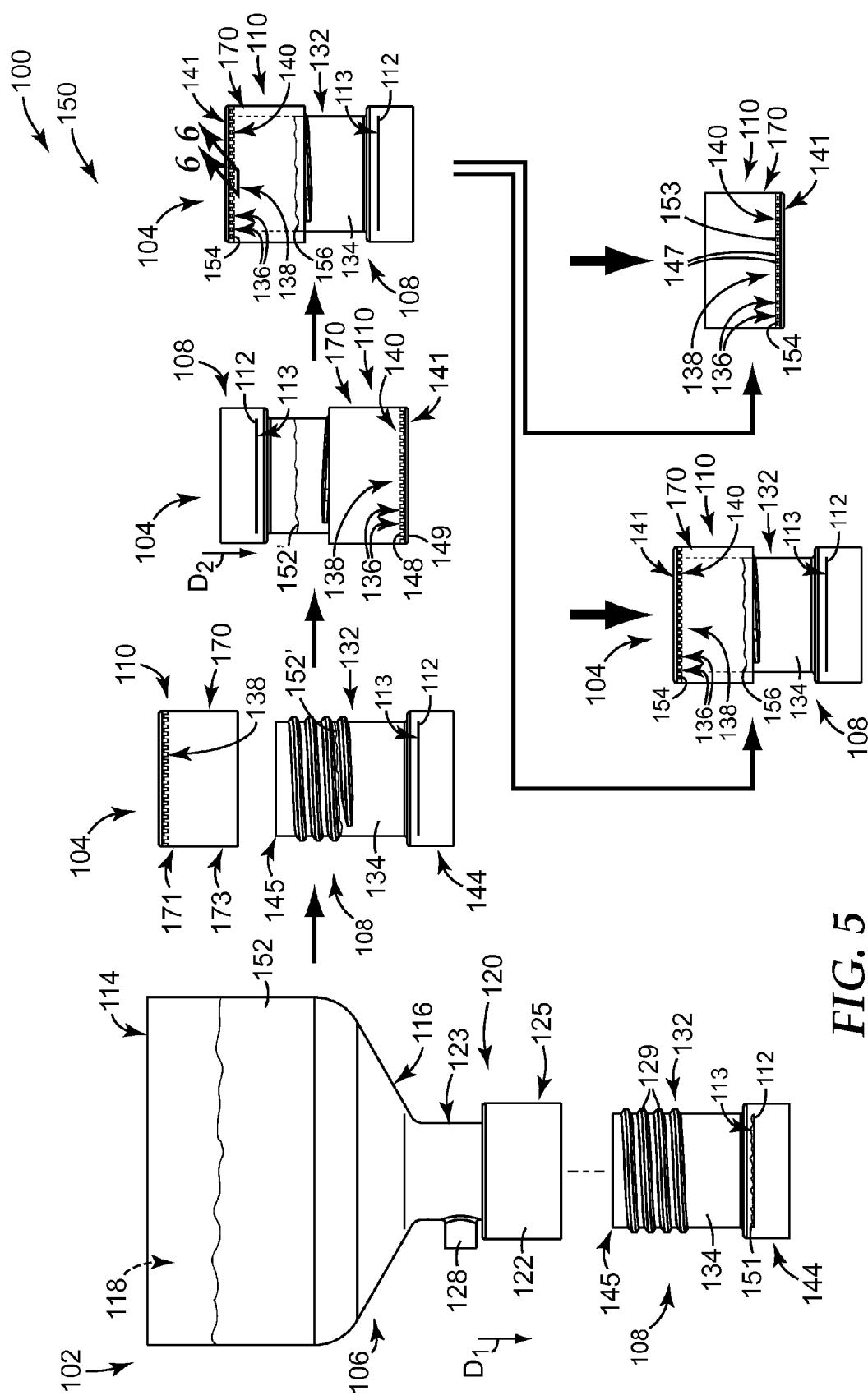
FIG. 5 illustrates a sample detection method according to one embodiment of the present disclosure, showing side elevational views of the first container of FIGS. 1-2, and the second container of FIGS. 3 and 4.

As shown in FIGS. 1, 2 and 5, the first container 102 can include a receptacle portion (or "first portion") 106 that is adapted to contain a sample (e.g., a large volume aqueous sample) and a filter portion (or "second portion") 108 that includes a filter 112 that can be configured to retain an analyte of interest from the sample, if present. The filter portion 108 and the receptacle portion 106 can be configured to be removably coupled together to form the first container 102.

Figure 3:
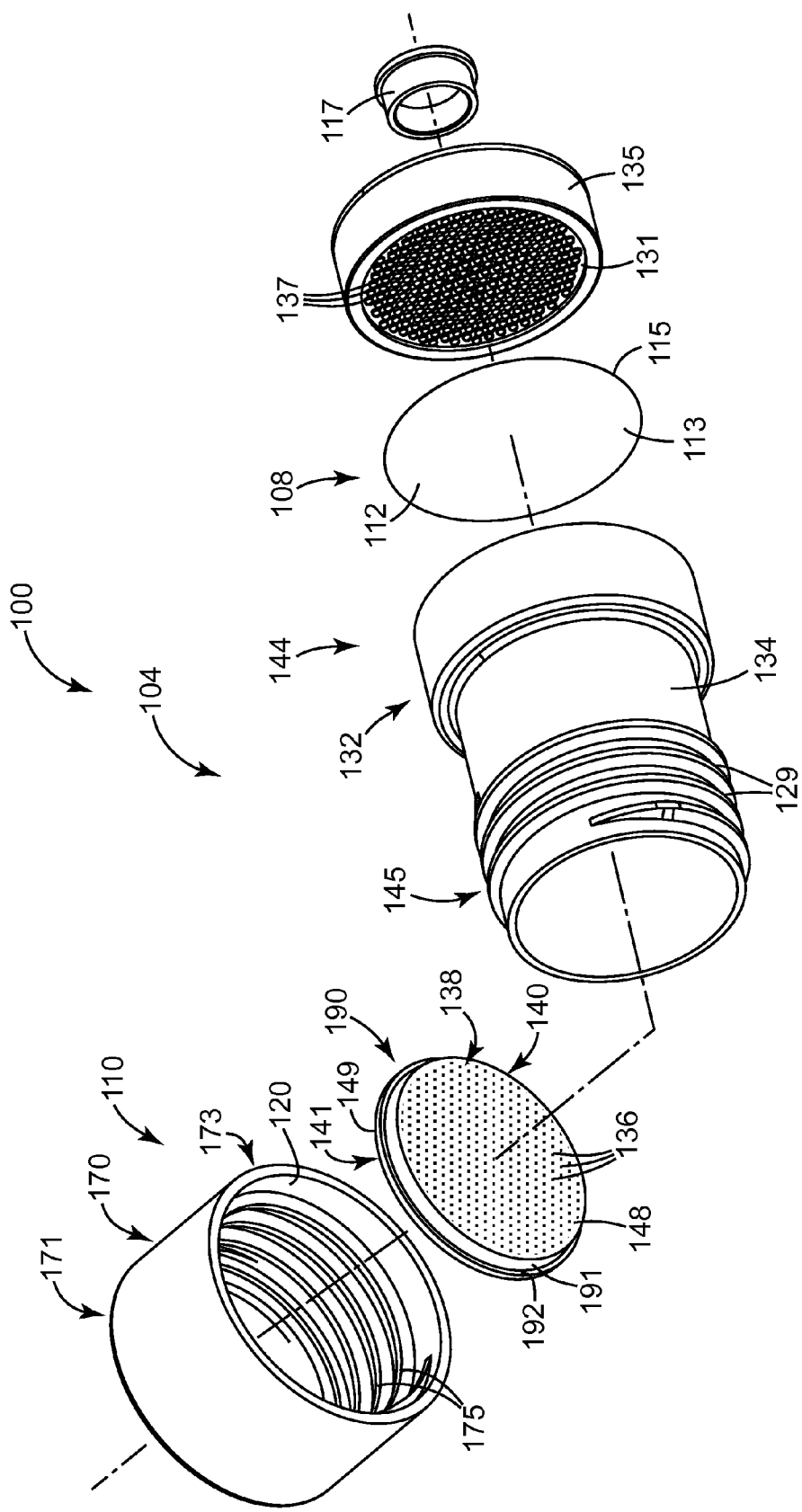
FIG. 3 is an exploded perspective view of a second container according to one embodiment of the present disclosure, the second container comprising the filter portion of FIGS. 1 and 2, and a detection portion.
Figure 4:
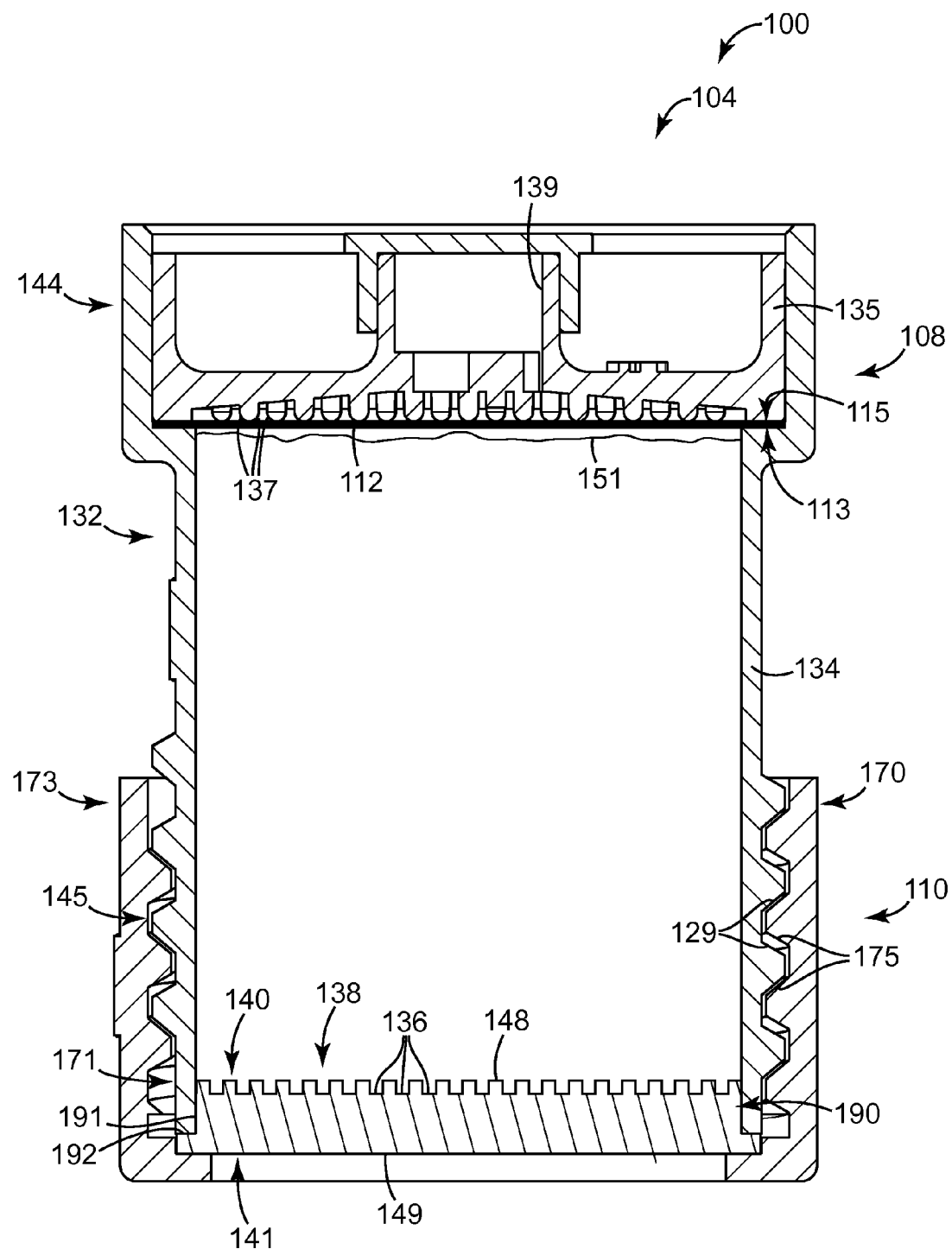
FIG. 4 is an assembled side cross-sectional view of the second container of FIG. 3.

As shown in FIGS. 3, 4 and 5, the second container 104 can include the filter portion 108 and a detection portion (or "third portion") 110. The filter portion 108 can therefore be used in both the first container 102 and the second container 104. The detection portion 110 can include a microstructured surface 138 that is adapted to receive a concentrate of the sample when the second container 104 is exposed to a centrifugal force, and is further adapted to retain at least a portion of the concentrate of the sample under normal gravitational forces (e.g., under standard gravity, i.e., the standard value of Earth's gravitational acceleration at sea level, 9.8 m/s$^2$).

In the illustrated embodiments, the filter portion 108 is shown as forming the "tube" or "receptacle" part of the second container 104, whereas the detection portion 110 forms more of the "cap" or "cover" of the second container 104. However, it should be understood that this need not be the case. Any shape or configuration can be employed for either the filter portion 108 or the detection portion 110, and no matter which forms the "tube" or "cap" part of the second container 104, the filter portion 108 will be the portion of the second container 104 that comprises the filter 112, and the detection portion 110 will be the portion of the second container 104 that comprises the microstructured surface 138.

In general, the first container 102 can be used to filter the sample by passing the sample through the filter portion 108, and particularly, through the filter 112 to form a filtrate and a filtrand of the sample. The filter portion 108 can then be removed from the receptacle portion 106 of the first container 102 and coupled to the detection portion 110 to form the second container 104. The second container 104 can then be centrifuged toward the microstructured surface 138 to move at least a portion of the filtrand from the filter 112 to the microstructured surface 138. In doing so, a sediment and a supernatant of the sample can be formed. The supernatant can be decanted form the microstructured surface 138, for example, by inverting the second container 104, and a concentrate can be retained in the microstructured surface 138. The concentrate can comprise the sediment, which can include one or more analytes of interest, if present in the sample. The microstructured surface 138 can then be interrogated for the analyte(s) of interest, while being retained in the detection portion 110. As a result, in some embodiments, the "concentrate" (i.e., a higher-concentration portion of the sample) can also be referred to as a "retentate." In some embodiments, the concentrate can be interrogated by removing the detection portion 110 from the filter portion 108, optionally sealing at least a portion of the detection portion 110, and interrogating the detection portion 110 from its open or closed end. Alternatively, the concentrate can be interrogated through the closed end of the detection portion 110.

An exemplary sample detection method of the present disclosure will be described in greater detail below with reference to FIG. 5. The sample detection system 100 will now be described in greater detail.

The first container 102, and particularly, the receptacle portion 106, can be adapted to contain a sample that is to be analyzed, for example, for one or more analytes of interest. The sample is generally a liquid sample, in some embodiments, is a dilute liquid sample (i.e., any analyte of interest present in the sample is present at a low concentration), and in some embodiments, is a dilute aqueous sample. The first container 102 (or the receptacle portion 106) can be sized and shaped, as desired, to accommodate the sample to be analyzed, and the shape and configuration of the receptacle portion 106 and the filter portion 108 is shown by way of example only.

The receptacle portion 106, the filter portion 108, and the detection portion 110 can be formed of a variety of materials, including, but not limited to, polymeric materials, metals (e.g., aluminum, stainless steel, etc.), ceramics, glasses, and combinations thereof. Examples of polymeric materials can include, but are not limited to, polyolefins (e.g., polyethylene, polypropylene, combinations thereof, etc.), polycarbonate, acrylics, polystyrene, high density polyethylene (HDPE), polypropylene, other suitable polymeric materials capable of forming a freestanding and/or self-supporting container, or a combination thereof. The receptacle portion 106, the filter portion 108, and the detection portion 110 can be formed of the same or different materials.

The receptacle portion 106 can include a first end 114 that at least partially defines a reservoir 118, and a second end 116 configured to be coupled to the filter portion 108 (i.e., either directly or indirectly). The first end 114 can either be an open end or a closed end. By way of example only, in FIG. 1, the first end 114 is open, such that a sample can be added to the reservoir 118 via the first end 114. In such embodiments, the open end can remain open, or it can be closed by a cover or lid (not shown), as long as there is an inlet located somewhere in the first container 102 to facilitate the filtration process. In embodiments in which the first end 114 is a closed end (see, e.g., FIGS. 7 and 8), the sample can be added to the reservoir 118 via another location (e.g., prior to coupling the receptacle portion 106 to the filter portion 108.

As shown in FIG. 1, the first container 102 can further include a filter connection assembly 120 for coupling the filter portion 108 and the receptacle portion 106 together. In some embodiments, the filter connection assembly 120 can be coupled (e.g., removably or permanently) to the receptacle portion 106, and in some embodiments, the filter connection assembly 120 can be integrally formed with the receptacle portion 106. By way of example only, the filter connection assembly 120 is illustrated in FIGS. 1 and 2 as being integrally formed with the receptacle portion 106.

As shown in FIG. 1, in some embodiments, the filter connection assembly 120 can include a connector 122 and a gasket 124. The gasket 124 can be configured to fit within the connector 122 to aid in creating a seal (e.g., a liquid-tight seal, a hermetic seal, or a combination thereof) between the receptacle portion 106 and the filter portion 108 to seal the interior of the first container 102 from ambience, while maintaining fluid communication between the receptacle portion 106 and the filter portion 108 via the aperture 126 formed therein.

The connector 122 can include a first end 123 configured to be coupled to the receptacle portion 106 and a second end 125 configured to coupled to the filter portion 108. By way of example only, the second end 125 is shown as including threads 127 that cooperate and engage with threads 129 of the filter portion 108 to allow the filter portion 108 to be screwed onto the filter connection assembly 120 for coupling to the filter connection assembly 120 and the receptacle portion 106. In some embodiments, the receptacle portion 106 or the filter portion 108 can itself include all of the features of the filter connection assembly 120. Alternatively, in some embodiments, the receptacle portion 106 and the filter portion 108 can be configured to be coupled directly to one another.

The threaded connection between the filter portion 108 and the receptacle portion 106 (or between the filter portion 108 and the detection portion 110) is shown by way of example only; however, in some embodiments, manufacturability may be enhanced by employing a friction-fit (e.g., press-fit) or snap-fit-type coupling means between these components.

As shown in FIGS. 1 and 2, the filter connection assembly 120 (e.g., the connector 122) can further include a vent port 128 and a filter plug 130 that can serve as an air inlet during the filtration process, particularly, in embodiments in which the first end 114 of the receptacle portion 106 is closed. The filter plug 130 can be used to filter inlet air as it enters the first container 102 during a filtration process. In some embodiments, the filter plug 130 can be formed of a hydrophobic material (e.g., polypropylene, polyethylene, polytetrafluoroethylene (PTFE), or a combination thereof) to inhibit sample leakage out of the vent port 128 and contamination into the vent port 128.

The filter portion 108 can include a filter housing 132 configured to house and retain the filter 112. In some embodiments, as shown in FIGS. 1 and 3, the filter housing 132 can be formed from more than one portion. By way of example only, the filter housing 132 includes a tube 134 and a base 135. In the illustrated embodiment, the base 135 can be dimensioned to be received in the tube 134, and the filter 112 can be positioned between a first or upper surface 131 of the base 135 and an inner flange 133 (see FIG. 1) in the tube 134. As shown in FIG. 3, the upper surface 131 of the base 135 can include or at least partially define a plurality of apertures 137 that are in fluid communication with an outlet 139. Such an outlet 139 can function as the outlet of the first container 102 and/or of the filter portion 108, and can be coupled to a suction source (not shown) to perform the filtration step to move the sample through the receptacle portion 106, the filter connection assembly 120 (if employed), and the filter portion 108.

In some embodiments, the filter housing 132 may not include the "tube" 134, but rather can include one of the base 135 and the tube 134. For example, in some embodiments, the filter housing 132 can include the base 135 structure that is configured to be coupled to the receptacle portion 106 (or the filter connection assembly 120, if employed), and the detection portion 110. In such embodiments, the detection portion 110 can include more of the "tube" structure for retaining sample volume. As shown in FIG. 4, in embodiments such as the embodiment illustrated in FIGS. 1-3 and 5 where the tube 134 and the base 135 are employed, the filter 112 can be retained (e.g., "sandwiched") between the tube 134 and the base 135. However, in embodiments in which only one of these types of structures is employed (e.g., the base 135), the filter 112 (e.g., a periphery thereof) can be ultrasonically welded to the filter housing 132 (e.g., a ledge or flange within the housing 132 on which the periphery of the filter 112 will sit). Such an ultrasonic weld can provide a hermetic seal, in addition to providing means for coupling the filter 112 to the filter housing 132. Still, in some embodiments, the filter 112 can be integrally formed with the filter housing 132.

The filter portion 108 (or the filter housing 132 or the tube 134) can include a first end 144 that comprises the filter 112 and the outlet 139, and a second end 145 configured to be coupled (e.g., removably) to the receptacle portion 106 (i.e., directly, or indirectly, e.g., via the filter connection assembly 120) and the detection portion 110, as described below. For example, as shown in FIG. 1, in some embodiments, the second end 145 can include the threads 129 for coupling with the threads 127 of the filter connection assembly 120 (or of the receptacle portion 106 if the filter connection assembly 120 is not employed). In addition, by way of example only, in some embodiments, the second end 145 can be dimensioned to be received in the second end 125 of the filter connection assembly 120 (or vice versa). Alternatively, if the filter connection assembly 120 is not employed, the second end 145 can be configured to be coupled directly to the receptacle portion 106.

In some embodiments, the tube 134 and the base 135 can be permanently coupled together, for example, using any of the below-described coupling means. In other embodiments, the tube 134 and the base 135 can be removably coupled together.

As mentioned above, the filter 112 can be configured to retain an analyte of interest from the sample, if present. The filter 112 can be configured either by size, charge, affinity, or other suitable means for retaining the analyte of interest. Any of the above-described filters or membranes can be employed in the present disclosure.

Particularly, exemplary filters 112 can be made by, for example, TIPS (thermally induced phase separation) process, SIPS (solvent induced phase separation) process, VIPS (vapor induced phase separation) process, stretching process, track-etching, or electrospinning (e.g., PAN fiber membranes). Suitable membrane materials include, for example, polyolefins (e.g., polyethylene and/or polypropylene), ethylene-chlorotrifluoroethylene copolymer, polyacrylonitrile, polycarbonate, polyester, polyamide, polysulfone, polyethersulfone, polyvinylidene fluoride (PVDF), cellulose ester, and/or combinations thereof.

Suitable membranes may be characterized as porous membranes or as nanofiber membranes. Nanofiber filter membranes can have the fiber diameter less than 5 µm such as, for example, less than 1 µm. Nanofiber membranes may be prepared from, for example, polyacrylonitrile, polyvinylidene fluoride, a cellulose ester, polyvinyl acetate, polyvinyl alcohol, polyvinyl butyral, and/or combinations thereof.

Certain TIPS polyolefin membranes can be prepared so that they possess a single, homogeneous zone of membrane structure, each zone having a different pore microstructure. In other cases, a TIPS membrane may be prepared as a multi-zone membrane that includes two or more zones, each zone having a different pore microstructure. A multi-zone TIPS membrane may contain distinct zones or, alternatively, may possess a transition zone between two otherwise distinct zones. Such multi-zone filters can be particularly useful in the systems and methods of the present disclosure due to the efficient elution. In embodiments employing such multi-zone filters, the side of the filter comprising the smallest pore zone can be employed as the first side 113.

Exemplary filter membranes include membranes and methods for making exemplary filter membranes are described in, for example, in U.S. Pat. No. 4,539,256, U.S. Pat. No. 4,726,989, U.S. Pat. No. 4,867,881, U.S. Pat. No.

5,120,594, U.S. Pat. No. 5,260,360, International Patent Publication No. WO2010/078234, International Patent Publication No. WO2010/071764, PCT Publication WO2011/152967, and PCT Publication WO2011/153085.

The filter 112 can include a first side 113 that faces the receptacle portion 106 during the filtration step and which faces the detection portion 110 during the centrifugation step, and a second side 115 that faces the outlet 139. During filtration, the sample is separated into a filtrand 151 (see FIGS. 4 and 5) that is retained on the first side 113 of the filter 112 and a filtrate. As described above, the filtrate can either be discarded or can be re-run through the sample processing to try to obtain further analyte(s) of interest, or otherwise processed.

While the filtrand 151 may be described as being retained on the first side 113 of the filter 112, this does not necessarily mean that the filtrand 151 is not present in any of the depth of the filter 112 (as would be the case for an isoporous membrane). Rather, this means that the sample was filtered through the filter 112 from the first side 113 to a second (opposite) side, and that the first side 113 is the side of the filter 112 that faces both the receptacle portion 106 during filtration and the detection portion 110 during centrifugation. It is possible that at least some of the filtrand may be present below the surface of the first side 113 of the filter 112, that is, at least partially into the depth of the filter 112. However, particular filters or types of filters (e.g., multi-zone filters) can be employed to inhibit the sample from moving too far into the depth of the filter 112 that significant time and elution efforts are required to retrieve the filtrand 151 from the filter 112.

As shown in FIG. 5, the second end 145 of the filter portion 108 and the second end 125 of the filter connection assembly 120 (or the second end 123 of the receptacle portion 106) can be coupled together, and oriented in a first orientation, e.g., upright. A sample 152 can be added to the reservoir 118 of the receptacle portion 106, the outlet 139 of the filter portion 108 can be coupled to a suction source, and the sample 152 can be filtered in a first direction $D_1$ toward the filter 112, a filtrate of the sample 152 moving out of the filter portion 108, and a filtrand 151 of the sample 152 being retained on the first side 113 of the filter 112.

The receptacle portion 106 and the filter portion 108, or a portion thereof, can be substantially transparent, opaque (i.e., substantially non-transparent), or somewhere in between (e.g., translucent), and can be any suitable size, depending on the type, amount and/or size of sample to be analyzed, and the type, amount and/or size of concentrate to be collected and interrogated.

With reference to FIGS. 3, 4 and 5, the second container 104 will now be described. As mentioned above, the second container 104 can include the filter portion 108 and the detection portion 110. The detection portion 110 can include the microstructured surface 138. In the embodiment illustrated in FIGS. 3, 4 and 5, the microstructured surface 138 is provided by a substrate (or "insert" or "lens") 190 that is configured to be retained within and coupled to a detection housing 170.

The detection portion 110 (or, specifically, the detection housing 170) can be tubular in shape, as shown in FIG. 3, and can include a first end 171 that comprises the microstructured surface 138 and a second end 173 that is configured to be coupled to the second end 145 of the filter portion 108. As shown in FIG. 3, in some embodiments, the detection housing 170 can be dimensioned to receive at least a portion of the filter portion 108, and the detection housing 170 (or the detection portion 110) can include a plurality of threads 175 that are configured to cooperate and engage with the threads 129 of the filter portion 108 to allow the detection portion 110 and the filter portion 108 to be screwed together, and particularly, to be removably coupled together. In some embodiments, however, the filter portion 108 and the detection portion 110 can be removably coupled together by other means (e.g., any of those described above), or permanently coupled together, for example, in embodiments in which the detection portion 110 and the filter portion 108 will not need to be decoupled. In such embodiments, the entire second container 104 can be disposable, and can be discarded following the detection process. It should be understood, however, that in some embodiments, the filter portion 108 can instead be dimensioned to receive at least a portion of the detection portion 110.

By way of example only, the filter portion 108 is illustrated as being the larger portion of the second container 104, such that the filter portion 108 acts as the tube or reservoir of the second container 104, and the detection portion 110 acts as the cap or cover of the second container 104. However, it should be understood that the sizes, shapes, and relative sizes of the components of the second container 104 can be adjusted to suit a particular sample or situation.

In embodiments such as those shown in FIG. 3, where the microstructured surface 138 is formed in a substrate 190, the detection housing 170 can be dimensioned to receive the substrate 190, and the detection housing 170 and the substrate 190 can be configured accordingly. For example, as shown in FIG. 3, in some embodiments, the substrate 190 can include a can include an outer wall 191 and a flange 192 that can be used for coupling to detection housing 170. The detection housing 170 can include mating ridges or features for engaging at least one of the outer wall 191 and the flange 192. For example, in some embodiments, the substrate 190 can couple to the detection housing 170 to form a cap for the second container 104, much like that of a mason jar that has a lid, and a cover that is configured to couple to the jar as well as hold the lid in place over the open end of the jar. That is, the substrate 190 can function as a lid and the detection housing 170 can function as a screw-top cap, and together, they can form a cap or a cover for the filter portion 108. Any description of the substrate 190 herein can also be applied to a "detection portion" of the present disclosure, for example, in which the microstructured surface 138 is formed directly into the detection housing 170, rather than in a substrate 190 that is inserted into the detection housing 170.

The substrate 190 can further include a first side 140 having a first major surface 148 in which the microstructured surface 138 is formed, and a second side 141 having opposite the first side 140 and having a second major surface 149, such that the first side 140 would generally face an interior of the second container 104, and the second side 141 would generally face an exterior of the second container 104. The second side 141 therefore also generally faces away from the filter portion 108. As a result, the concentrate retained in the detection portion 110 can be interrogated from the first side 140 or from the second side 141, for example in embodiments in which at least a portion of the detection portion 110 (e.g., the first (closed) end 171 and/or the second side 141) is substantially transparent. In some embodiments, at least a portion of the recesses 136 (e.g., a base 146 thereof) can be substantially transparent to allow the contents of the recesses 136 to be viewed, detected and/or interrogated from the second side 141.

In some embodiments, the detection portion 110 (e.g., the substrate 190) can include one or more recesses 136 adapted to retain a concentrate of the sample to be analyzed, each recess 136 opening toward the second (open) end 173 of the detection portion 110. Each recess 136 can include at least one of a well, a depression, a channel, and the like, and combinations thereof. In some embodiments, the one or more recesses 136 can include the channels or interstitial spaces between outwardly-projecting microstructures, such as those described in Ylitalo et al., U.S. Pat. No. 6,386,699. In some embodiments, one or more of the recesses 136 can include a surface modification (e.g., such as a hydrophilic/oleophilic surface treatment or coating) to facilitate retaining a concentrate of interest. The recesses 136 need not all be the same shape or size, and in some embodiments, the detection portion 110 includes a variety of recesses 136, ranging from microstructured to larger, and having a variety of shapes and configurations.

In some embodiments, the one or more recesses 136 can be formed directly into an inner surface of the detection portion 110 (e.g., in the detection housing 170), and in some embodiments, as shown in FIG. 3, the one or more recesses 136 can be formed in a substrate 190 that is coupled to the detection housing 170, and which can form a portion of the second container 104. Additional examples of substrates will be described in greater detail below with reference to FIGS. 18A-18H and FIGS. 19A-19H. In embodiments in which the recesses 136 are formed directly into the detection portion 110, the same general configuration of the first side 140, the first major surface 148, the second side 141, and the second major surface 149 can be employed, except that the substrate 190 is integrally formed with the detection housing 170 and is not insertable or removable from the detection housing 170. By way of example only, in either configuration (e.g., a removable substrate 190 or features integrally formed in the detection portion 110), such recesses 136 can be formed by a variety of methods, but can particularly be formed by a molding process. As such, the first side 140, the first major surface 148, the second side 141, and the second major surface 149 of the substrate 190 can also be described more broadly as the first side 140, the first major surface 148, the second side 141, and the second major surface 149 of the detection portion 110.

In some embodiments, at least a portion of an inner surface of the detection portion 110 (e.g., of the detection housing 170) can include the microstructured surface 138. In embodiments employing the microstructured surface 138, the one or more recesses 136 can be microstructured recesses 136, and the microstructured surface 138 can include a variety of microstructured features.

As shown in FIG. 3, in some embodiments, the outlet 139 of the filter portion 108 that is used in the filtration step to remove the filtrate and to perform a first sample concentration step can be sealed or closed, for example, by a cap 117. For example, the cap 117 can be coupled to the outlet 139 following the filtration step, and particularly when the filter portion 108 and the detection portion 110 are coupled together to form the second container 104.

In some embodiments, the original sample volume (i.e., prior to any concentration steps, including filtration and/or centrifugation) to be tested for the analyte(s) of interest can be at least about 5 mL, in some embodiments, at least about 10 mL, in some embodiments, at least about 25 mL, in some embodiments, at least about 50 mL, in some embodiments, at least about 100 mL, in some embodiments, at least about 500 mL, in some embodiments, at least about 1 L, in some embodiments, at least about 2 L, in some embodiments, at least about 5 L, and in some embodiments, at least about 10 L.

In some embodiments, the volume of the filter portion 108 or the second container 104 can range from about 1 mL to about 250 mL. As a result, in some embodiments, the volume of the sample (e.g., a sample formed from the filtrand 151 of the original sample 152 and one or more diluents that are added post-filtration) can be at least about 1 mL, in some embodiments, at least about 10 mL, and in some embodiments, at least about 100 mL. In some embodiments, the volume of the sample is no greater than about 200 mL, in some embodiments, no greater than about 100 mL, in some embodiments, no greater than about 75 mL, and in some embodiments, no greater than about 50 mL. In some embodiments, the volume of the sample ranges from about 1 mL to about 100 mL.

In some embodiments, the detection portion 110 can include a volume and/or the one or more recesses 136 include a collective volume of (i.e., a capacity to retain a volume of concentrate of) at least about 1 microliter ($\mu L$), in some embodiments, at least about 5 $\mu L$, in some embodiments, at least about 10 $\mu L$, and in some embodiments, at least about 25 $\mu L$. In some embodiments, the detection portion 110 can include a volume and/or the one or more recesses 136 include a collective volume of no greater than about 200 $\mu L$, in some embodiments, no greater than about 100 $\mu L$, in some embodiments, no greater than about 75 $\mu L$, and in some embodiments, no greater than about 50 $\mu L$. In some embodiments, the volume of the detection portion 110 and/or the collective volume of the one or more recesses 136 ranges from about 1 $\mu L$ to about 100 $\mu L$. In some embodiments, these volumes can be reported as volume per unit area (e.g., $\mu L$ per $cm^2$), so that collective volume of the recesses 136 can be independent of the overall dimensions of the detection portion 110.

In some embodiments, the ratio of the volume of the filter portion 108 or the second container 104 to the volume of the concentrate (or retentate) of the sample that is retained in the detection portion 110 (or the "cap," "cover," or "cap portion" of the second container 104) is at least about 10:1, in some embodiments, at least about 100:1 ($10^2$:1), in some embodiments, at least about 1000:1 ($10^3$:1), in some embodiments, at least about 10,000: 1 ($10^4$:1), and in some embodiments, at least about 100,000:1 ($10^5$:1). In some embodiments, the ratio of the volume of the filter portion 108 or the second container 104 to the volume of the concentrate captured in the detection portion 110 ranges from about 10:1 to about $10^5$:1.

In some embodiments, the concentration increase (i.e., the concentration (e.g., of the more dense matter, such as the analyte(s) of interest) of the resulting concentrate retained in the detection portion 110, divided by the concentration of the initial sample (either before or after filtration), expressed as a ratio) can be at least about 10:1, in some embodiments, at least about 100:1 ($10^2$:1), in some embodiments, at least about 1000:1 ($10^3$:1), in some embodiments, at least about 10,000: 1 ($10^4$:1), and in some embodiments, at least about 100,000:1 ($10^5$:1). In some embodiments, the concentration efficiency ranges from about 10:1 to about $10^5$:1.

In some embodiments, the receptacle portion 106 of FIGS. 1 and 2 can have a capacity of at least about 1 mL, at least about 5 mL, at least about 10 mL, at least about 25 mL, at least about 50 mL, at least about 100 mL, or at least about 250 mL. That is, in some embodiments, the capacity, or volume, of the receptacle portion 106 can range from about 1 mL to about 250 mL, and in some embodiments, can range from about 1 mL to about 100 mL. In some embodiments, the filter portion 108, the detection portion 110, and/or the second container 104 can have a capacity of no greater than about 1 mL, no greater than about 2 mL, no greater than about 5 mL, or no greater than about 10 mL.

The shapes, dimensions and coupling means for the receptacle portion 106, the filter portion 108, and the detection portion 110 are described above and illustrated in FIGS. 1-3 and 4-5 by way of example only. It should be understood, however, that a variety of shapes and dimensions of the receptacle portion 106, the filter portion 108, and the detection portion 110 can be used. In addition, a variety of coupling means can be employed to removably and/or permanently couple the receptacle portion 106 and the filter portion 108, as well as the filter portion 108 and the detection portion 110, including, but not limited to, screw threads (as shown), a clamp (e.g., a spring-loaded clamp, a snap-type clamp, etc.); a clip (e.g., a spring-loaded clip, etc.); ties (e.g., wire ties); one or more magnets; tape; an adhesive; a cohesive; a hook-and-loop fastener; snap-fit engagement (e.g., wherein the detection portion 110 functions as a flip-top cap); press-fit engagement (also sometimes referred to as "friction-fit engagement" or "interference-fit engagement"); thermal bonding (e.g., heat and/or pressure applied to one or both of the components to be coupled); welding (e.g., sonic (e.g., ultrasonic) welding); other suitable coupling means; and combinations thereof.

With reference to FIG. 5, a sample detection method 150 will now be described, with continued reference to the sample detection system 100 of FIGS. 1-3 and 4, with the microstructured surface 138 shown schematically for illustration purposes.

The first step, i.e., the filtration step, of the sample detection method 150 was described above with respect to the first container 104. The filtration step can sometimes be referred to as a first concentration step of the sample detection method 150, and the following centrifugation step can sometimes be referred to as a second concentration step, such that the sample detection method 150 can be described as including two concentration steps to achieve a concentrate of the sample that can be interrogated for the analyte(s) of interest.

The filtrand 151 of the sample 152 that is retained on the first side 113 of the filter 112 can then be retrieved from the filter 112 using a variety of means, including, but not limited to, elution, agitation, washing, other suitable means for retrieving the filtrand 151 form the filter 112, or combinations thereof. For example, in some embodiments, retrieving the filtrand 151 can include adding one or more diluents (e.g., an elution solution and/or a wash solution) to the filter portion 108 (or the second container 104), for example, prior to coupling the filter portion 108 to the detection portion 110. An elution solution can be configured for eluting the filtrand 151 from the filter 112, for example, by disrupting any affinity between the filtrand 151 and the filter 112. In some embodiments, after one or more diluents are added to the filter portion 108, the detection portion 110 can be coupled to the filter portion 108 to form the second container 104, and the second container 104 can be agitated to assist in removing the filtrand 151 from the filter 112. A new "sample" 152' can thus be formed comprising the filtrand 151 and any diluents that are added.

Particularly, in the embodiment illustrated in FIGS. 1-3 and 4-5, in forming the second container 104, the second (open) end 145 of the filter portion 108 can be inserted into the second (open) end 173 of the detection portion 110, and the threads 129 of the filter portion 108 and the threads 175 of the detection portion 110 can screwed together.

As shown in the third step of FIG. 5, the second container 104 can then be inverted to a second orientation, and the second container 104 can be inverted and centrifuged in a second direction (or orientation) $D_2$ toward the detection portion 110. Such a centrifugation process can cause a concentrate 154 (see FIG. 6) comprising the more dense matter of the original sample 152 (and the filtered sample 152') to be moved into the detection portion 110, and particularly, into the one or more recesses 136 formed in the detection portion 110. The "concentrate" 154 can generally include a sediment of the sample 152, 152' that is formed as a result of the centrifugation process, but can also include at least some of the supernatant, or diluent, of the sample 152, 152', as will be described in greater detail below with reference to FIG. 6.

In the centrifugation step shown in the third step of FIG. 5, the centrifugation g-force, duration and/or number of cycles necessary to form and retain the concentrate 154 in the detection portion 110 can vary depending on one or more of the composition of the sample 152', the analyte(s) of interest, and the like. In some embodiments, the amount of g-force required to concentrate the analyte(s) of interest can depend on the size and density of the analyte, the density and viscosity of the diluent, and the volume of sample 152' in the second container 104 (i.e. the height of the sample 152' in the second container 104 defines the distance the analyte needs to migrate under a specified g-force to reach the recesses 136 in the detection portion 110). The sedimentation velocity (V, in centimeters per second (cm/s)) can be approximated using Equation 1:

$$V=2ga^2(\rho 1-\rho 2)/9\eta \quad (1)$$

where g=acceleration in cm/s$^2$ (i.e., g-force in gs*980 cm/s$^2$), ρ1=analyte density in g/cm$^3$, ρ2=density of sample media (e.g., diluent) in g/cm$^3$, η=coefficient of viscosity in poises (g/cm/s), and a=analyte radius in centimeters (assuming a spherical shape). In some centrifuges, the g-force can be determined by the rotational speed (e.g., in revolutions per minute (RPM)) and the distance of the sample from the center of the rotor (i.e. the sample experiences a higher g-force at the same rotational speed if it is placed further away from the rotor). As a result, in order to collect the analyte(s) of interest that may reside in the sample 152' furthest from the detection portion 110, the distance between the center of the rotor and the height of the sample 152' positioned closest to the rotor can be calculated to estimate what the g-force would need to be to move the analyte(s) of interest the furthest distance in the sample to maximize collection of the analyte(s) of interest.

The sedimentation velocity can be calculated using the above equation, and then the centrifugation time (i.e., duration) can be calculated by dividing the distance (e.g., the maximum distance) the analyte(s) of interest, if present, would need to travel, by the sedimentation velocity. Alternatively, the desired time and distance can be used to estimate a sedimentation velocity, and the necessary g-force can then be calculated using Equation 1.

In some embodiments, the g-force in the centrifugation step can be at least about 500·g (e.g., 500*9.8 m/s$^2$ on earth, at sea level), in some embodiments, at least about 1000·g, and in some embodiments, at least about 5000·g. In some embodiments, the g-force in the centrifugation step can be no greater than about 100,000·g, in some embodiments, no greater than about 50,000·g, and in some embodiments, no greater than about 10,000 vg.

In some embodiments, the duration of the centrifugation step can be at least about 1 minute, in some embodiments, at least about 5 minutes, and in some embodiments, at least about 10 minutes. In some embodiments, the duration of the centrifugation step can be no greater than about 120 minutes, in some embodiments, no greater than about 60 minutes, and in some embodiments, no greater than about 20 minutes.

As shown in the fourth step of FIG. 5, the second container 104 can then be inverted after centrifugation, such that a supernatant 156 resulting from the centrifugation step is decanted from the detection portion 110, while the concentrate 154 remains retained in the detection portion 110. The term "inverted" is used herein to refer to a change in orientation and can include orienting at a variety of angles, and is not limited to changing the orientation by 180 degrees. The detection portion 110 can be adapted to retain the concentrate 154 under normal gravitational forces (e.g., under standard gravity, i.e., the standard value of Earth's gravitational acceleration at sea level, 9.8 m/s$^2$).

The present inventors unexpectedly discovered that, in some embodiments, the speed of inverting the second container 104 can affect how the concentrate 154 is retained in the detection portion 110, and particularly, in the microstructured surface 138. For example, in some embodiments, if the speed of inversion was too high, portions of the sample may get hung up on various surfaces, edges or corners (e.g., sharp edges or corners) of the microstructured surface. That is, portions of the sample (e.g., an aqueous sample) may undesirably collect above the recesses 136 in relatively larger drops, rather than being partitioned into small-volume, high-concentration aliquots in the recesses 136. Any analyte(s) of interest present in these larger-volume drops may not be able to be properly detected (e.g., during imaging or optically interrogating) at least partly because the analyte(s), if present, will have a lower concentration in these larger volumes, and/or because the larger-volume drops may not be suitably positioned for detection. In addition, if the analyte(s) of interest include a motile microorganism, such "bridges" or "drops" that overlap multiple recesses 136 may allow for migration of microorganisms, rather than discrete separation that can be useful for enumeration of the microorganisms.

However, if the second container 104 is inverted at an appropriate rotational speed and/or over an appropriate angle (in degrees), the concentrate 154 can be acceptably separated from the remainder of the supernatant 156, such that the concentrate 154 is substantially contained in the recesses 136. "Substantially contained" can generally refer to the concentrate being contained within the recesses 136 with no visible (i.e., with the unaided or naked eye) bridges or drops formed across the first major surface 148 that may contain a larger volume of the sample 152' or of the concentrate 154.

In some embodiments, the speed of inversion can be no greater than about 20 degrees/sec, in some embodiments, no greater than about 10 degrees/sec, and in some embodiments, no greater than about 4.3 degrees/sec. Such values were arrived at empirically, as described in Example 14, where the containers were inverted from −30 degrees (relative to a horizontal) to +30 degrees; that is, through 60 degrees. Reported another way, in some embodiments, the speed of inversion can be no greater than about 0.4 rpm, in some embodiments, no greater than about 0.35 rpm, in some embodiments, no greater than about 0.3 rpm, in some embodiments, no greater than about 0.25 rpm, in some embodiments, no greater than about 0.20 rpm, and in some embodiments, no greater than about 0.15 rpm. In some embodiments, the speed of inversion can be 0.3 rpm, in some embodiments, the speed of inversion can be 0.2 rpm, and in some embodiments, the speed of inversion can be 0.7 rpm.

In some embodiments, the inverting step can include inverting the second container 104 by at least 20 degrees (e.g., from −10 degrees to +10 degrees, or from 0 degrees to +20 degrees, etc.), in some embodiments, by at least 45 degrees, in some embodiments, by at least 60 degrees, in some embodiments, by at least 90 degrees, and in some embodiments, by 180 degrees. For example, in embodiments in which the detection portion 110 is oriented at −90 degrees (e.g., from a horizontal), as shown in FIG. 2A, the second container 104 may need to be inverted at least 90 degrees (e.g., to 0 degrees) or more in order to adequately clear the detection portion 110 (and the microstructured surface 138) of the supernatant 156.

As shown in FIG. 5, the concentrate 154 in the detection portion 110 can then be interrogated (e.g., optically interrogated). In some embodiments, as shown in the first option of the fifth step of FIG. 5, the concentrate 154 can be interrogated from the outside or exterior of the second container 104, i.e., from the second side 141 of the detection portion 110 (e.g., the second side 141 of the substrate 190) and facing the second major surface 149, as represented by the large arrow. As such, the recesses 136 can be detected from their closed ends or bases 146. In such embodiments, as described above, the detection portion 110, or at least a portion thereof, can be substantially transparent in order to enable interrogating (e.g., optically) the concentrate 154 from the second side 141. Also, such embodiments can employ a filter portion 108 and a detection portion 110 that are permanently coupled together, because the detection, or interrogation, step can be performed from the outside of the second container 104, such that the detection portion 110 need not be decoupled from the filter portion 108 for the interrogation step. Also, in such embodiments, as shown, the supernatant 156 can serve as a humidity reservoir to avoid substantial evaporation of the concentrate 154 before the detection process can be completed.

The interrogation of the concentrate 154 can include any of the above-described detection methods for detecting an analyte of interest in a sample, including optical interrogation methods, such as optical scanning, imaging, or any of the other methods described above. For example, fluorescent detection can include directing electromagnetic energy toward the concentrate 154 in the microstructured surface 138 at a first frequency, and detecting electromagnetic energy emitted from the concentrate 154 in the microstructured surface 138 at a second frequency. By way of further example, colorimetric detection can include emitting electromagnetic energy at the concentrate 154 in the microstructured surface 138 at a broad range of frequencies (i.e., broad-spectrum light), and detecting at least one of the transmittance and the absorbance of at least a portion of the concentrate 154 in the microstructured surface.

In some embodiments, the recesses or wells 136 (e.g., microstructured recesses) can include bases that are formed by at least a portion of the second side (or second major surface) 141 of the detection portion 110, and which are substantially transparent, such that the contents of the recesses 136 can be visible from the second side 141 of the detection portion 110 (i.e., from the outside of the second container 104). In such embodiments, any sidewalls of the recesses 136 can be substantially non-transparent to inhibit cross-talk between wells, and to enhance detection, particularly, optical detection or interrogation.

In some embodiments, at least a portion of the detection portion 110 can include an optical window that is substantially transparent. The optical window can be at least partially coextensive (i.e., overlapping) with the recesses 136

(e.g., microstructured surface 138), such that at least some of the recesses 136 (and their contents) are visible from the outside of the second container 104, and particularly from the second side 141 of the detection portion 110.

While the detection portion 110 (e.g., the substrate 190) is shown by way of example only as generally having a flat, planar first side 140 and second side 141, this need not be the case. While a flat, planar side may aid in detection, the detection portion 110 can have any suitable shape or construction.

As shown in FIG. 5, in some embodiments, the filter portion 108 and the detection portion 110 of the second container 104 can remain coupled together (e.g., via a removable or permanent coupling) during the centrifuging step, the inverting step, and the detection or interrogation step. However, in some embodiments, as described with reference to the second option of the fifth step in FIG. 5, the detection portion 110 can be removed from the filter portion 108, after centrifuging, and optionally during or after inverting.

That is, in some embodiments, the filter portion 108, comprising the supernatant 156, can be used in subsequent processing steps (e.g., repeated centrifugation steps), and in some embodiments, the filter portion 108 and/or the supernatant 156 can be discarded.

As a result, in the second option of the fifth step of FIG. 5, only the detection portion 110 is shown. Note that the detection portion 110 has been inverted such that the recesses 136 (e.g., the microstructured surface 138) are facing upwardly. This need not be the case, but this orientation may aid in subsequent detection steps. As shown, a cover or seal 153 can optionally be placed over the recesses 136 to inhibit evaporation of the concentrate 154. Such a seal 153 can include any suitable seal, and can include, but is not limited to, any substantially transparent film or tape comprising an adhesive configured to adhere to a wet surface, such as a silicone polyurea adhesive, as described in U.S. Pat. No. 6,730,397, which is incorporated herein by reference; any substantially transparent film configured to be thermally sealed over the microstructured surface 138; other suitable seals; and combinations thereof.

As represented by the large arrow, the concentrate 154 can then be interrogated from the first side 140 of the detection portion 110, or from an interior of the detection portion 110, or facing the first major surface 148. In such embodiments, the detection portion 110 need not include any substantially transparent portions, because open ends 147 of the recesses 136 will be facing the direction from which the concentrate 154 within the recesses 136 will be interrogated. However, it should be understood that the detection portion 110, or a portion thereof, can still be substantially transparent, if desired.

Figure 6:
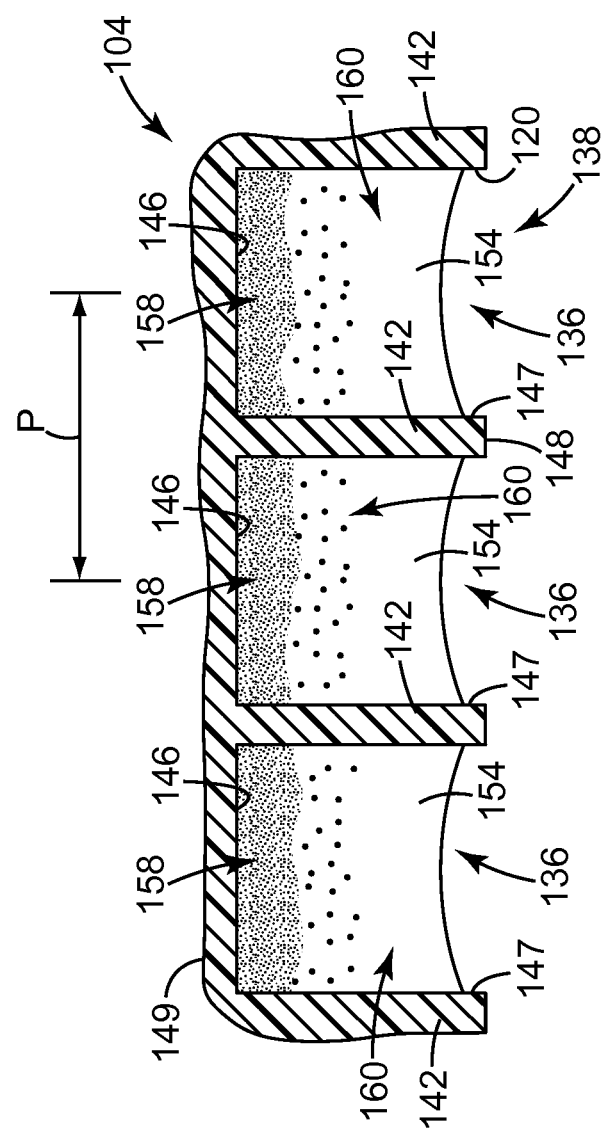
FIG. 6 is an enlarged schematic partial cross-sectional view of a portion of the detection portion of FIGS. 3, 4 and 5, taken along line 6-6 of FIG. 5.

FIG. 6 illustrates a schematic cross-sectional view of the detection portion 110, taken along line 6-6 of FIG. 5, with the concentrate 154 retained in the recesses 136 of the detection portion 110. As shown in FIG. 6, the one or more recesses 136 (e.g., microstructured recesses 136 forming a microstructured surface 138) can be formed in an inner surface 120 (see FIGS. 3 and 4) or the first major surface 148 of the detection portion 110. In some embodiments, as shown in FIG. 6, the concentrate 154 can include insoluble matter 158 and a liquid 160, which can also include soluble matter, and particularly, soluble matter having a lower density than the insoluble matter 158. The concentrate 154, and particularly, the insoluble matter 158 (if present) can include the analyte(s) of interest (e.g., the microorganism(s) of interest or an analyte representative of the microorganism(s) of interest), if present in the sample 152, 152'.

The sample detection method 150 illustrated in FIG. 5, respectively, and described above can provide efficient collection of the concentrate 154 of the sample 152, 152' (i.e., and any analyte(s) of interest that may be present in the sample 152, 152') with minimal loss of the sample 152, 152' and/or the concentrate 154. For example, efficient collection can be achieved by essentially "trapping" the concentrate 154 (comprising the analyte(s) of interest, if present) in the detection portion 110 during the centrifugation step illustrated in third step of FIG. 5. The concentrate 154 can generally have a much higher concentration than the sample 152, 152' of any analyte(s) of interest that may have been present in the sample 152, 152'.

Based on the centrifugation parameters employed in the centrifugation step, and/or on the number, shape and dimensions of the recesses 136 employed in the detection portion 110, the mass and/or volume of the concentrate 154 retained in the detection portion 110 can be determined That is, the detection portion 110 (and/or the centrifugation steps) can be configured according to the sample 152, 152' to be concentrated and the desired analyte(s) of interest. In some embodiments, the detection portion 110 can be used to obtain a predictable volume each time, because the volume of the recesses 136 of the detection portion 110 are constant. In some embodiments, a more concentrated initial sample 152' can be added to the second container 104, and the constant volume/size of the recesses 136 of the detection portion 110 can be used to obtain a known number or amount of one or more analytes of interest, for example, a known cell population of a given microorganism of interest. The recesses 136 of the detection portion 110 will be now described in greater detail.

Returning to FIG. 6, the one or more recesses 136 can be formed in the inner surface 120 (see FIG. 3) of the detection portion 110 and/or the one or more recesses 136 can be formed in a substrate (e.g., the substrate 190, or another insert or film) that can be coupled to (e.g., positioned against) at least a portion of the inner surface 120 of the detection portion 110 and positioned within the second container 104. In embodiments employing a substrate (or film), the thickness of the substrate can be at least about 25 micrometers, in some embodiments, at least about 100 micrometers, and in some embodiments, at least about 400 micrometers. In some embodiments, the thickness of the substrate can be no greater than about 2000 micrometers, in some embodiments, no greater than about 1000 micrometers, and in some embodiments, no greater than about 250 micrometers. For example, in some embodiments, the substrate can be a film that can be formed of a variety of suitable materials, including but not limited to including but not limited to a polyolefin (e.g., polyethylene), polyethylene terephthalate, polycarbonate, other suitable film materials, and combinations thereof.

Figure 3A:
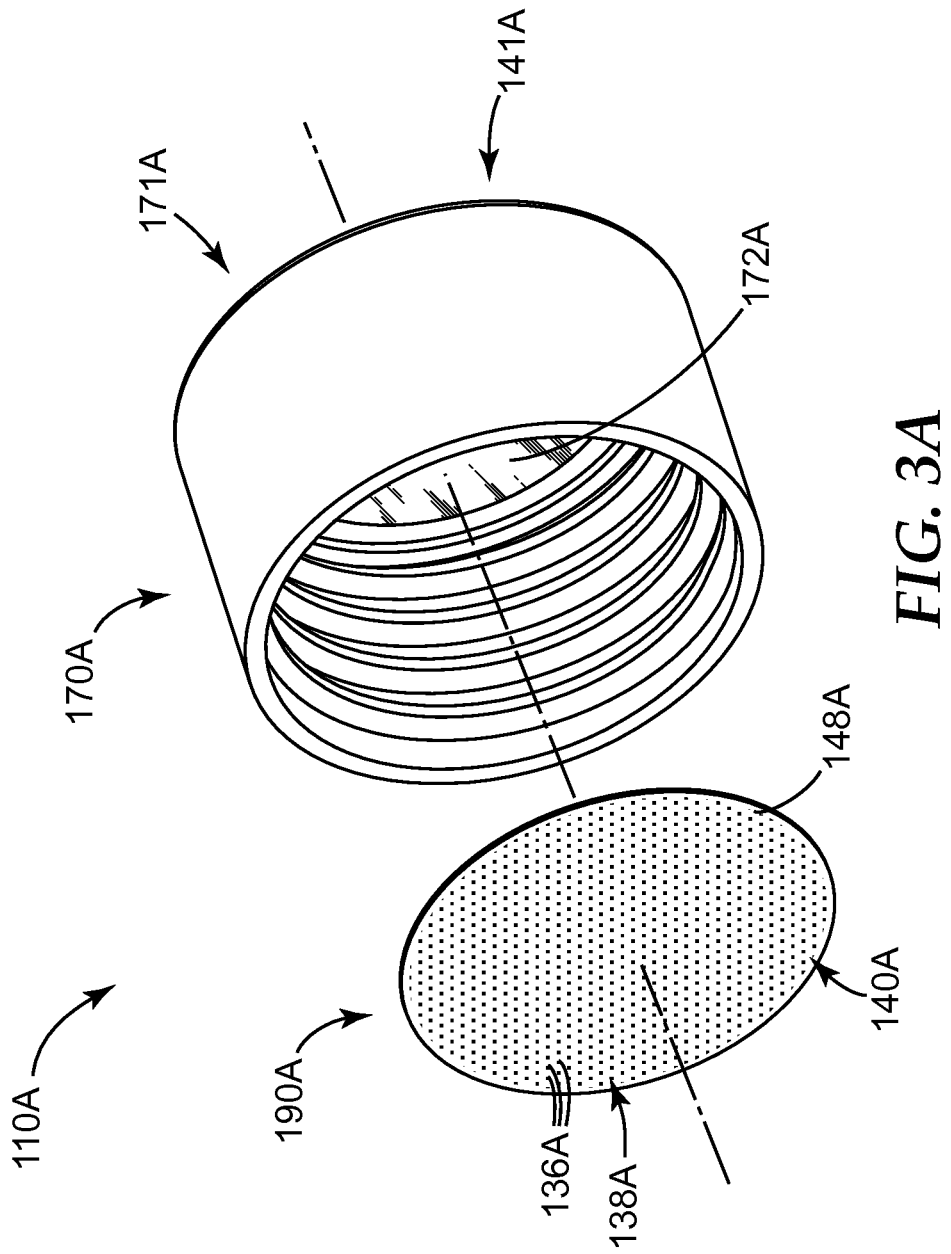
FIG. 3A is an exploded perspective view of a detection portion according to another embodiment of the present disclosure.

FIG. 3A shows an alternative detection portion 110A that can be employed in the systems and methods of the present disclosure. The detection portion 110A includes a detection housing 170A and substrate 190A formed of a film, and is relatively thinner than the substrate 190 of FIG. 3. The substrate 190A can be positioned against a first closed end 171A of the detection housing 170A. By way of example only, the first closed end 171A is shown as being substantially transparent, and particularly, as including an optical window 172A that is substantially transparent and will be at least partially overlapping and coextensive with a microstructured surface 138A when the substrate 190A is positioned against the optical window 172A. The microstructured surface 138A includes recesses 136A configured to retain a concentrate of a sample of interest. In addition, at least a portion of the substrate 190A can be substantially transparent. For example, as mentioned above, in some embodiments, the recesses 136A formed in a first major surface 148A of the substrate 190A can include at least bases that are substantially transparent, such that the contents of the recesses 136A can be visible through the bases and the first end 171A (e.g., via the optical window 172A) from a second side 141A of the detection portion 110A. Alternatively, however, in some embodiments, the detection portion 110A need not include any substantially transparent portions, and a concentrate retained in the recesses 136A can be interrogated from a first side 140A of the detection portion 110A (or of the substrate 190A).

FIG. 6 illustrates the recesses 136 according to one embodiment of the present disclosure. In the embodiment illustrated in FIGS. 1 and 2, the recesses 136, which can be wells and/or channels) are defined at least partially by a plurality of walls 142. In embodiments in which the recesses 136 include wells, the plurality of walls 142 can include a plurality of intersecting walls 142.

In some embodiments, the one or more recesses 136 are microstructured recesses 136 and define the microstructured surface 138. In such embodiments, the microstructured surface 138 can be formed by a variety of methods, including a variety of microreplication methods, including, but not limited to, casting, coating, molding, and/or compressing techniques, other suitable techniques, or combinations thereof. For example, microstructuring of the microstructured surface 138 can be achieved by at least one of (1) casting a molten thermoplastic using a tool having a microstructured pattern, (2) coating of a fluid onto a tool having a microstructured pattern, solidifying the fluid, and removing the resulting film, and/or (3) passing a thermoplastic film through a nip roll to compress against a tool (e.g., male tooling) having a microstructured pattern (i.e., embossing). The tool can be formed using any of a number of techniques known to those skilled in the art, selected depending in part upon the tool material and features of the desired topography. Other suitable techniques include etching (e.g., chemical etching, mechanical etching, ion etching, etc., and combinations thereof), ablation (e.g., laser ablation, etc.), photolithography, stereolithography, micromachining, knurling (e.g., cutting knurling or acid enhanced knurling), scoring, cutting, etc., or combinations thereof.

Alternative methods of forming the microstructured surface 138 include thermoplastic extrusion, curable fluid coating methods, and embossing thermoplastic layers, which can also be cured. Additional information regarding the substrate or film material and various processes for forming the microstructured surface 138 can be found, for example, in Halverson et al., PCT Publication No. WO 2007/070310 and US Publication No. US 2007/0134784; Hanschen et al., US Publication No. US 2003/0235677; Graham et al., PCT Publication No. WO2004/000569; Ylitalo et al., U.S. Pat. No. 6,386,699; and Johnston et al., US Publication No. US 2002/0128578 and U.S. Pat. No. 6,420,622, U.S. Pat. No. 6,867,342, and U.S. Pat. No. 7,223,364, each of which is incorporated herein by reference.

With microreplication, the microstructured surface 138 can be mass produced without substantial variation from product-to-product and without using relatively complicated processing techniques. In some embodiments, microreplication can produce a microstructured surface that retains an individual feature fidelity during and after manufacture, from product-to-product, that varies by no more than about 50 micrometers. In some embodiments, the microstructured surface 138 retains an individual feature fidelity during and after manufacture, from product-to-product, which varies by no more than 25 micrometers. In some embodiments, the microstructured surface 138 comprises a topography (i.e., the surface features of an object, place or region thereof) that has an individual feature fidelity that is maintained with a resolution of between about 50 micrometers and 0.05 micrometers, and in some embodiments, between about 25 micrometers and 1 micrometer.

The recesses 136 are adapted to retain the concentrate 154 resulting from the centrifugation step illustrated in FIG. 5, and described above. Each recess 136 is shown in FIG. 6 as having a generally rectangular cross-sectional shape and as being formed by at least two walls 142 and a base or closed end 146, and each recess 136 is separated from an adjacent recess 136 by a wall 142. Each recess 136 also includes an open end or opening 147. It should be understood that the recesses 136 can include a variety of shapes, as long as the recesses 136 are defined in the inner surface 120 of the detection portion 110 and/or a substrate adapted to be coupled to the inner surface 120 (or the detection housing 170), so as to be able to retain the concentrate 154. Said another way, each recess 136 can be shaped and dimensioned to provide a reservoir, or well, for the concentrate 154.

Figure 9:
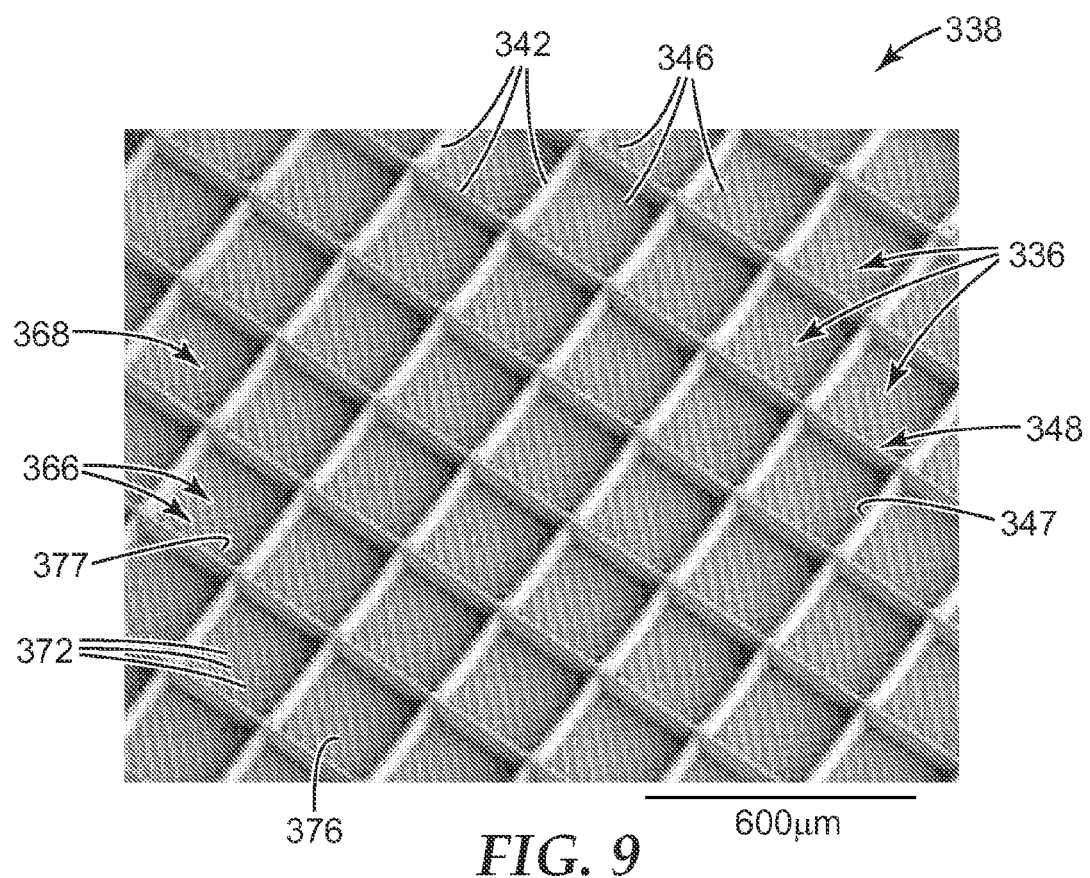
FIGS. 9-17 are optical micrographs of microstructured surfaces according to various embodiments of the present disclosure.
Figure 10:
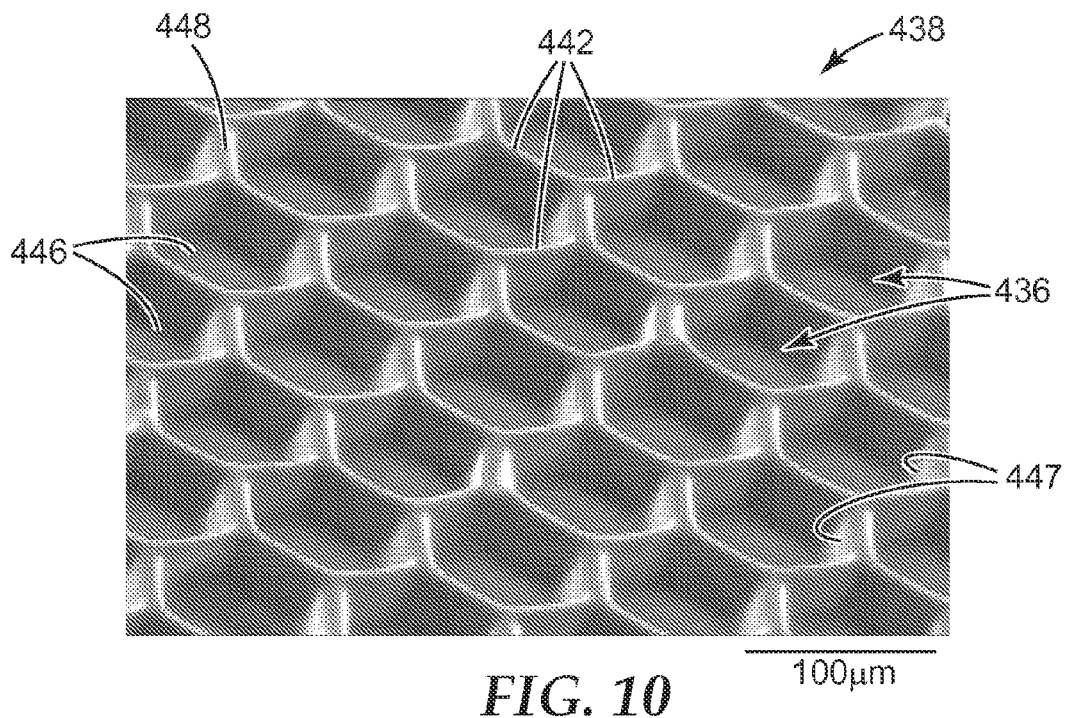

Whether the recesses 136 include wells, depression, channels or a combination thereof, examples of suitable recess shapes can include, but are not limited to, a variety of polyhedral shapes, parallelepipeds (e.g., as shown in FIGS. 6 and 9), prismatoids, prismoids, etc., and combinations thereof. For example, the recesses 136 can be polyhedral, conical, frusto-conical, pyramidal, frusto-pyramidal, spherical, partially spherical, hemispherical, ellipsoidal, dome-shaped, cylindrical, cube-corner shaped (e.g., see the tool in FIG. 20 that can be used to form cube-corner shaped recesses), other suitable shapes, and combinations thereof. Furthermore, the recesses 136 can have a variety of cross-sectional shapes (including a vertical cross-section as shown in FIG. 6, a horizontal cross-section, or a combination thereof), including, but not limited to, at least one of parallelograms, parallelograms with rounded corners, rectangles, squares, circles, half-circles, ellipses, half-ellipses, triangles, trapezoids, stars, other polygons (e.g., hexagons, as shown in FIG. 10), other suitable cross-sectional shapes, and combinations thereof.

In some embodiments, the recesses 136 are shaped to include edges or corners. Such edges or corners can facilitate the retention of the concentrate 154 in the recesses 136 and can inhibit the concentrate 154 from being removed from the recesses 136 under normal gravitational forces. For example, in embodiments in which the concentrate 154 has a high surface energy, or in which the concentrate 154 includes molecules that are attracted to those of the material making up the inner surface 120 of the detection portion 110 or the substrate 190 in which the recesses 136 are formed, the concentrate 154 can be preferentially attracted to edges and/or corners of the recesses 136 (i.e., where the concentrate 154 can remain in contact with two or more surfaces), rather than smooth single surfaces.

In the embodiment illustrated in FIG. 6, the base 146 of each recess 136 is flat and planar (i.e., has an area), and is substantially parallel to the first major surface 148. However, because other shapes of recesses 136 are possible, the base 146 need not be planar, but rather can include a point or a line that is spaced the greatest distance from the first major surface 148. For example, in embodiments employing one or more hemispherical recesses 136, the base 146 of such recesses 136 can include the point in the hemisphere that is spaced the greatest distance from the first major surface 148. In addition, even in embodiments employing a planar base 146, the base 146 need not be entirely flat, but rather can be at least partially curved, flat, or a combination thereof. Furthermore, even in embodiments employing a flat, planar base 146, the base 146 need not be parallel to the first major surface 148, but rather can be oriented at an angle (e.g., a non-zero angle) with respect to the first major surface 148.

Furthermore, in the embodiment illustrated in FIG. 6, the recesses 136 are each shown as having various lines of symmetry, and the base 146 is centered with respect to the opening 147 of the recess 136. However, it should be understood that the recesses 136 need not include any lines of symmetry, and the base 146 (whether the base 146 includes a point, a line or an area) need not be centered with respect to the opening 147 of the recess 136.

The recesses 136 illustrated in FIG. 6 are shown by way of example only as being of the same size and shape; however, it should be understood that all of the recesses 136 do not need to be of the same size or shape. That is, the recesses 136 can all be formed of about the same shape and size, the same or similar shape but different sizes, different shapes but similar sizes, different shapes and sizes, or a combination thereof. For example, in some embodiments, the recesses 136 can include a pattern of alternating sizes of similarly-shaped recesses 136, or regions of recesses 136 wherein the recesses 136 of one region are of the same size (or shape) but are not of the same size (or shape) as an adjacent region, and the like, and combinations thereof.

Furthermore, the recesses 136 illustrated in FIG. 6 are shown by way of example only as being regularly arranged (e.g., in a cellular array in embodiments in which the recesses 136 include wells). However, it should be understood that the recesses 136 can include a variety of regular arrangements or arrays, random arrangements, or combinations thereof. In some embodiments, the recesses 136 are arranged randomly on a local or smaller scale, but the random arrangements repeat, or are ordered, on a larger scale. Alternatively, in some embodiments, the recesses 136 are ordered on a smaller scale, but the ordered regions are randomly arranged on a larger scale.

In addition, in the embodiment illustrated in FIG. 6, the walls 142 are all of the same size and shape. However, it should be understood that a variety of other wall shapes are possible. For example, the walls 142 need not include a substantially rectangular cross-sectional shape, but rather can include any of the above-described cross-sectional shapes.

The walls 142 and the recesses 136 can be characterized by a variety of sizes, dimensions, distances between walls 142 or recesses 136, relative sizes, etc. The walls 142 generally have dimensions such as thickness, height, length, width, etc. The recesses 136 generally have volumes with dimensions such as a radius, diameter, height, width, length, etc. Generally, the walls 142 and/or the recesses 136 are sized, shaped and spaced to retain the concentrate 154 in the recesses 136 when detection portion 110 is in any orientation (e.g., by capillary forces).

In some embodiments, the walls 142 can have an average thickness of at least about 1 micrometer, in some embodiments, at least about 5 micrometers, and in some embodiments, at least about 10 micrometers. In some embodiments, the walls 142 can have an average thickness of no greater than about 50 micrometers, in some embodiments, no greater than about 30 micrometers, and in some embodiments, no greater than about 20 micrometers.

In some embodiments, the walls 142 can be shaped and/or sized to minimize the area of the top surface of the walls 142 so that any matter collected on the top surface of the walls 142 can be diverted into an adjacent recess 136. For example, in some embodiments, the walls 142 can include a taper toward the top surface. In some embodiments, the top surface can include a convex shape. In some embodiments, a combination of a taper and a convex shape can be employed. In some embodiments, the top surface is not radiused, but rather is flat; however, the top surface defining the openings 147 of the recesses 136 are smooth with little to no sharp edges.

In some embodiments, the configuration of the walls 142 and the recesses 136 in any given region can be chosen such that the average wall or recess pitch P (i.e., the center to center distance between adjacent walls 142 or recesses 136, respectively) is at least about 1 micrometer, in some embodiments, at least about 10 micrometers, and in some embodiments, at least about 50 micrometers. In some embodiments, the average wall or recess pitch P is no greater than about 1000 micrometers, in some embodiments, no greater than about 800 micrometers, in some embodiments, no greater than about 600 micrometers, in some embodiments, no greater than about 500 micrometers, in some embodiments, no greater than about 200 micrometers, in some embodiments, no greater than about 150 micrometers, and in some embodiments, no greater than about 100 micrometers. In some embodiments, the pitch P can range from 50 micrometers to 850 micrometers.

In some embodiments, the recesses 136 can be packed more densely on the first major surface 148 than in others. The higher the packing density of the recesses 136 (e.g., referred to as average recess density or average well density), generally, the more concentrate 154 a given area of the first side 140 of the detection portion 110 can contain. Also, in some embodiments, if the microstructured surface 138 includes more land area between recesses 136, it is possible that the denser portions of the sample (e.g., comprising the analyte of interest) can be centrifuged onto a land area and then may tend to get carried away with the supernatant when the container is inverted. Therefore, in general, higher recess densities on the microstructured surface 138 would be preferred to afford a higher likelihood of capture.

In some embodiments, the average recess density is at least about 20 recesses/cm$^2$, in some embodiments, at least about 30 recesses/cm$^2$, in some embodiments, at least about 70 recesses/cm$^2$, in some embodiments, at least about 100 recesses/cm$^2$, in some embodiments, at least about 150 recesses/cm$^2$, in some embodiments, at least about 200 recesses/cm$^2$, in some embodiments, at least about 500 recesses/cm$^2$, in some embodiments, at least about 800 recesses/cm$^2$, in some embodiments, at least about 900 recesses/cm$^2$, in some embodiments, at least about 1000 recesses/cm$^2$, in some embodiments, at least about 2000 recesses/cm$^2$, and in some embodiments, at least about 3000 recesses/cm$^2$. In some embodiments, the recess density can be about 825 recesses/cm$^2$.

In some embodiments, the recesses 136 can be characterized by an x-direction dimension in the plane of the first major surface 148 (e.g., a length, a width, a radius, a diameter, a diagonal, etc.). The phrase "in the plane of" is used to generally refer to an x-y plane dimension, and is only used to distinguish from a depth or a z-direction dimension, but does not require the dimension to be located exactly in the plane of the first major surface 148, but rather can include dimensions that lie in other similar x-y planes that are substantially parallel to the plane of the first major surface 148. In some embodiments, the average recess x-direction (or y-direction) dimension (e.g., the width of the base 146) is at least about 1 micrometer, in some embodiments, at least about 10 micrometers, and in some embodiments, at least about 50 micrometers. In some embodiments, the average recess x-direction dimension is less than about 1000 micrometers, in some embodiments, less than about 500 micrometers, and in some embodiments, less than about 100 micrometers.

In some embodiments, the average recess volume is at least about 1 picoliter (pL), in some embodiments, at least about 10 pL, in some embodiments, at least about 100 pL, and in some embodiments, at least about 1000 pL (1 nL). In some embodiments, the average recess volume is no greater than about 1,000,000 pL (1 µL), in some embodiments, no greater than about 100,000 pL, in some embodiments, no greater than about 10,000 pL. In some embodiments, the average recess volume ranges from 10 nL (10,000 pL) to 100 nL (100,000 pL).

Another way to characterize the walls 142 and the recesses 136 is to describe them in terms of their aspect ratios, as described above. An "aspect ratio" of a recess 136 is the ratio of the depth of a recess 136 to the width of the recess 136. An "aspect ratio" of a wall 142 is the ratio of the height of the wall 142 to the width (or thickness) of the wall 142. The aspect ratios of the recesses 136 and/or the walls 142 can include those described above.

In some embodiments, the average wall aspect ratio is at least about 0.01, in some embodiments, at least about 0.05, and in some embodiments, at least about 1. In some embodiments, the average wall aspect ratio is no greater than about 15, in some embodiments, no greater than about 10, and in some embodiments, no greater than about 8.

In some embodiments, the average height of the walls 142 or the average depth of the recesses 136 (i.e., the distance between the closed end, or base, 146 of the recess 136 and the open end, or opening, 147 of the recess 136, i.e., the adjacent portion of the first major surface 148) is at least about 5 micrometers, in some embodiments, at least about 20 micrometers, and in some embodiments, at least about 30 micrometers. In some embodiments, the average height of the walls 142 or the average depth of the recesses 136 can be no greater than about 1000 micrometers, in some embodiments, no greater than about 250 micrometers, in some embodiments, no greater than about 100 micrometers, and in some embodiments, no greater than about 50 micrometers. In the embodiment illustrated in FIG. 6, the wall height is substantially the same as the recess depth; however, it should be understood that this need not be the case. For example, in some embodiments, the recesses 136 include a portion that is recessed even below the bottom of the walls 142, such that the well depth is greater than the wall height. However, even in such embodiments, the above size ranges can apply.

Figure 18A:
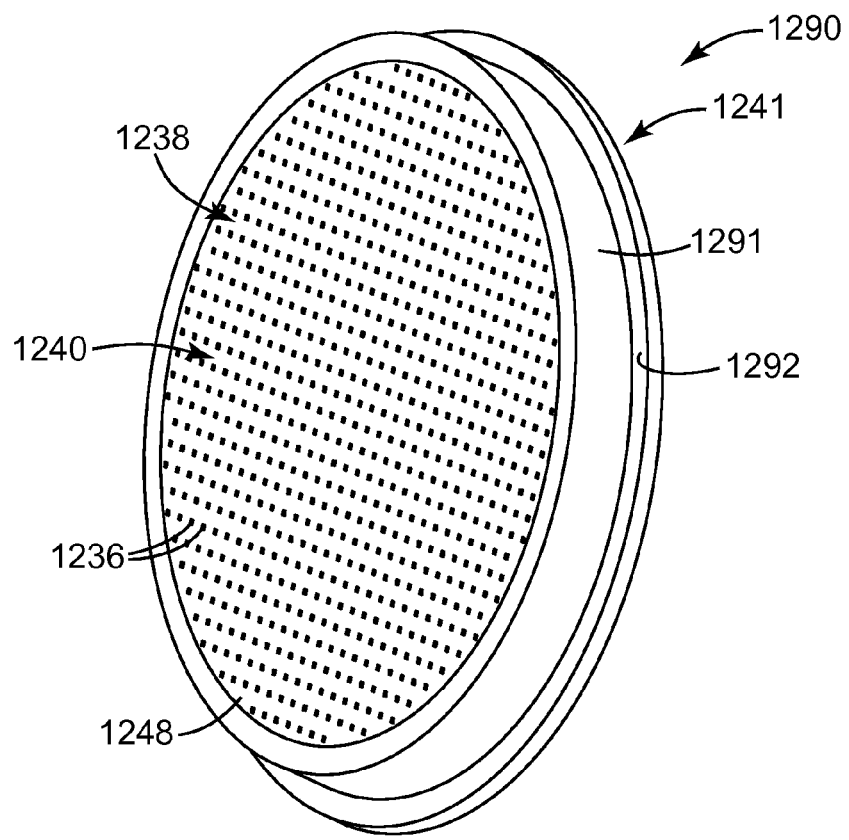
FIG. 18A is a perspective view of a substrate comprising a microstructured surface according to one embodiment of the present disclosure.
Figure 18B:
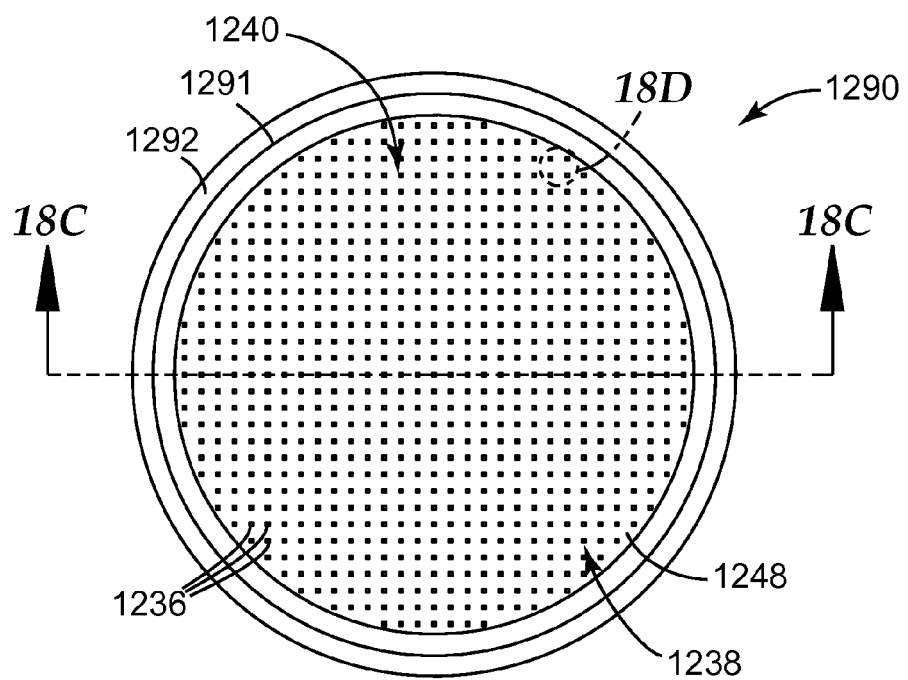
FIG. 18B is a top plan view of the substrate of FIG. 18A.
Figure 18C:
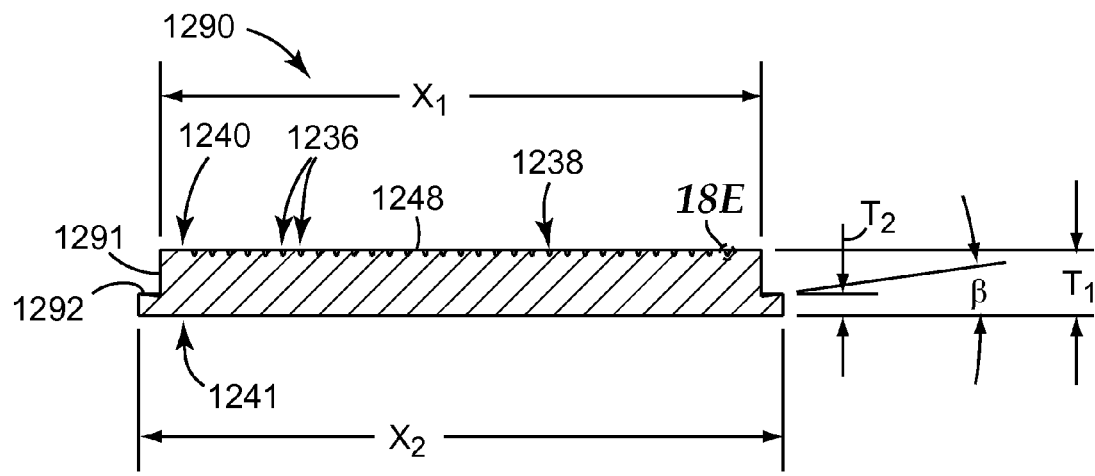
FIG. 18C is a side cross-sectional view of the substrate of FIGS. 18A and 18B, taken along line 18C-18C of FIG. 18B.
Figure 18D:
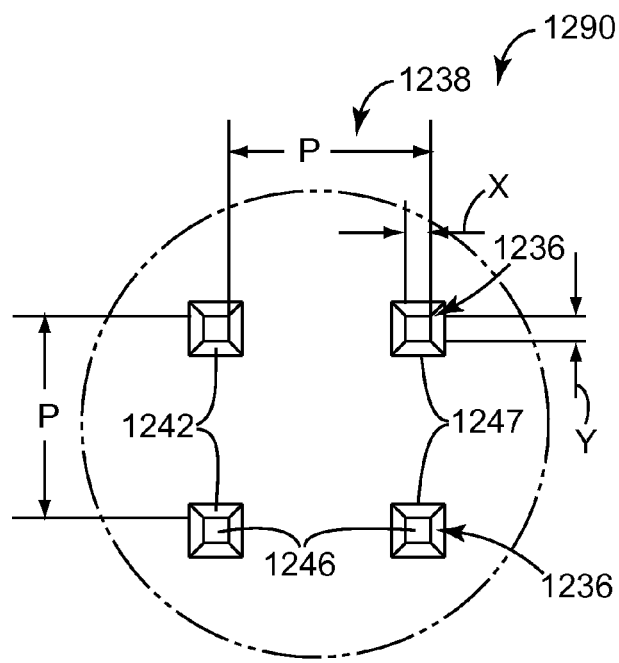
FIG. 18D is a close-up top plan view of the substrate of FIGS. 18A-18C, taken of the area labeled 18D in FIG. 18B.
Figure 18E:
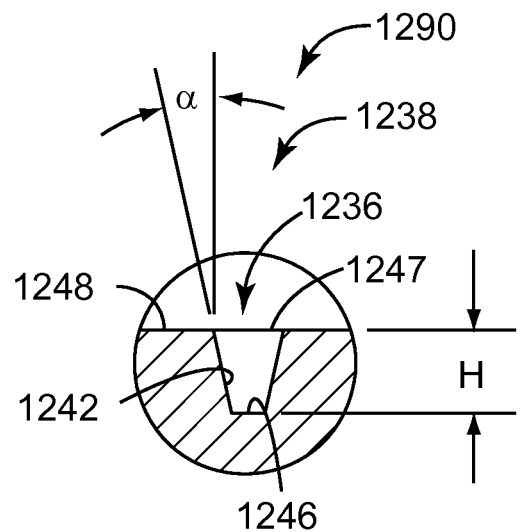
FIG. 18E is a close-up side cross-sectional view of the substrate of FIGS. 18A-18D, taken of the area labeled 18E in FIG. 18C.

In some embodiments, unlike the embodiment shown in FIG. 6, the recesses 136 can include a draft angle, such that the walls 142 are oriented at a non-zero and non-right angle with respect to the respective base(s) 146 (see, e.g., FIG. 18E). In some embodiments, the draft angle can be reported as the angle between a wall 142 of the recess 136 and a vertical (i.e., a line or plane that is perpendicular or normal to a flat base 146), as shown in FIG. 18E, for example. In some embodiments, the draft angle can be at least about 5 degrees, in some embodiments, at least about 10 degrees, and in some embodiments, at least about 15 degrees. In some embodiments, the draft angle is no greater than about 50 degrees, in some embodiments, no greater than about 30 degrees, in some embodiments, no greater than about 25 degrees, and in some embodiments, no greater than about 20 degrees. In some embodiments, the draft angle ranges from about 20 degrees to about 25 degrees.

Whether or not the recesses 136 or the walls 142 are themselves microstructured, the detection portion 110 can include a microstructured surface 138 that includes additional microstructured features, such as protrusions, depressions or recesses, or a combination thereof. At least some of the microstructured features can be formed on a nano-, micro- or macro-scale. Each microstructured feature can be defined by two or more dimensions (e.g., one or more dimensions into/out of the plane of the first major surface 148 and one or more dimensions in the plane of the first major surface 148). In some embodiments, the first major surface 148 includes a configuration of microstructured features, such that at least two dimensions of each of the features are microscopic. The "features" can include any of the above-described microstructured features formed in the first major surface 148, including the walls 142, the recesses 136, or any other microstructured features formed on the first major surface 148.

The microstructured features can have a desired characteristic size (e.g., length, width, depth, radius, diameter, or other dimension measured along any direction) and density (e.g., features per unit area of the first major surface 148). A feature can be configured such that its characteristic length in all three directions (e.g., x, y (in the plane of the first major surface 148) and z (into/out of the plane of the first major surface 148)) is similar. Alternatively, a feature can be configured such that the characteristic length in one or more directions is greater than in the other directions.

In some embodiments, a feature can have a maximum characteristic length in one or more dimensions of no greater than about 500 micrometers. In some embodiments, the maximum characteristic length is 50 micrometers, and in some embodiments, the maximum characteristic length is 10 micrometers. In some embodiments, the minimum characteristic length in one or more dimensions is 1 nanometer. In some embodiments, the minimum characteristic length is 10 nanometers, and in some embodiments, the minimum characteristic length is 100 nanometers. Furthermore, in some embodiments, the feature density is at least 100 features per square millimeter ($mm^2$), in some embodiments, at least 1,000 features per $mm^2$, and in some embodiments, at least 10,000 features per $mm^2$.

Other embodiments of microstructures surfaces that can be employed with the systems and methods of the present disclosure will be described in greater detail below with reference to FIGS. 9-19H.

Figure 7:
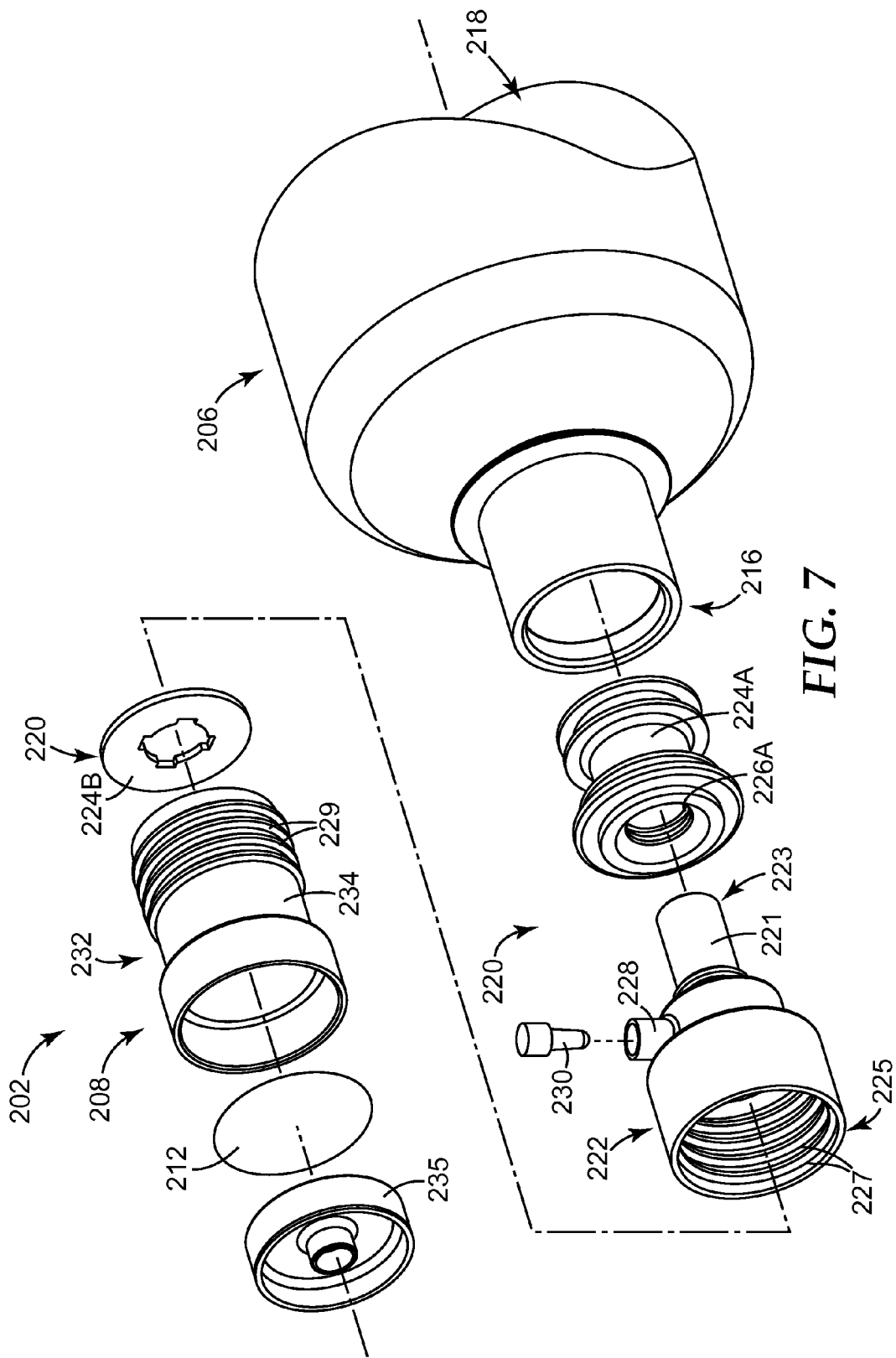
FIG. 7 is an exploded perspective view of a first container according to another embodiment of the present disclosure.
Figure 8:
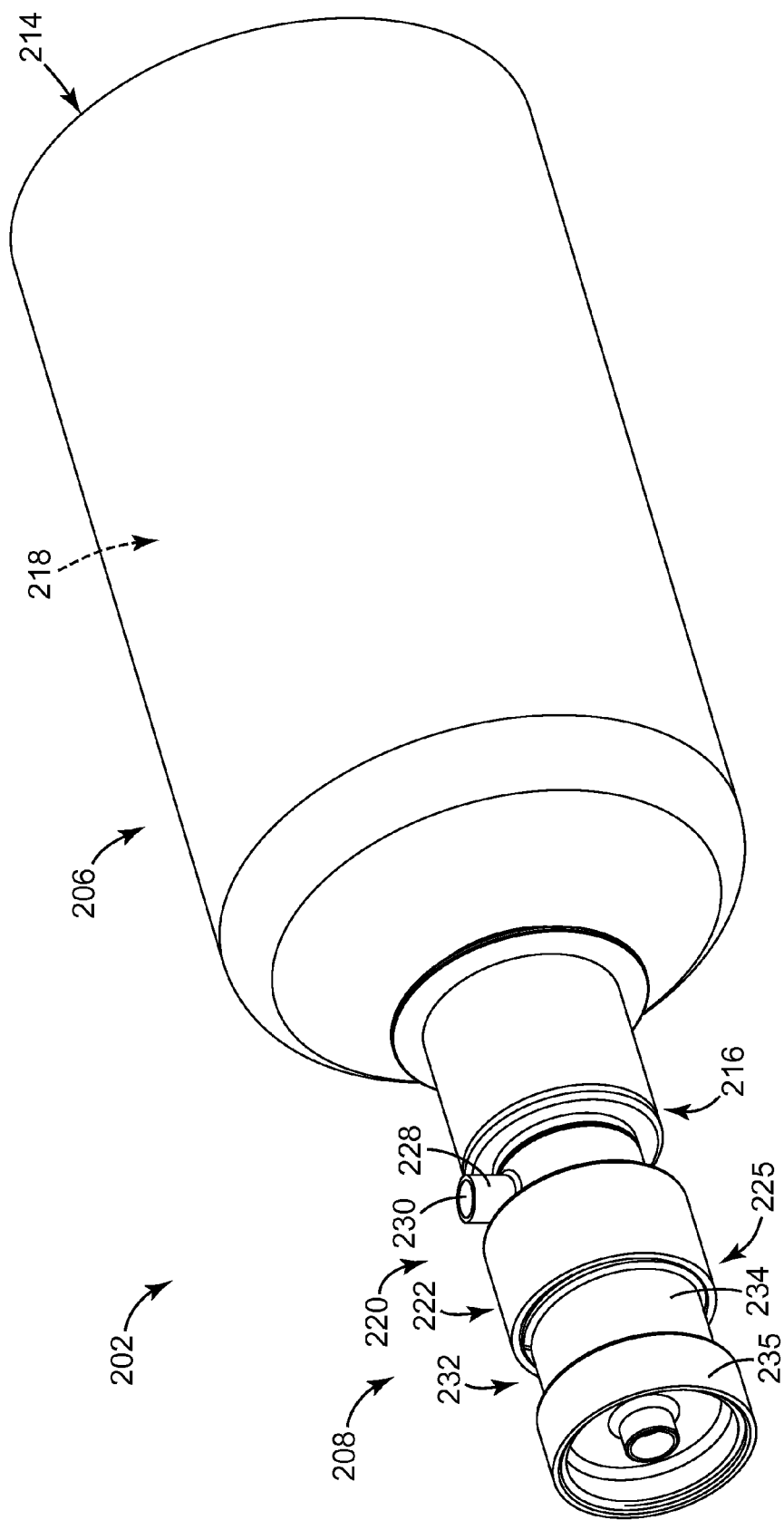
FIG. 8 is an assembled perspective view of the first container of FIG. 7.

FIGS. 7 and 8 illustrate a first container 202 according to another embodiment of the present disclosure that can be employed in systems and methods of the present disclosure (e.g., in the sample detection systems of FIGS. 1-4 and 6 and the sample detection method of FIG. 5). The first container 202 shares many of the same elements and features described above with reference to the illustrated embodiment of FIGS. 1 and 2. Accordingly, elements and features corresponding to the elements and features of the illustrated embodiment of FIGS. 1 and 2 are provided with the same reference numerals in the 200 series. Reference is made to the description above accompanying FIGS. 1-2 for a more complete description of the features and elements (and alternatives to such features and elements) of the embodiment illustrated in FIGS. 7 and 8.

As shown in FIGS. 7 and 8, the first container 202 can include a receptacle portion (or "first portion") 206 that is adapted to contain a sample and a filter portion (or "second portion") 208 that includes a filter 212 that can be configured to retain an analyte of interest from the sample, if present. The filter portion 208 and the receptacle portion 206 can be configured to be removably coupled together to form the first container 202.

The filter portion 208 can be substantially the same as that of the filter portion 108, and can include a filter housing 232 and a filter 212 dimensioned to be received and retained within the filter housing 132. Particularly, the filter housing 232 can include a tube 234 and a base 235.

In general, the first container 202 can be used to filter a sample by passing the sample through the filter portion 208, and particularly, through the filter 212 to form a filtrate and a filtrand of the sample, as described above. The filter portion 208 can then be removed from the receptacle portion 206 of the first container 202 and coupled to a detection portion (e.g., the detection portion 110) to form a second container (e.g., the second container 104).

The receptacle portion 206 can include a first end 214 that at least partially defines a reservoir 218, and a second end 216 configured to be coupled to the filter portion 208 (i.e., either directly or indirectly). The first end 214 can either be an open end or a closed end. By way of example only, in FIG. 8, the first end 214 is closed, and the second end 216 is open, such that a sample can be added to the reservoir 218 via the second end 216. In such embodiments, a sample can be added to the reservoir 218 prior to coupling the receptacle portion 206 to the filter portion 208 for the filtration step.

As shown in FIG. 7, the first container 202 can further include a filter connection assembly 220 for coupling the filter portion 208 and the receptacle portion 206 together. The filter connection assembly 220 of FIGS. 7 and 8 is shown as being adapted to be coupled between the receptacle portion 206 and the filter portion 208, rather than being integrally formed with the receptacle portion 206.

As shown in FIGS. 7 and 8, in some embodiments, the filter connection assembly 220 can include a connector 222, a first gasket 224A, and a second gasket 224B.

The connector 222 can include a first end 223 configured to be coupled to the receptacle portion 206 (e.g., via the first gasket 224A) and a second end 225 configured to be coupled to the filter portion 208. By way of example only, the second end 225 is shown as including threads 227 that cooperate and engage with threads 229 of the filter portion 208 to allow the filter portion 208 to be screwed onto the filter connection assembly 220 for coupling to the filter connection assembly 220 and the receptacle portion 206.

As shown in FIGS. 7 and 8, the filter connection assembly 220 (e.g., the connector 222) can further include a vent port 228 and a filter plug 230 that can serve as an air inlet during the filtration process, particularly, in embodiments in which the first end 214 of the receptacle portion 206 is closed. The filter plug 230 can be used to filter inlet air as it enters the first container 202 during a filtration process.

The second gasket 224B can be substantially the same as the gasket 124 of FIG. 1, and both gaskets 224A and 224B can be used to seal the interior of the first container 202 from ambience, while maintaining fluid communication between the receptacle portion 206 and the filter portion 208. The second gasket 224B can be configured to fit within the connector 222 to aid in creating a seal between the receptacle portion 206 and the filter portion 208, for example, by creating a seal between the connector 222 and the filter housing 232.

The first gasket 224A can be configured to aid in coupling and sealing the connector 222 to the second (open) end 216 of the receptacle portion 206. As shown, the first gasket 224A can be shaped and dimensioned to couple a first end 223 of the connector 222 to the second end 216 of the receptacle portion 206. Particularly, as shown in FIG. 7, the first gasket 224A can be shaped and dimensioned to be received in the second (open) end 216 of the receptacle portion 206 and to receive the first end 223 of the connector 222. For example, the first gasket 224A can include an aperture or bore 226A formed therethrough that is shaped and dimensioned to receive the first end 223 of the connector 222, and particularly, to receive a connection tube 221 of the connector 222. The shape and configuration of the first gasket 224A, the connector 222, and the second end 216 of the receptacle portion 216 are shown by way of example only; however, it should be understood that any shapes and configurations and relative structures of these elements can be employed to achieve the same function.

FIG. 9 illustrates an exemplary microstructured surface 338 according to another embodiment of the present disclosure, employing primary and secondary microstructured features. The microstructured surface 338 shares many of the same elements and features described above with reference to the illustrated embodiment of FIG. 6. Accordingly, elements and features corresponding to the elements and features of the illustrated embodiment of FIG. 9 are provided with the same reference numerals in the 300 series. Reference is made to the description above accompanying FIG. 6 for a more complete description of the features and elements (and alternatives to such features and elements) of the embodiment illustrated in FIG. 9.

The microstructured surface 338 includes first major surface 348 defined at least partially by a plurality of primary intersecting walls 342, and particularly, by an upper surface of the plurality of primary intersecting walls 342. The major surface 348 can also be referred to as the "primary microstructured surface" 348. The primary microstructured surface 348 includes a plurality of primary recesses 376 (i.e., which are defined as wells in FIG. 9) that are each defined at least partially by four primary walls 342, a primary base or closed end 346, and a primary opening or open end 347.

The microstructured surface 338 further includes a second level or degree of microstructures. Particularly, the microstructured surface 338 includes a secondary major surface 368, which can also be referred to as a "secondary microstructured surface" 368. The secondary microstructured surface 368 is defined at least partially by a plurality of secondary intersecting walls 372, and particularly, by an upper surface of the plurality of secondary intersecting walls 372. In the embodiment illustrated in FIG. 9, the upper surfaces of the plurality of secondary walls 372 are spaced a distance from the major surface 348, such that the secondary walls 372 are recessed relative to the major surface 348 of the microstructured surface 338.

The secondary microstructured surface 368 is further defined by a plurality of secondary recesses 366 (i.e., which are defined as wells in FIG. 9) that are each at least partially defined by four secondary walls 372, a secondary base or closed end 376, and a secondary opening or open end 377. The secondary base 376 is spaced a distance from the primary microstructured surface 348, and is spaced a distance from the secondary microstructured surface 368. In the embodiment illustrated in FIG. 9, the primary bases 346 are each at least partially defined by the plurality of secondary bases 376, and the secondary bases 376 are positioned the same distance from the primary microstructured surface 348 as the primary bases 346. However, it should be understood that the secondary bases 376 need not be positioned at the same depth as the primary bases 246, but rather, the secondary bases 376 can be positioned an additional distance from the primary microstructured surface 348 and can be spaced a distance from the respective primary base 346 as well. For example, in some embodiments, one or more of the primary recesses 336 can include one or more secondary recesses 366 positioned such that the secondary recess(es) 366 define a stepped configuration between the primary base 346 and the secondary base 376.

A concentrate can be positioned in the microstructured recesses 336, 366 of the microstructured surface 338, and particularly, in the secondary recesses 366. That is, each primary recess 336 and each secondary recess 366 is adapted to retain the concentrate. In the embodiment illustrated in FIG. 9, the secondary walls 372 are illustrated as being shorter than the primary walls 342; however, it should be understood that the secondary walls 372 can instead be as tall as (or more similarly sized relative to) the primary walls 342. In embodiments employing shorter secondary walls 372, the concentrate can be allowed to overfill the secondary recesses 366 and still be retained in the microstructured surface 338.

The embodiment illustrated in FIG. 9 includes two levels or degrees of microstructuring by way of example only. However, additional degrees of microstructuring in can further enhance the retention of the concentrate in the microstructured surface 238. Such additional degrees of microstructuring can include additional tertiary microstructures, quaternary microstructures, and so on. Each additional level of microstructuring can go increasingly deeper into the major surface 348 (e.g., provided by a second portion such as the second portion 104, 204 and/or a substrate in which the microstructured surface 338 is defined), and the additional wells formed can have bases spaced the same distance from the primary microstructured surface 348 as the primary bases 346, a different distance, or a combination thereof.

The microstructured surface 338 of FIG. 9 shows primary recesses 336, and a plurality of secondary recesses 366 in each of the primary recesses 336. However, it should be understood that a variety of regular configurations, random configurations, or combination configurations are possible. For example, in some embodiments, random primary recesses 336 can include secondary recesses 366, or every other primary recess 336 can include secondary recesses 366, or some regions of the microstructured surface 338 can include primary and secondary recesses 336 and 366, while some regions of the microstructured surface 338 include only primary recesses 336, etc.

In the embodiment illustrated in FIG. 9, the secondary walls 372 are oriented at an angle of about 45 degrees with respect to the primary walls 342. However, it should be understood that the secondary walls 372 can instead be oriented at a variety of other angles (e.g., 0 degrees, 90 degrees, etc.) with respect to the primary walls 342. In addition, the secondary recesses 366 are illustrated as having the same shape as that of the primary recesses 336; however, it should be understood that all of the alternatives described above with respect to the recesses 136 of FIG. 9 regarding shape, number, orientation, size, etc. apply to the primary recesses 336 and the secondary recesses 366 of the microstructured surface 338 of FIG. 9.

The secondary walls 372 and recesses 366 can range in size and can be defined by the size ranges given above with respect to the walls 142 and recesses 136 of FIG. 6. Furthermore, in some embodiments, the secondary recesses 366 can have an average depth or the secondary walls 372 can have an average height of at least about 0.1 micrometers, in some embodiments, at least about 1 micrometers, and in some embodiments, at least about 2 micrometers. In some embodiments, the secondary recesses 366 can have an average depth or the secondary walls 372 can have an average height of no greater than about 50 micrometers, in some embodiments, no greater than about 20 micrometers, in some embodiments, no greater than about 10 micrometers, and in some embodiments, no greater than about 5 micrometers.

The secondary walls 372 and recesses 366 can be further defined by their relative sizes, as compared to the primary walls 342 and recesses 336. For example, in some embodiments, the average secondary wall height or the average secondary well depth is at least about 5 micrometers less than the average primary wall height or the average primary well depth, respectively. The average primary wall height and the average primary well depth, along with the other characteristics of the primary walls 342 and recesses 336 can be assumed to be the same as those described above with respect to the walls 142 and recesses 136 of FIG. 6. Furthermore, in some embodiments, the average secondary wall height or the average secondary well depth is at least about 20 micrometers less than the average primary wall height or the average primary well depth, respectively, in some embodiments, at least about 50 micrometers less, and in some embodiments, at least about 70 micrometers less.

In some embodiments, the ratio of the average primary well volume to the average secondary well volume is at least about 5, in some embodiments, at least about 30, in some embodiments, at least about 50, and in some embodiments, at least about 150. In some embodiments, the ratio of the average primary well volume to the average secondary well volume is no greater than about 2,000,000, in some embodiments, no greater than about 1,000,000, in some embodiments, no greater than about 150,000, and in some embodiments, no greater than about 500.

In one embodiment of the microstructured surface 338 of FIG. 9, the primary recesses 336 (which were in the form of wells) and primary walls 342 include a pitch (i.e., a center to center spacing between adjacent primary walls 342 or recesses 336, respectively) of about 250 micrometers. The primary recesses 336 are parallelipipedal in shape with a nominal depth of about 67 micrometers, and the primary walls 342 are oriented at a 45 degree angle with respect to the machine direction of the substrate. The primary wall height between the primary wall intersections is about 67 micrometers, and the primary wall height in the region of the intersections is about 75 micrometers. The secondary walls 372 are about 4 micrometers in height, and the secondary walls 372 and the secondary recesses 366 include a pitch (i.e., a center to center distance between adjacent secondary walls 372 or recesses 336, respectively) of about 25 micrometers. The secondary walls 372 are arranged such that they are either parallel or perpendicular to the machine direction of the substrate (i.e., the secondary walls 372 are arranged at an angle of about 45 degrees with respect to the primary walls 342). Additional details of the embodiments of the microstructured surface 338 and methods of making it are described in Halverson et al., PCT Publication No. WO 2007/070310, which is incorporated herein by reference.

FIGS. 10-17 each illustrate a microstructured surface 438, 538, 538, 738, 838, 938, 1038 and 1138, respectively, according to another embodiment of the present disclosure. The microstructured surfaces 438, 538, 538, 738, 838, 938, 1038 and 1138 share many of the same elements and features described above with reference to the illustrated embodiment of FIG. 6. Accordingly, elements and features corresponding to the elements and features of the illustrated embodiment of FIG. 6 are provided with the same reference numerals in the 400, 500, 600, 700, 800, 900, 1000 and 1100 series, respectively. Reference is made to the description above accompanying FIG. 6 for a more complete description of the features and elements (and alternatives to such features and elements) of the embodiments illustrated in FIGS. 10-17.

As shown in FIG. 10, the microstructured surface 438 includes a plurality of recesses 436 formed in a first major surface 448 and adapted to retain a concentrate of a sample, for example, after the first centrifugation step (see, e.g., FIGS. 2A, 3A and 6A). Each recess 436 illustrated in FIG. 10 is defined at least partially by six walls 442, a base or closed end 446, and an opening or open end 447. As a result, each recess 436 has a hexagonal horizontal cross-sectional shape (i.e., taken along a plane generally parallel to the base 446 of each recess 436). In some embodiments, the recesses 436 include no draft angle, or a draft angle of 0 degrees.

In some embodiments, the microstructured surface 438 can be formed from an etched master tool, for example, by compressing impression material onto the tool using a glass plate to an approximate final thickness of 1 mm.

In one embodiment of the microstructured surface 438 of FIG. 10, the recesses 436 can have a pitch (i.e., a center-to-center spacing between adjacent walls 342 or recesses 336, respectively) of about 100 micrometers, a wall height (or recess depth) of about 50 micrometers, and a draft angle (i.e., measured between the walls 342 and a vertical) of about 10 degrees.

Figure 11:
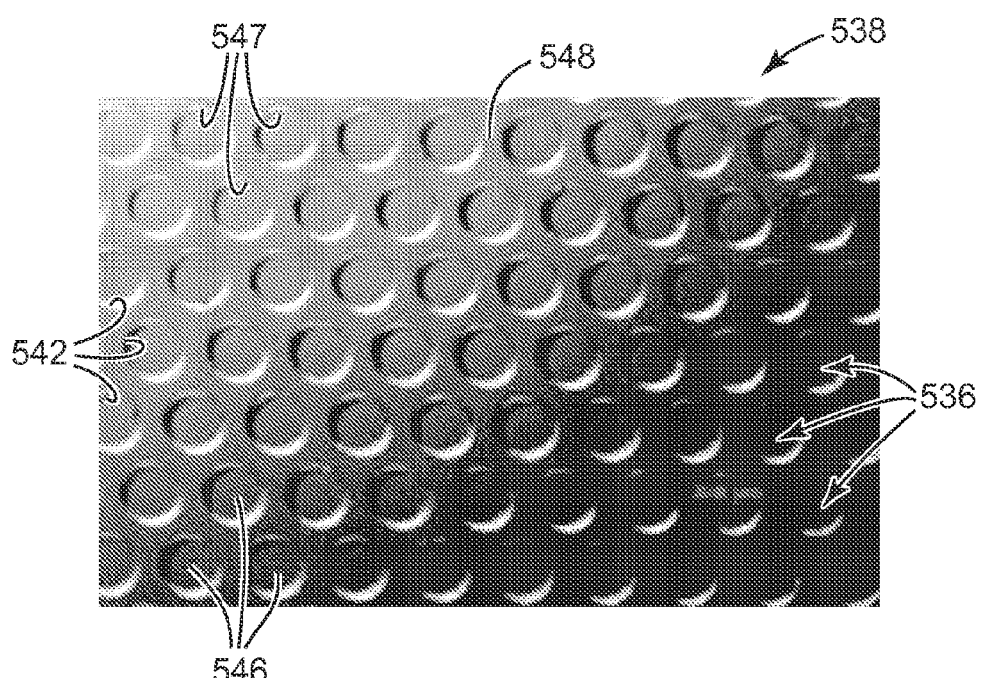

As shown in FIG. 11, the microstructured surface 538 includes a plurality of recesses 536 formed in a first major surface 548 and adapted to retain a concentrate of a sample, for example, after the first centrifugation step (see, e.g., FIGS. 2A, 3A and 6A). Each recess 536 illustrated in FIG. 11 is defined at least partially by a circular sidewall 542, a circular base or closed end 546, and a circular opening or open end 547, such that each recess 536 is substantially cylindrical in shape. As a result, each recess 536 has a circular horizontal cross-sectional shape (i.e., taken along a plane generally parallel to the base 546 of each recess 536). In addition, the recesses 536 are hexagonally-arranged or formed in a hexagonally-packed array.

As described above with respect to FIG. 6, the microstructured surfaces 438, 538, 638, 738, 838, 939, 1038 and 1138 can be formed according to a variety of processes. By way of example only, in some embodiments, the microstructured surface 538 of FIG. 11 can be formed via etching a photoresist-coated silicon wafer. One example of such a process is described in the Examples as the process for preparing microstructured surface MS1.

In some embodiments, the microstructured surfaces 638, 738, 838, 938, 1038 and 1138 of FIGS. 12-17 can represent examples of microstructured surfaces that can be formed according to a casting process that includes casting molten polymeric material against a cast roll equipped with male tooling having the inverse (e.g., "negative") of the desired microstructured surface. One example of such a process is described in greater detail in the Examples as the process for preparing microstructured surfaces MS2A-MS2F. In such casting processes, it can be necessary for the male tooling to have a draft angle, such that each protrusion of the tooling tapers toward its end or tip that enters the molten polymeric material. As a result, each recess formed by such a process will generally taper from its open end to its closed end, or base. As used herein, the phrase "draft angle" can be used to refer either to the tool used to create a recess, or to the angle formed in the resulting recess of a microstructured surface.

Figure 12:
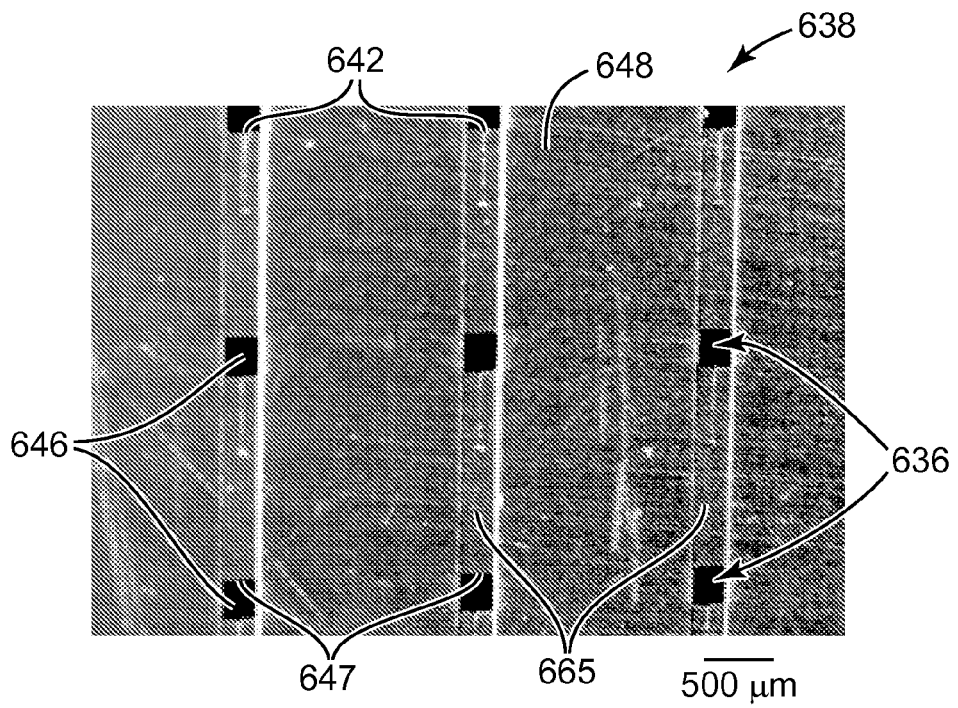

As shown in FIG. 12, the microstructured surface 638 includes a plurality of recesses 636 formed in a first major surface 648 and adapted to retain a concentrate of a sample. Each recess 636 illustrated in FIG. 12 is defined at least partially by four sidewalls 642 (e.g., each sidewall 642 being oriented substantially perpendicularly with respect to an adjacent sidewall 642), a base or closed end 646, and an open end 647, such that each recess 636 is substantially parallelipipedal (particularly, in FIG. 12, cuboid or rectangular cuboid) in shape. The term "substantially" is used to account for any draft angle. However, it should be understood that the three-dimensional shape of each recess 636 may be closer to that of a square frusto-pyramid, with a square (or rectangular) base 646 and a square (or rectangular) open end 647 and tapered sidewalls 642. As a result, each recess 636 has a square horizontal cross-sectional shape (i.e., taken along any plane generally parallel to the base 646 of each recess 636). As mentioned above, the draft angle can facilitate removal of male tooling from the material forming the microstructured surface 638 during the process of making the microstructured surface 638.

In addition, in the embodiment illustrated in FIG. 12, the microstructured surface 638 also includes tracks 665 formed in the first major surface 648 and extending linearly from one recesses 636 to another. In some embodiments, this is merely an artifact from the tool used in the casting process, but in some embodiments, the tracks 665 can also serve to retain a concentrate of a sample according to the present disclosure.

In some embodiments (see, e.g., FIGS. 11-12), the first major surface (e.g., 548 and 648) can include a larger portion of land area between recesses (e.g., 536 and 636); whereas, in some embodiments, (see FIG. 10) the recesses (e.g., 436) can be very densely arranged or packed on the first major surface (e.g., 448), such that very little land area is present between recesses. Generally, the packing density of the recesses will be described as "well density" or "recess density," as described above with respect to FIG. 6. Alternatively, this concept can be reflected by describing the "percent open area" on the first major surface, which generally refers to the percent of the first major surface that is occupied by recesses (or wells), as opposed to land area.

Figure 13:
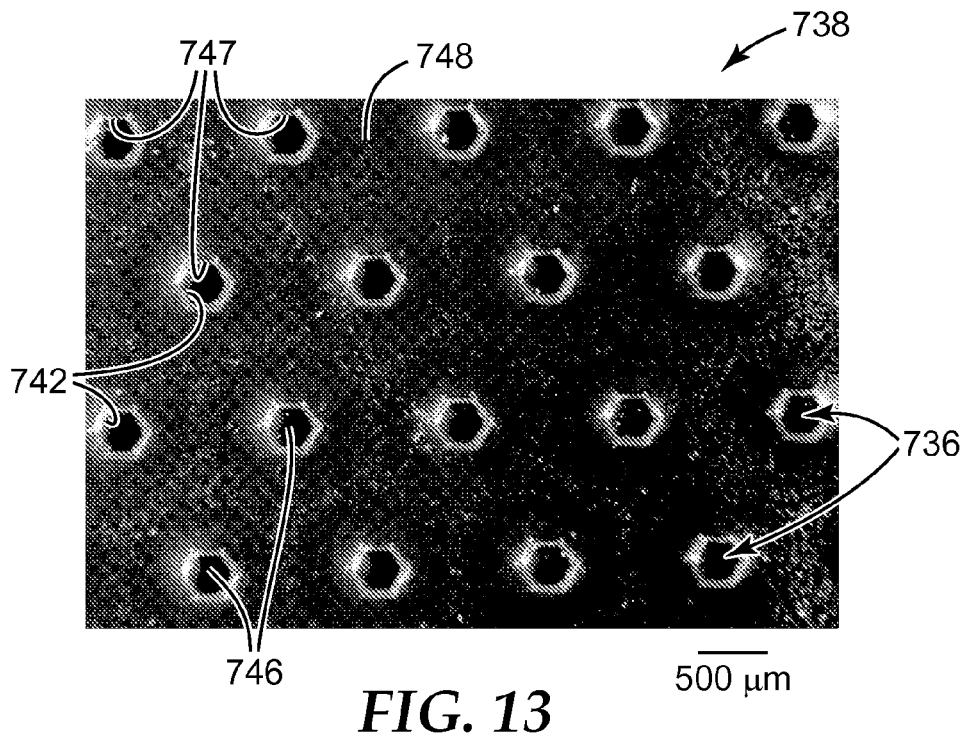

As shown in FIG. 13, the microstructured surface 738 includes a plurality of recesses 736 formed in a first major surface 748 and adapted to retain a concentrate of a sample. Each recess 736 illustrated in FIG. 13 is defined at least partially by six sidewalls 742, a base or closed end 746, and an opening or open end 747, such that each recess 736 is substantially hexagonal in shape, at least at the level of the first major surface 748. As a result, each recess 736 has a generally hexagonal horizontal cross-sectional shape (i.e., taken along a plane generally parallel to the base 746 of each recess 736). In some embodiments, such as the embodiment illustrated in FIG. 13, the microstructured surface 738 can be formed by tools having protrusion tips that are circular in shape, such that the base 746 is circular. In some embodiments, as shown in FIG. 13, the recesses 736 can taper, for example, toward the base 746. As described above, such a taper is generally referred to as a "draft angle," and can be useful in removing the tool from the first major surface 748 during formation (e.g., casting) of the microstructured surface 738.

Figure 14:
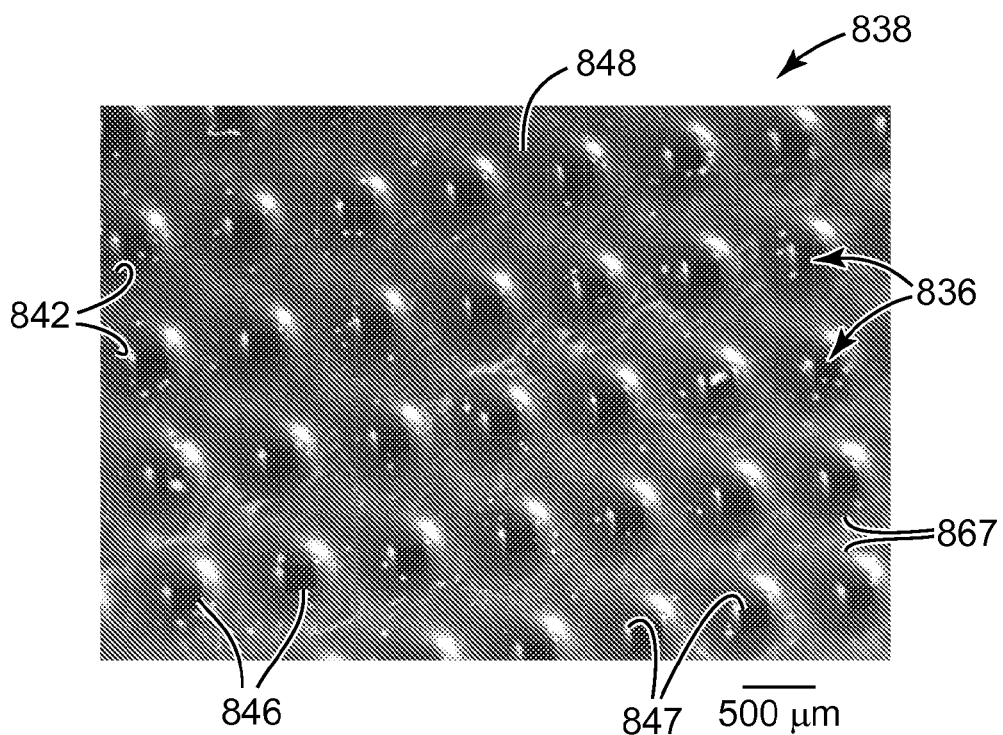

As shown in FIG. 14, the microstructured surface 838 includes a plurality of recesses 836 formed in a first major surface 848 and adapted to retain a concentrate of a sample. Each recess 836 illustrated in FIG. 14 is defined at least partially by four sidewalls 842 (e.g., each sidewall 842 being oriented substantially perpendicularly with respect to an adjacent sidewall 842), a base or closed end 846, and an opening or open end 847, such that each recess 836 is substantially parallelipipedal (particularly, in FIG. 14, cuboid or rectangular cuboid) in shape. The term "substantially" is used to account for any draft angle. However, it should be understood that the three-dimensional shape of each recess 836 may be closer to that of a square frusto-pyramid, with a square (or rectangular) base 846 and a square (or rectangular) open end 847 and tapered sidewalls 842. As a result, each recess 836 has a square (or rectangular) horizontal cross-sectional shape (i.e., taken along a plane generally parallel to the base 846 of each recess 836). In addition, in the embodiment illustrated in FIG. 14, the microstructured surface 838 also includes raised areas, bumps or protrusions 867 formed in the first major surface 848 and surrounding each recess 836. Each raised area 867 is generally round or hemispherical in shape. In some embodiments, this is merely an artifact from the tool used to create the microstructured surface 838, for example, in a casting process. In some embodiments, it can be preferred that a tool is used that does not create such artifacts in the resulting microstructured surface 138.

Figure 15:
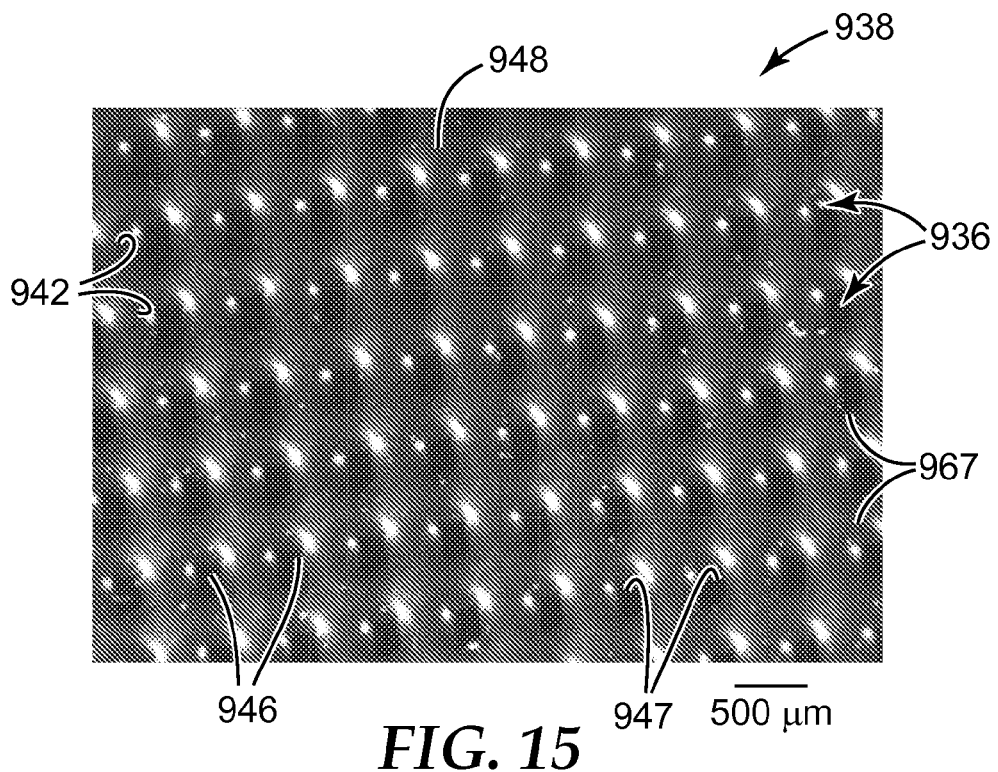

The microstructured surface 938 of FIG. 15 is substantially similar to the microstructured surface 838 of FIG. 14, except that the recesses 936 are more densely arranged or packed on a first major surface 948 than those of FIG. 14. That is, each recess 936 is formed in the first major surface 948 and is defined at least partially by four sidewalls 942, a base or closed end 946, and an open end 947, such that each recess 936 is substantially parallelipipedal in shape. Again, the term "substantially" is used to account for any draft angle. However, it should be understood that the three-dimensional shape of each recess 936 may be closer to that of a square frusto-pyramid, with a square (or rectangular) base 946 and a square (or rectangular) open end 947 and tapered sidewalls 942. As a result, each recess 936 has a square horizontal cross-sectional shape (i.e., taken along a plane generally parallel to the base 946 of each recess 936), and each recess 936 is surrounded by a raised area, bump or protrusion 967 that is generally round or hemispherical in shape.

Examples of tools 850 and 950 (e.g., male tooling) that can be used to form the microstructured surfaces 838 and 938 of FIGS. 14 and 15 are shown in FIGS. 21A-21B and 22A-22B, respectively. As shown in FIGS. 21A-21B and 22A-22B, each of the tools 850 and 950 can include a plurality of protrusions, posts, or pins 855, 955 that extend from a tool surface or major surface 880, 980, each of which corresponds to one recess 836, 936, respectively. As shown, each protrusion 855, 955 is generally frusto-pyramidal in shape. As shown, the protrusions 855, 955 include the inverse or "negative" shape of the recesses 836, 936. Each protrusion 855, 955 includes a base 857, 957 that will ultimately form and correspond to the open end 847, 947 of a recess 836, 936, and a tip 859, 959 that will ultimately form and correspond to the base or closed end 846, 946 of a recess 836, 936.

Figure 21A:
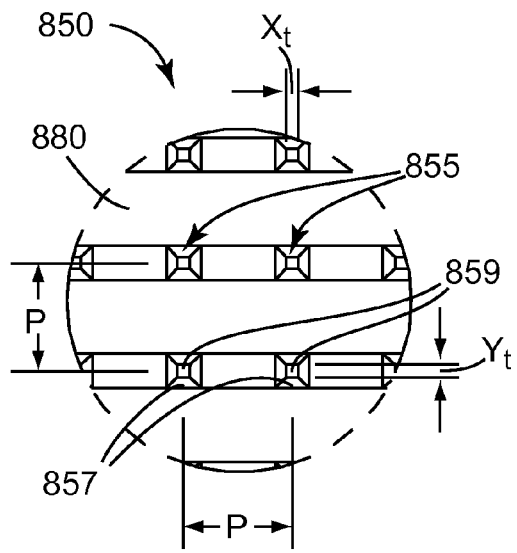
FIG. 21A is a close-up top plan view of a tool for making the microstructured surface of FIG. 14.
Figure 21B:
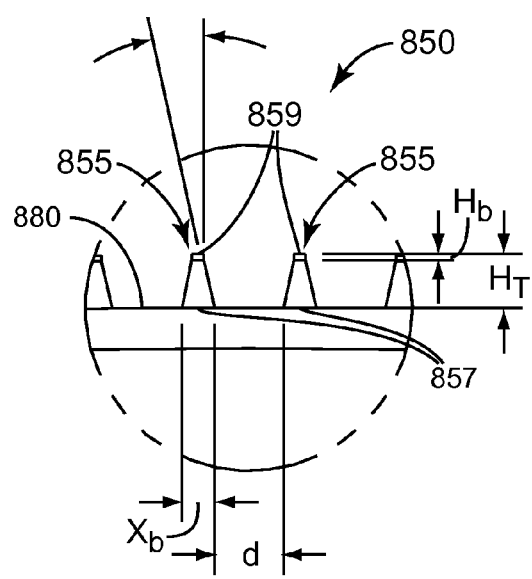
FIG. 21B is a close-up side elevational view of the tool of FIG. 21A.
Figure 22A:
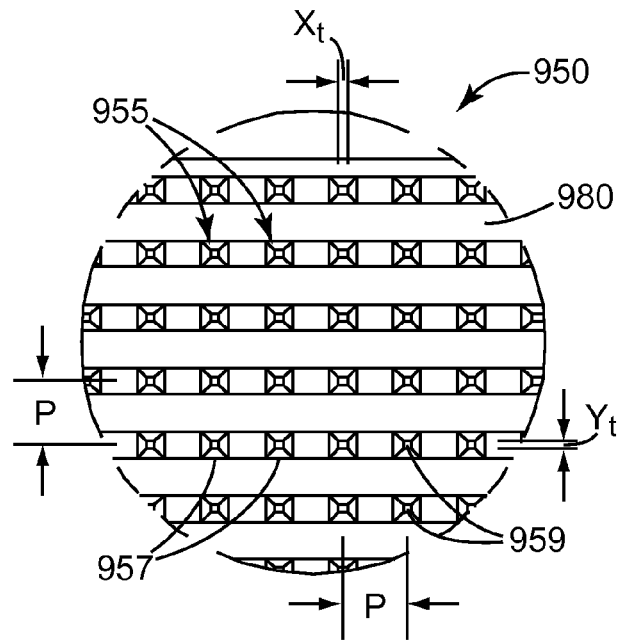
FIG. 22A is a close-up top plan view of a tool for making the microstructured surface of FIG. 15.
Figure 22B:
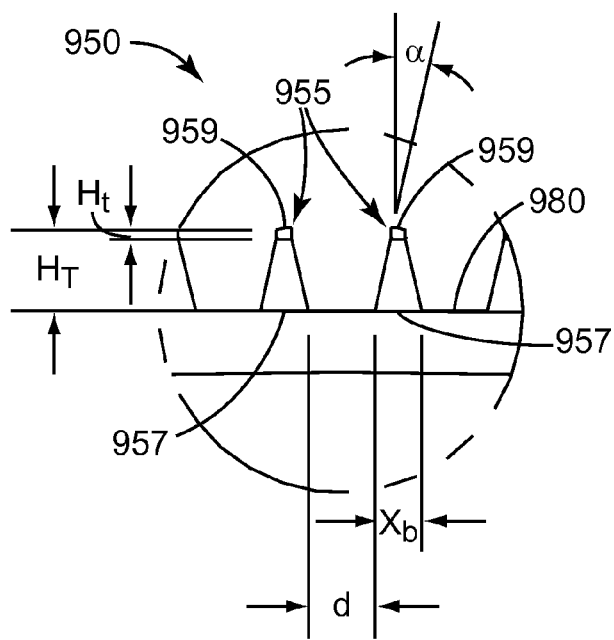
FIG. 22B is a close-up side elevational view of the tool of FIG. 22A.

The width of each tip 859, 959 is represented by "$X_t$," and the length is generally represented by the letter "$Y_t$" (see FIGS. 21A and 22A). The width (or length) of each base 857, 957 is represented by "$X_b$." The pitch, or center-to-center distance between adjacent protrusions 855, 955 is represented by the letter "P" (see FIGS. 21A and 22A), and the distance between protrusions 855, 955 is represented by the letter "d" (see FIGS. 21B and 22B). The total height of each protrusion 855, 955 is represented by "$H_T$," and the height of each tip 859, 959 is represented by "$H_t$" (see FIGS. 21B and 22B). The total height "$H_T$" will generally correspond to the depth of each recess 836, 936, respectively. The draft angle of each protrusion 855, 955 is represented by the angle α.

Measured and/or calculated dimensions for the recesses 836 and 936 of FIGS. 14 and 15 that are formed by tools 850 and 950 for one exemplary embodiment of each are given in Table 1 in the Examples, where the microstructured surfaces 838 and 939 are referred to as "MS2C" and "MS2D," respectively. In addition, dimensions for exemplary embodiments of the tools 850 and 950 are given in Table 2 in the Examples.

Figure 16:
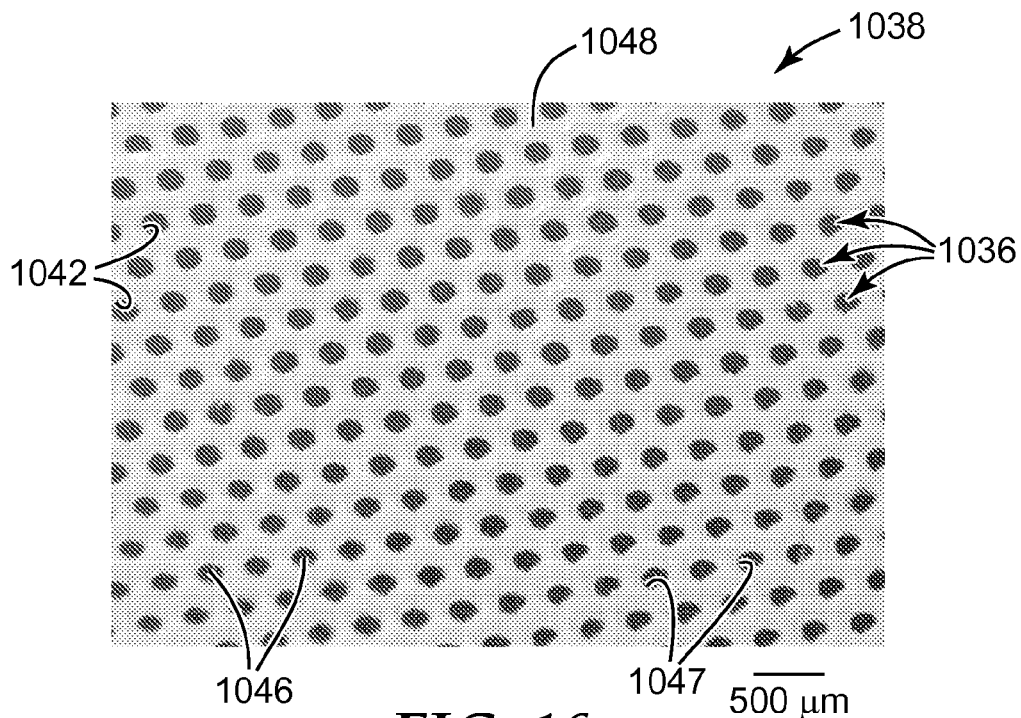

As shown in FIG. 16, the microstructured surface 1038 includes a plurality of recesses 1036 formed in a first major surface 1048 and adapted to retain a concentrate of a sample. Each recess 1036 illustrated in FIG. 16 is defined at least partially by six sidewalls 1042, a base or closed end 1046, and an opening or open end 1047, such that each recess 1036 is substantially hexagonal in shape, at least at the level of the first major surface 1048. As a result, each recess 1036 has a generally hexagonal horizontal cross-sectional shape (i.e., taken along a plane generally parallel to the base 1046 of each recess 1036). In some embodiments, such as the embodiment illustrated in FIG. 16, the microstructured surface 1038 can be formed by tools having protrusion tips that are circular in shape, such that the base 1046 is circular. The recesses 1036 each include a draft angle (e.g., as reported for microstructured surface MS2E in the Examples), such that each recess 1036 tapers from its open end 1047 to its closed end or base 1046. In addition, the recesses 1036 are hexagonally-packed, such that their center-to-center spacing, or pitch, is generally smaller, and the recess density is higher, than that of a similar square-packed design.

The microstructured surface 1038 can be formed from a tool that is similar to that of tools 850, 950, except that the protrusions would be hexagonally-packed. For example, in some embodiments, the tool can include hexagonally-packed protrusions having a pitch P of 350 micrometers, a tip diameter (i.e., "characteristic dimension") of 225 micrometers, a base diameter of 300-325 micrometers, and a height of 250 micrometers.

Figure 17:
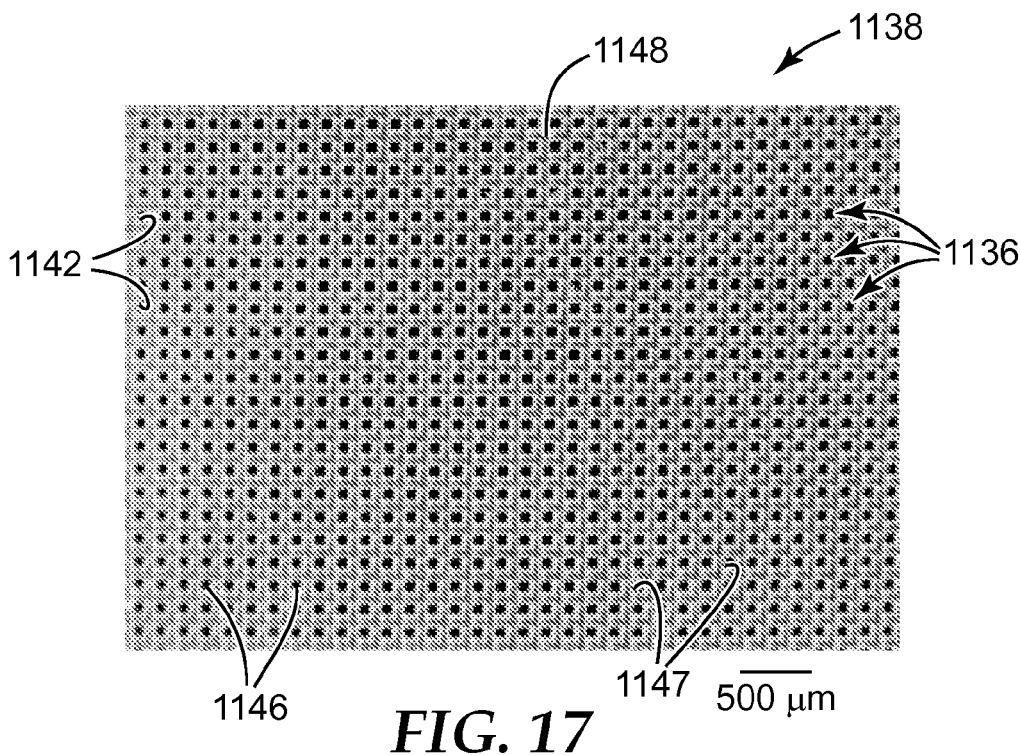

The microstructured surface 1138 of FIG. 17 is substantially similar to the microstructured surface 838 of FIG. 14 or the microstructured surface 938 of FIG. 15, except that the recesses 1136 are even more densely arranged or packed on a first major surface 1148 than those of FIGS. 14 and 15. That is, each recess 1136 is formed in the first major surface 1148 and is defined at least partially by four sidewalls 1142, a base or closed end 1146, and an open end 1147, such that each recess 1136 is substantially parallelipipedal in shape. Again, the term "substantially" is used to account for any draft angle. However, it should be understood that the three-dimensional shape of each recess 1136 may be closer to that of a square frusto-pyramid, with a square (or rectangular) base 1146 and a square (or rectangular) open end 1147 and tapered sidewalls 1142. As a result, each recess 1136 has a square horizontal cross-sectional shape (i.e., taken along a plane generally parallel to the base 1146 of each recess 1136). As shown in FIG. 17, each recess 1136 is surrounded by a square-shaped indentation or groove, which, in some embodiments, is an artifact of the tooling used to create the microstructured surface 1138, for example, in a casting process.

Figure 23A:
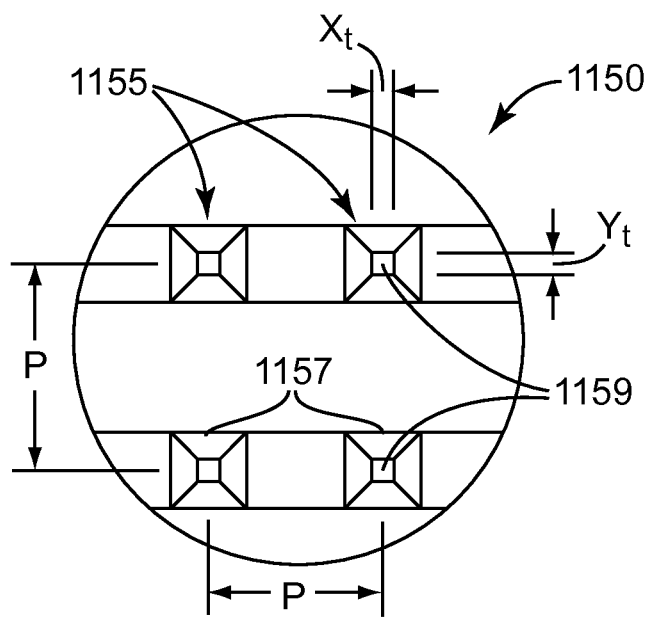
FIG. 23A is a close-up top plan view of a tool for making the microstructured surface of FIG. 17.
Figure 23B:
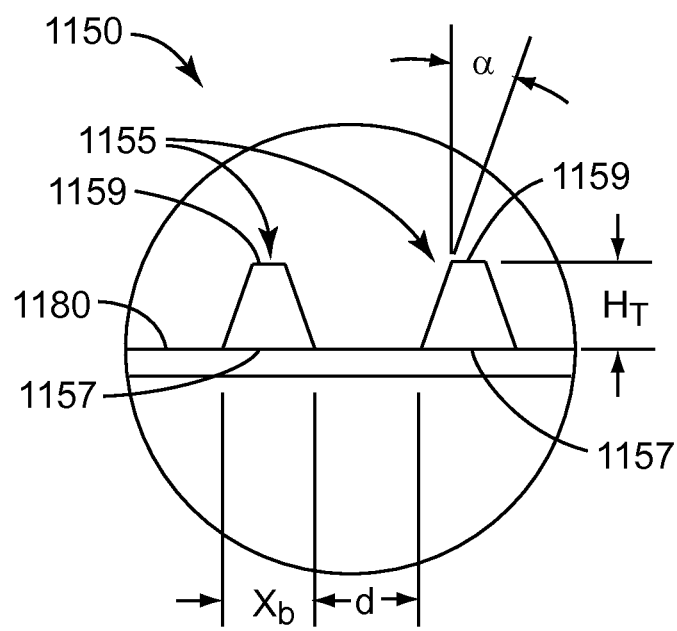
FIG. 23B is a close-up side elevational view of the tool of FIG. 23A.

One example of a tool 1150 (e.g., male tooling) that can be used to form the microstructured surface and 1138 of FIG. 17 is shown in FIGS. 23A-23B. As shown in FIGS. 23A-23B, the tool 1150 can include a plurality of protrusions or pins 1155 that extend from a tool surface or major surface 1180, each of which corresponds to one recess 1136. As shown, each protrusion 1155 is generally frusto-pyramidal in shape. As shown, the protrusions 1155 include the inverse or "negative" shape of the recesses 1136. Each protrusion 1155 includes a base 1157 that will ultimately form and correspond to the open end 1147 of a recess 1136, and a tip 1159 that will ultimately form and correspond to the base or closed end 1146 of a recess 1136.

The width of each tip 1159 is represented by "$X_t$," and the length is generally represented by the letter "$Y_t$" (see FIG. 23A). The width (or length) of each base 1157 is represented by "$X_b$." The pitch, or center-to-center distance between adjacent protrusions 1155 is represented by the letter "P" (see FIG. 23A), and the distance between protrusions 1155 is represented by the letter "d" (see FIG. 23B). The total height of each protrusion 1155 is represented by "$H_T$" (see FIG. 23B). The total height "$H_T$" will generally correspond to the depth of each recess 1136. The draft angle of each protrusion 1155 is represented by the angle α.

Measured and/or calculated dimensions for the recesses 1136 that are formed by the tool 1150 for one exemplary embodiment are given in Table 1 in the Examples, where the microstructured surface 1138 is referred to as "MS2F." In addition, dimensions for one exemplary embodiment of the tool 1150 are given in Table 2 in the Examples.

FIGS. 18A-18H, and particularly FIGS. 18A-18E, illustrate a substrate, or insert, 1290 that can be coupled to a second portion (e.g., the second portion 104 of FIGS. 1-3 or the second portion 204 of FIGS. 5-6C) and in which a microstructured surface 1238 can be formed. As shown in FIG. 18A, the substrate 1290 can include an outer wall 1291 and a flange 1292 that can be used for coupling to a second portion. The second portion can include mating ridges or features for engaging at least one of the outer wall 1291 and the flange 1292. For example, in some embodiments, the substrate 1290 can couple to the second portion to form a cap for a container (e.g., the container 108 of FIGS. 1-3 or the container 208 of FIGS. 5-6C) much like that of a mason jar that has a lid and a cover that is configured to couple to the jar as well as hold the lid in place over the open end of the jar. As such, in some embodiments, the substrate 1290 can be referred to as a second portion, or at least a portion thereof. As such, any description of the substrate 1290 herein can also be applied to a "second portion" of the present disclosure.

The substrate 1290 can further include a first side 1240 in which the microstructured surface 1238 is formed, and a second side 1241 opposite the first side 1240, such that the first side 1240 would generally face an interior of a container, and the second side 1241 would generally face an exterior of a container.

As mentioned above, in some embodiments, at least a portion of the substrate 1290 (e.g., a portion that is overlapping or coextensive with the microstructured surface 1238) can be substantially transparent to allow the microstructured surface 1238 to be viewed, detected and/or interrogated from the second side 1241. Particularly, the microstructured surface 1238 can include one or more recesses 1236 formed in a first major surface 1248 of the substrate 1290, the recesses 1236 adapted to retain a concentrate of a sample. In some embodiments, at least a portion of the recesses 1236 (e.g., a base 1246 thereof) can be substantially transparent to allow the contents of the recesses 1236 to be viewed, detected and/or interrogated from the second side 1241.

Each recess 1236 illustrated in FIGS. 18A-18H is defined at least partially by four sidewalls 1242, a base or closed end 1246, and an opening or open end 1247, such that each recess 1236 is substantially parallelipipedal in shape. The term "substantially" is used to account for any draft angle α, as shown in FIG. 18E. That is, as shown in FIGS. 18D-18H, the three-dimensional shape of each recess 1236 may be closer to that of a square frusto-pyramid, with a square (or rectangular) base 1246 and a square (or rectangular) open end 1247 and tapered sidewalls 1242 that taper from the open end 1247 to the closed end 1246. As a result, each recess 1236 has a square (or rectangular) horizontal cross-sectional shape (i.e., taken along a plane generally parallel to the base 1246 of each recess 1236). Such tapered sidewalls 1242 can be an artifact of the method used to make the recesses 1236. In some embodiments, the microstructured surface 1238 can be formed by molding, as described in Example as the process for preparing microstructured surfaces MS3A and MS3B. One example of the microstructured surface 1238 of FIGS. 18A-18H is described in the Examples as "MS3A."

Figure 18F:
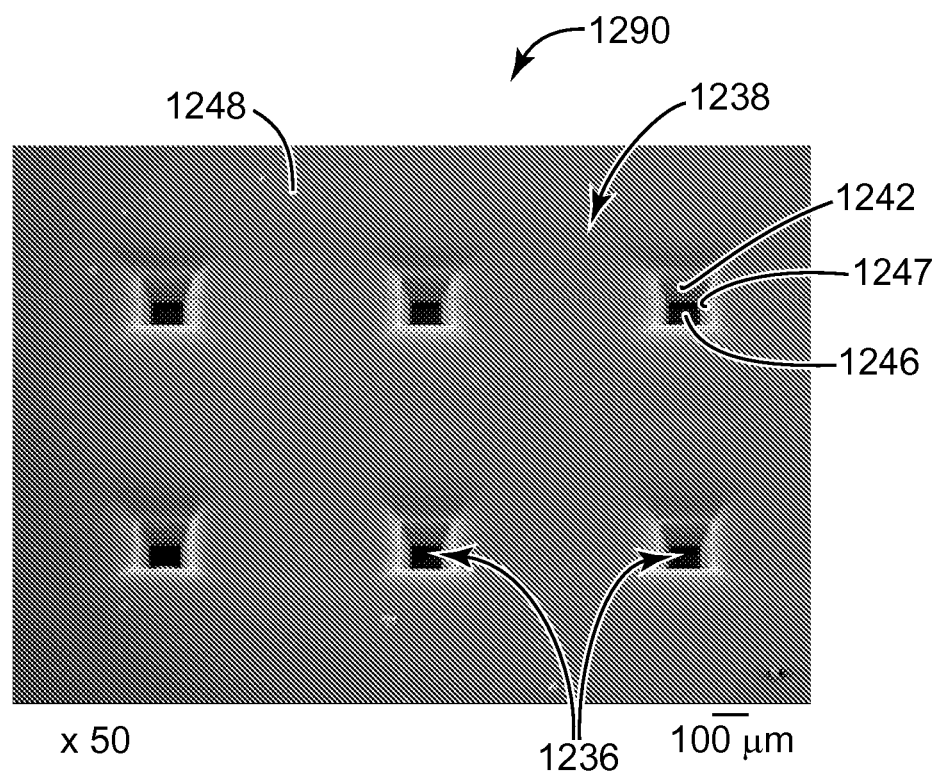
FIG. 18F is an optical micrograph of a top surface of the substrate of FIGS. 18A-18E, taken at a magnification of 50×.
Figure 18G:
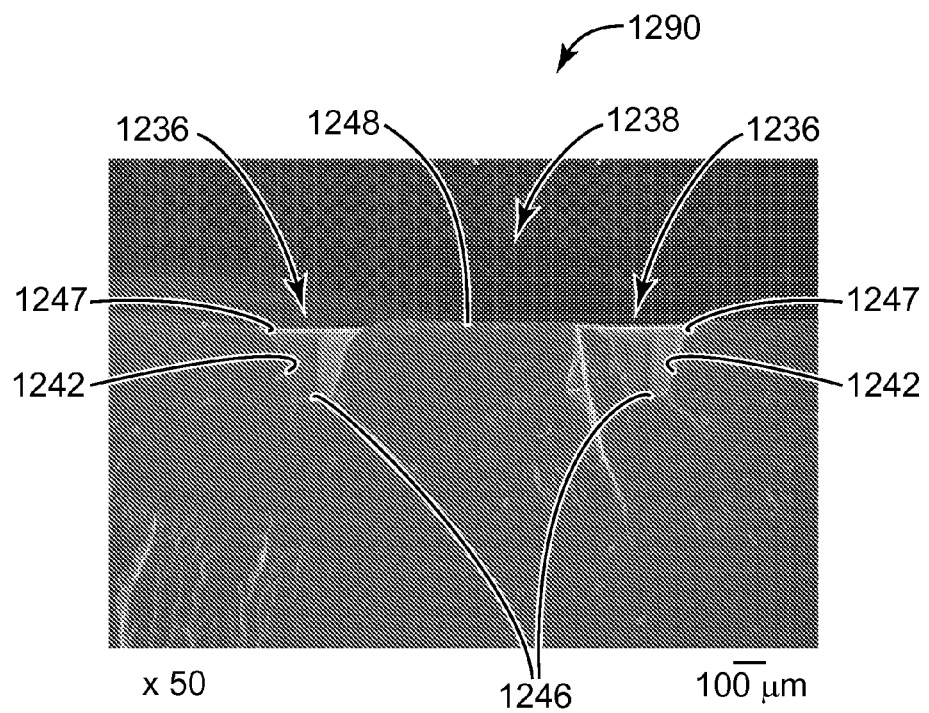
FIG. 18G is an optical micrograph of a cross-section of the substrate of FIGS. 18A-18F, taken at a magnification of 50×.
Figure 18H:
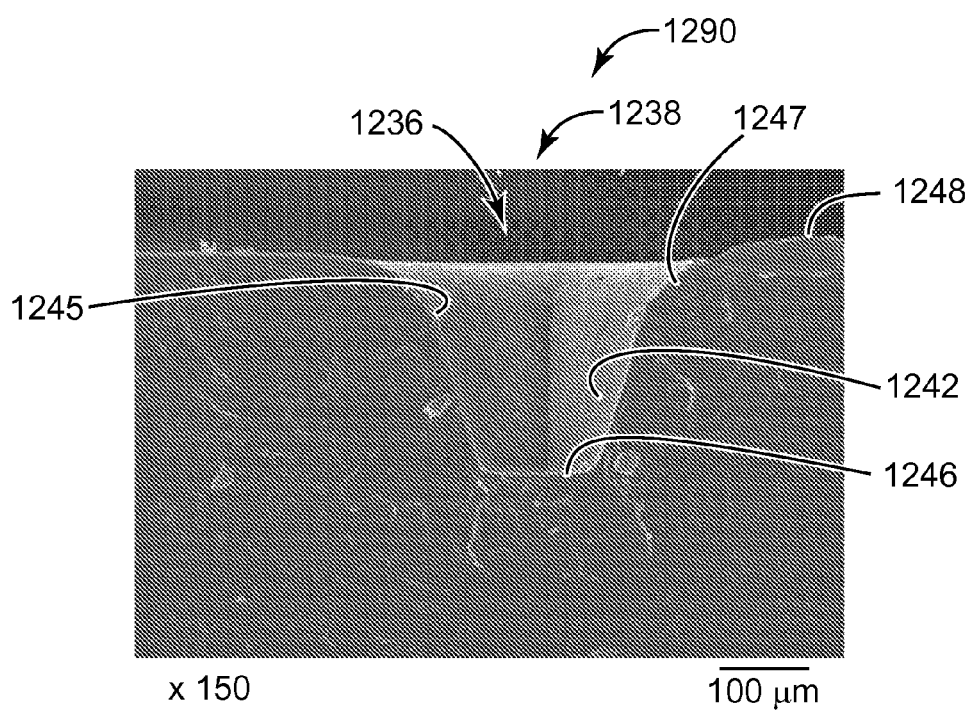
FIG. 18H is an optical micrograph of a cross-section of the substrate of FIGS. 18A-18G, taken at a magnification of 150×.

The optical micrographs of FIGS. 18F-18H also illustrate that in some embodiments, the open end 1247 can be at least partially smooth or rounded. Such smooth or rounded top edges or open ends 1247 can be useful in adequately removing a supernatant from the concentrate retained in the recesses 1236 after a centrifugation step. That is, in some embodiments, if the open ends 1247 are defined by too sharp of edges and angles, a liquid sample (e.g., an aqueous sample) may have a tendency to break at these sharp edges as a container is inverted following centrifugation. Such necking or breakage may cause portions of the liquid sample (e.g., the supernatant) to collect in small bridges or pools on the first major surface 1248, rather than sufficiently being retained in the recesses 1236. Such bridging or necking can be a problem because if large portions of the sediment formed during the centrifugation process end up on the first major surface 1248 but not within the recesses 1236, those portions may not be easily detectable. As a result, the smooth or rounded surfaces and edges at the open end 1247 of the recesses 1236 can enhance retention of the sediment of the sample in the recesses 1236, and can further enhance detection of the analyte(s) of interest in the sample. As mentioned above, another factor that can affect the formation of bridges, necks or pools on the first major surface 1248 above the recesses 1236 is the speed at which the container comprising the microstructured surface 1238 is inverted following a centrifugation step.

In some embodiments, this can be described as the sidewalls 1242 of the recesses 1236 having curved, arcuate, or radiused upper surfaces, and the first major surface 1248 can be described as being formed of curved, arcuate or radiused surfaces. In some embodiments, an inflection point 1245 (see FIG. 18H) between the radiused portion of the sidewall 1242 and the rest of the sidewall 1242 (e.g., which can be straight from the inflection point to the base 1246) can determine the height of the concentrate retained in the recess 1236. The inflection point can also be referred to as the point at which the tangent (or first derivative) of the radiused portion of the sidewall 1242 becomes parallel with the sidewall 1242. Example 25 describes how the height of a liquid (concentrate) retained in microstructured recesses was assessed, and how it was determined that the liquid height coincided with the inflection point of the sidewall. Example 25 therefore demonstrates how recesses in the microstructured surfaces of the present disclosure can be designed to achieve a desired height (e.g., liquid height) of concentrate (e.g., liquid) retained in the recesses following centrifugation and inversion. Such a height can also correspond to a desired volume, as well as a desired concentration of an analyte of interest (if present). As a result, the geometry of the sidewall (e.g., the radius of curvature, the inflection point, etc.) can be controlled to achieve a reduced volume of concentrate in each recess, so as to achieve an increased concentration of an analyte of interest (if present) in the concentrate, which can enhance detection.

In some embodiments, the height of a microstructured recess can be calculated as the perpendicular height or distance between the base of the recess and the top plane (tangent) of an adjacent sidewall. In some embodiments, the inflection point (and the resulting level or height of the concentrate in the recesses) in the sidewall can occur at a position of at least 50% of the height of the recess, in some embodiments, at least 60%, in some embodiments, at least 70%, and in some embodiments, at least 75%. In some embodiments, the inflection point in the sidewall can occur at a position no greater (higher) than 95% of the height of the recess, in some embodiments, no greater than 90%, and in some embodiments, no greater than 85%. As described in Example 25, in some embodiments, the inflection point can occur at about 70% of the height of the recess.

The width of each base 1246 is represented by the letter "X", and the length is generally represented by the letter "Y" (see FIG. 18D). The pitch, or center-to-center distance between adjacent recesses 1236 is represented by the letter "P" (see FIG. 18D), and the vertical height, or depth, of each recess 1236 is represented by the letter "H" (see FIG. 18E).

As shown in FIG. 18C, in some embodiments, the flange 1292 of the substrate 1290 can include an angled top surface that is angled with respect to the horizontal by angle β. In addition, the total height or thickness of the substrate 1290 is represented in FIG. 18C by "$T_1$," and the height or thickness of the flange 1292 is represented in FIG. 18C by "$T_2$." Furthermore, by way of example only, the substrate 1290 is generally circular in shape, and the transverse dimension (e.g., diameter, in circular embodiments) "$X_1$" of the outer wall 1291 (or of the portion of the substrate 1290 including the outer wall 1291) is shown in FIG. 18C. In addition, the transverse dimension (e.g., diameter, in circular embodiments) "$X_2$" of the flange 1292 (or of the portion of the substrate 1290 including the flange 1292) is also shown in FIG. 18C.

Figure 24A:
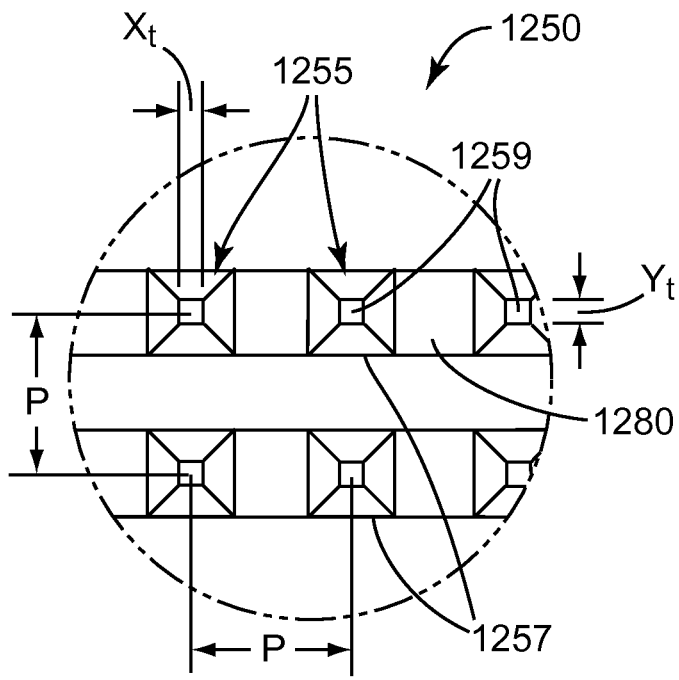
FIG. 24A is a close-up top plan view of a tool for making the microstructured surface of FIGS. 18A-18H.
Figure 24B:
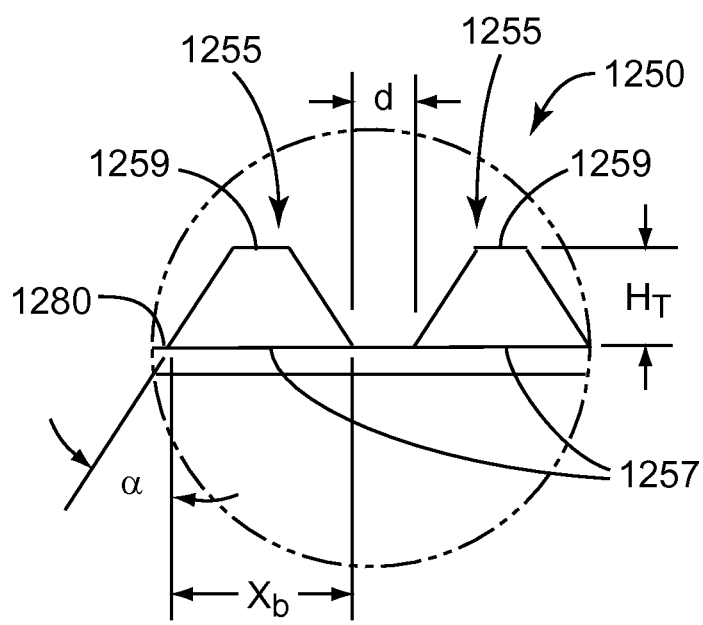
FIG. 24B is a close-up side elevational view of the tool of FIG. 24A.

One example of a tool 1250 (e.g., male tooling) that can be used to form the microstructured surface and 1238 of FIGS. 18A-18H is shown in FIGS. 24A-24B. As shown in FIGS. 24A-24B, the tool 1250 can include a plurality of protrusions or pins 1255 that extend from a tool surface or major surface 1280, each of which corresponds to one recess 1236. As shown, each protrusion 1255 is generally frustopyramidal in shape. As shown, the protrusions 1255 include the inverse or "negative" shape of the recesses 1236. Each protrusion 1255 includes a base 1257 that will ultimately form and correspond to the open end 1247 of a recess 1236, and a tip 1259 that will ultimately form and correspond to the base or closed end 1246 of a recess 1236.

The width of each tip 1259 is represented by "$X_t$", and the length is generally represented by the letter "$Y_t$" (see FIG. 23A). The width (or length) of each base 1257 is represented by "$X_b$." The pitch, or center-to-center distance between adjacent protrusions 1255 is represented by the letter "P" (see FIG. 24A), and the distance between protrusions 1255 is represented by the letter "d" (see FIG. 24B). The total height of each protrusion 1255 is represented by "$H_T$" (see FIG. 24B). The total height "$H_T$" will generally correspond to the depth of each recess 1236. The draft angle of each protrusion 1255 is represented by the angle α.

Measured and/or calculated dimensions for the recesses 1236 that are formed by the tool 1250 for one exemplary embodiment are given in Table 1 in the Examples, where the microstructured surface 1238 is referred to as "MS3A." In addition, dimensions for one exemplary embodiment of the tool 1150 are given in Table 2 in the Examples.

The tools 850, 950, 1050 and 1150 represent specific examples of tools used to form microstructured surfaces 838, 938, 1038 and 1138, respectively. However, in some embodiments, the width ($X_t$) or the length ($Y_t$) of the tip 859, 959, 1059, 1159 of the protrusion 855, 955, 1155, 1255 can be no greater than about 100 micrometers, in some embodiments, no greater than about 90 micrometers, and in some embodiments, no greater than about 75 micrometers.

In some embodiments, the width or length ($X_b$) of the base 857, 957, 1157, 1257 of the protrusion 855, 955, 1155, 1255 can be no greater than about 300 micrometers, in some embodiments, no greater than about 250 micrometers, in some embodiments, no greater than about 150 micrometers, and in some embodiments, no greater than about 100 micrometers.

In some embodiments, the pitch or center-to-center spacing (P) of the protrusions 855, 955, 1155, 1255 can be no greater than about 1 mm, in some embodiments, no greater than about 850 micrometers, in some embodiments, no greater than about 800 micrometers, in some embodiments, no greater than about 600 micrometers, in some embodiments, no greater than about 200 micrometers, and in some embodiments, no greater than about 150 micrometers.

In some embodiments, the distance (d) between the bases 857, 957, 1157, 1257 of the protrusions 855, 955, 1155, 1255 can be no greater than about 600 micrometers, in some embodiments, no greater than about 550 micrometers, in some embodiments, not greater than about 350 micrometers, and in some embodiments, no greater than about 50 micrometers.

In some embodiments, the total height ($H_T$) of the protrusion 855, 955, 1155, 1255 can be no greater than about 500 micrometers, in some embodiments, no greater than about 400 micrometers, in some embodiments, no greater than about 250 micrometers, and in some embodiments, no greater than about 150 micrometers.

In some embodiments, the height ($H_t$) of the tip 859, 959 of the protrusion 855, 955 can be no greater than about 100 micrometers, and in some embodiments, no greater than about 50 micrometers.

In some embodiments, the draft angle (a) of the protrusions 855, 955, 1055, 1155, 1255 can be about 5 degrees, in some embodiments, at least about 10 degrees, in some embodiments, at least about 12.5 degrees, and in some embodiments, at least about 15 degrees. In some embodiments, the draft angle is no greater than about 50 degrees, in some embodiments, no greater than about 30 degrees, in some embodiments, no greater than about 25 degrees, and in some embodiments, no greater than about 20 degrees. In some embodiments, the draft angle ranges from about 10 degrees to about 12.5 degrees.

FIGS. 19A-19H, and particularly FIGS. 19A-19E, illustrate a substrate, or insert, 1390 that can be coupled to a second portion (e.g., the second portion 104 of FIGS. 1-3 or the second portion 204 of FIGS. 5-6C) and in which a microstructured surface 1338 can be formed. The substrate 1390 shares many of the same elements and features described above with reference to the illustrated embodiment of FIGS. 18A-18H. Accordingly, elements and features corresponding to the elements and features of the illustrated embodiment of FIGS. 18A-18H are provided with the same reference numerals in the 1300 series, respectively. Reference is made to the description above accompanying FIGS. 18A-18H for a more complete description of the features and elements (and alternatives to such features and elements) of the embodiment illustrated in FIGS. 19A-19H. The most notable difference between the substrate 1390 of FIGS. 19A-19H and the substrate 1290 of FIGS. 18A-18H is the recess, or well, size and density in the microstructured surface 1338, as compared to that of the microstructured surface 1238. That is, the recess density of the microstructured surface 1338 is much higher than that of the microstructured surface 1238.

Figure 19A:
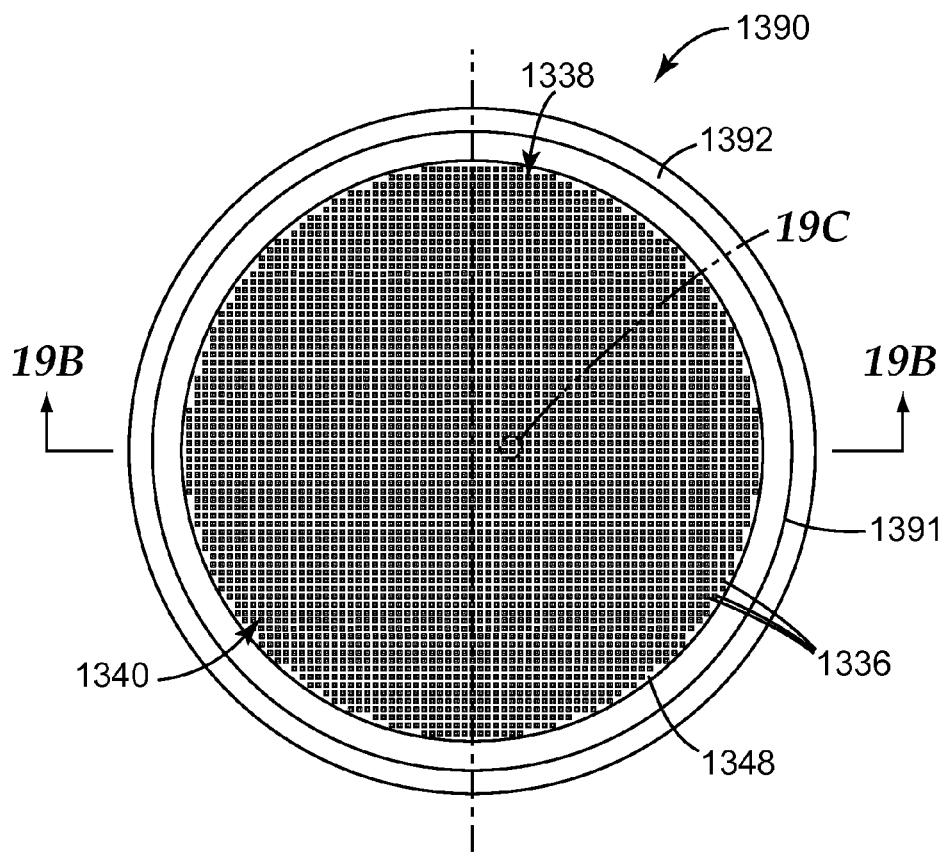
FIG. 19A is a top plan view of a substrate comprising a microstructured surface according to another embodiment of the present disclosure.

As shown in FIG. 19A, the substrate 1390 can include an outer wall 1391 and a flange 1392 that can be used for coupling to a second portion. As described with respect to the substrate 1290, a second portion can include mating ridges or features for engaging at least one of the outer wall 1391 and the flange 1392.

The substrate 1390 can further include a first side 1340 in which the microstructured surface 1338 is formed, and a second side 1341 opposite the first side 1340, such that the first side 1340 would generally face an interior of a container, and the second side 1341 would generally face an exterior of a container.

As mentioned above, in some embodiments, at least a portion of the substrate 1390 (e.g., a portion that is overlapping or coextensive with the microstructured surface 1338) can be substantially transparent to allow the microstructured surface 1338 to be viewed, detected and/or interrogated from the second side 1341. Particularly, the microstructured surface 1338 can include one or more recesses 1336 formed in a first major surface 1348 of the substrate 1390, the recesses 1336 adapted to retain a concentrate of a sample. In some embodiments, at least a portion of the recesses 1336 (e.g., a base 1346 thereof) can be substantially transparent to allow the contents of the recesses 1336 to be viewed, detected and/or interrogated from the second side 1341.

Figure 19B:
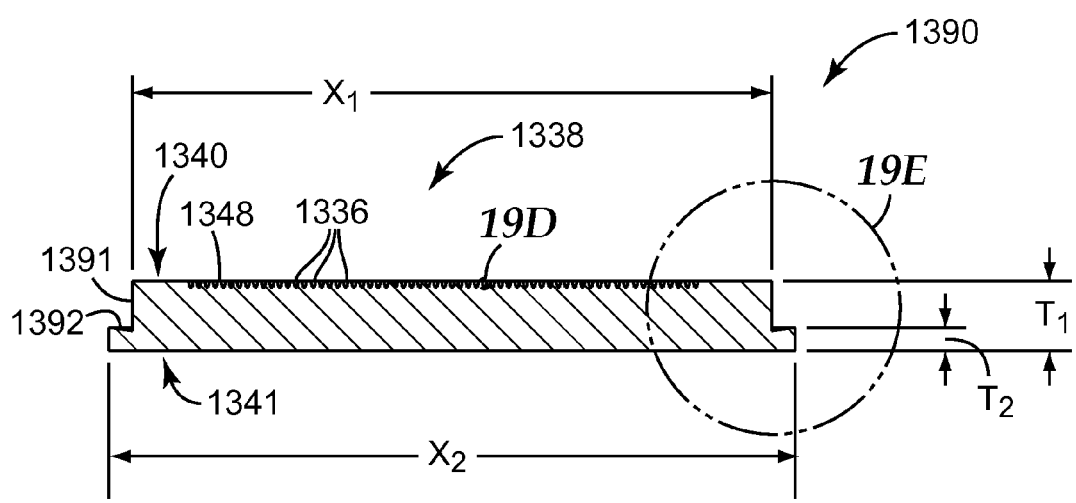
FIG. 19B is a side cross-sectional view of the substrate of FIG. 19A, taken along line 19B-19B of FIG. 19A.
Figure 19C:
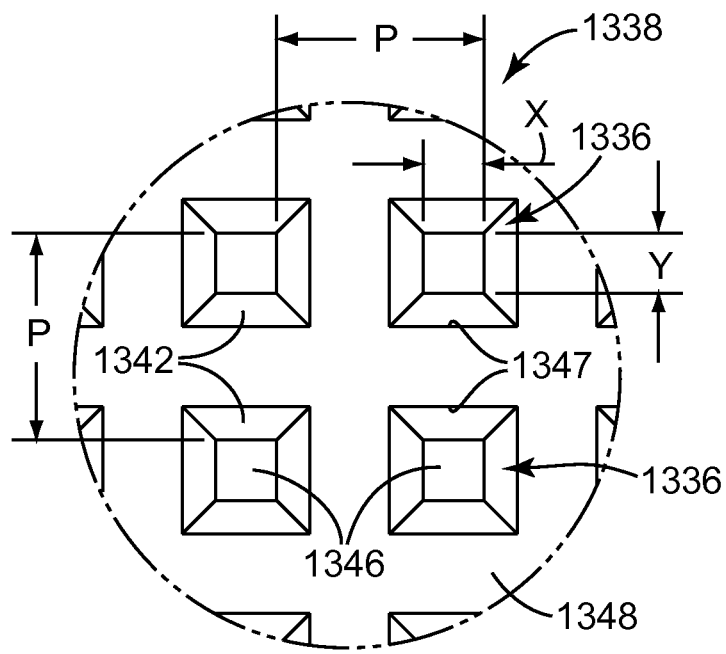
FIG. 19C is a close-up top plan view of the substrate of FIGS. 19A and 19B, taken of the area labeled 19C in FIG. 19A.
Figure 19D:
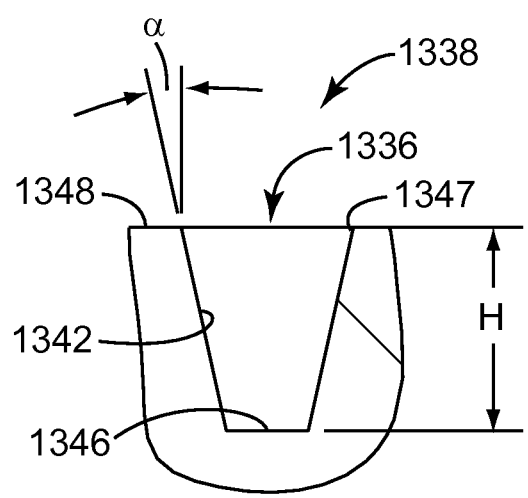
FIG. 19D is a close-up side cross-sectional view of the substrate of FIGS. 19A-19C, taken of the area labeled 19D in FIG. 19B.

Each recess 1336 illustrated in FIGS. 19A-19H is defined at least partially by four sidewalls 1342, a base or closed end 1346, and an opening or open end 1347, such that each recess 1336 is substantially parallelipipedal in shape. The term "substantially" is used to account for any draft angle α, as shown in FIG. 19D. That is, as shown in FIGS. 19D and 19F-19H, the three-dimensional shape of each recess 1336 may be closer to that of a square frusto-pyramid, with a square (or rectangular) base 1346 and a square (or rectangular) open end 1347 and tapered sidewalls 1342 that taper from the open end 1347 to the closed end 1346. As a result, each recess 1336 has a square (or rectangular) horizontal cross-sectional shape (i.e., taken along a plane generally parallel to the base 1346 of each recess 1336). Such tapered sidewalls 1342 can be an artifact of the method used to make the recesses 1336. In some embodiments, the microstructured surface 1338 can be formed by molding, as described in the Examples as the process of preparing microstructured surfaces MS3A and MS3B. One example of the microstructured surface 1338 of FIGS. 19A-19H is described in the Examples as "MS3B."

Figure 19E:
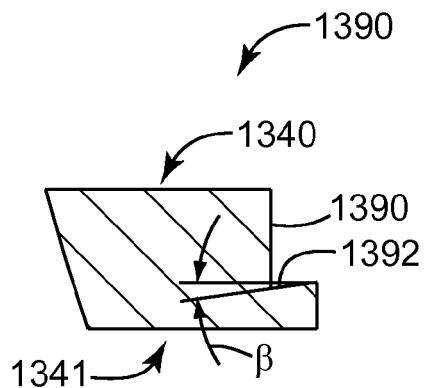
FIG. 19E is a close-up side cross-sectional view of the substrate of FIGS. 19A-19D, taken of the area labeled 19E in FIG. 19B.
Figure 19F:
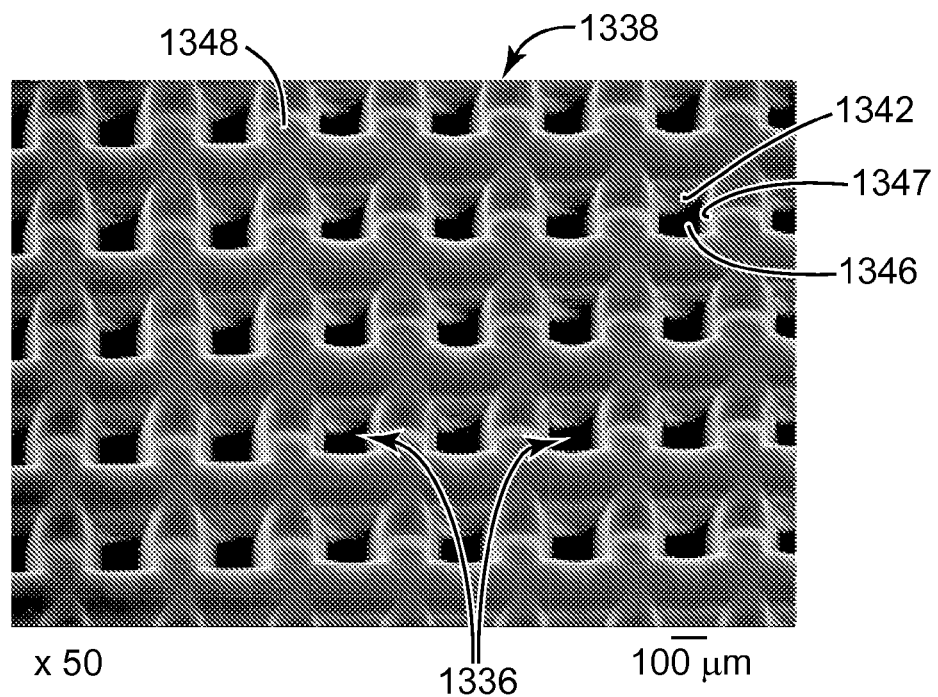
FIG. 19F is an optical micrograph of a top surface of the substrate of FIGS. 19A-19E, taken at a magnification of 50×.
Figure 19G:
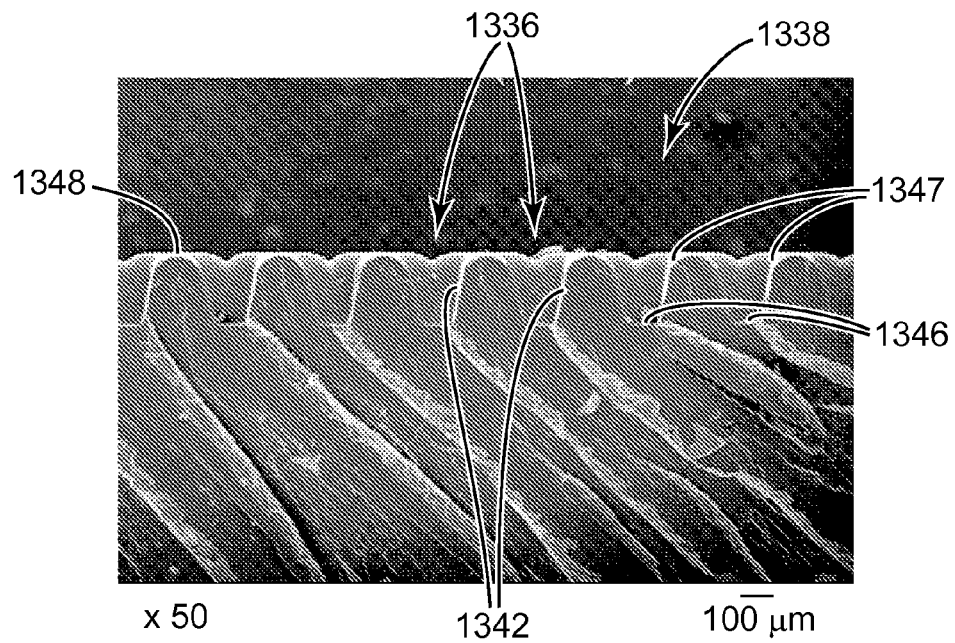
FIG. 19G is an optical micrograph of a cross-section of the substrate of FIGS. 19A-19F, taken at a magnification of 50×.
Figure 19H:
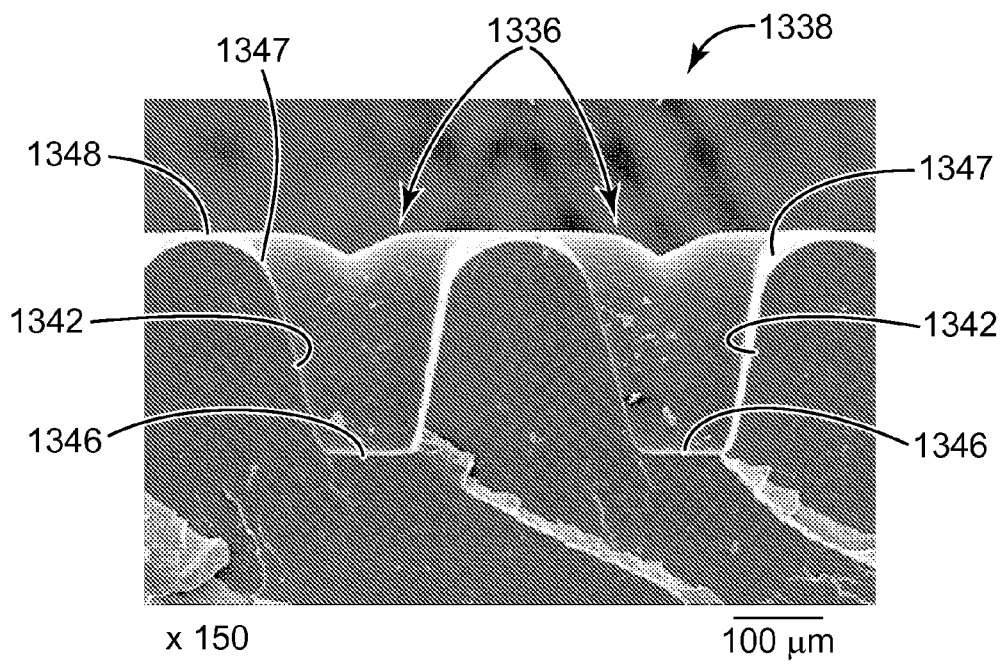
FIG. 19H is an optical micrograph of a cross-section of the substrate of FIGS. 19A-19G, taken at a magnification of 150×.

The optical micrographs of FIGS. 19F-19H also illustrate that in some embodiments, the open end 1347 can be at least partially smooth or rounded, which can have the advantages described above with respect to the substrate 1290.

The width of each base 1346 is represented by the letter "X", and the length is generally represented by the letter "Y" (see FIG. 19C). The pitch, or center-to-center distance between adjacent recesses 1336 is represented by the letter "P" (see FIG. 19C), and the vertical height, or depth, of each recess 1336 is represented by the letter "H" (see FIG. 19D).

As shown in FIG. 19E, in some embodiments, the flange 1392 of the substrate 1390 can include an angled top surface that is angled with respect to the horizontal by angle β. In addition, the total height or thickness of the substrate 1390 is represented in FIG. 19B by "$T_1$," and the height or thickness of the flange 1392 is represented in FIG. 19B by "$T_2$." Furthermore, by way of example only, the substrate 1390 is generally circular in shape, and the transverse dimension (e.g., diameter, in circular embodiments) "$X_1$" of the outer wall 1391 (or of the portion of the substrate 1390 including the outer wall 1391) is shown in FIG. 19B. In addition, the transverse dimension (e.g., diameter, in circular embodiments) "$X_2$" of the flange 1392 (or of the portion of the substrate 1390 including the flange 1392) is also shown in FIG. 19B.

A tool that is very similar to the tool 1250 of FIGS. 24A and 24B can be used to form the microstructured surface 1338, except that the tool used to form the microstructured surface 1338 would include pins that are arranged or packed to a higher packing density than that of the tool 1250.

Figure 20:
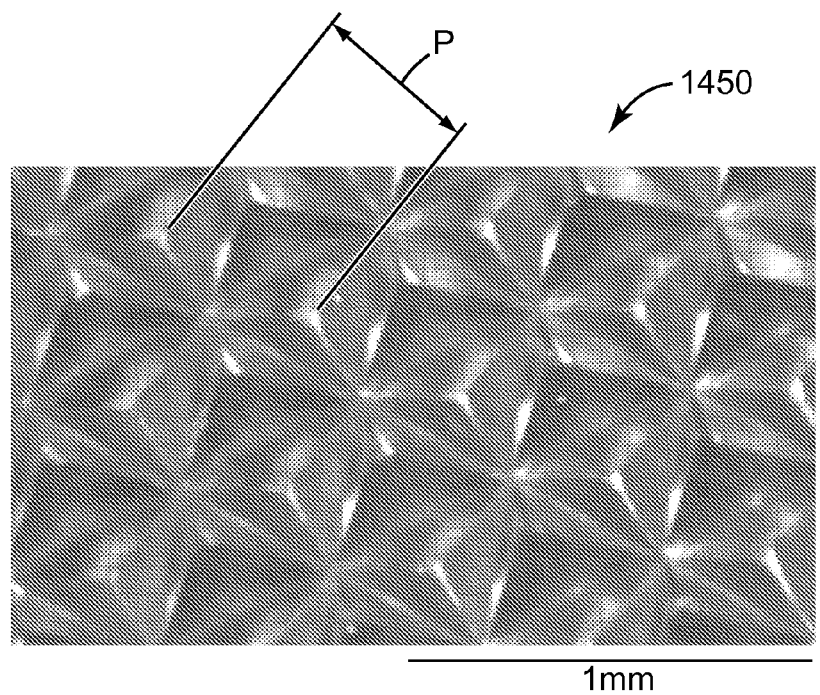
FIG. 20 is an optical micrograph of a tool used to form a microstructured surface according to one embodiment of the present disclosure.

In some embodiments, a microstructured surface can include inverted (i.e., upside down and hollow) cube-corner-shaped recesses, which can be replicated from male tooling, for example, using thermally-cured polydimethylsiloxane (PDMS; available under the trade designation SYLGARD® 184 from Dow Corning Corporation, Midland, Mich.). One example of such male tooling 1450 can include the cube-corner side of 3M™ DIAMOND GRADE™ prismatic retroreflective sheeting (available from 3M Company, St. Paul, Minn.), a scanning electron micrograph of which is shown in FIG. 20. For example, in some embodiments, the tooling 1450 can be placed in a container (e.g., a Petri dish) with the cube-corners pointing up. The materials for forming a microstructured surface (e.g., PDMS reagents) can be combined, if necessary, and poured onto the tooling 1450 (e.g., to an approximate thickness of 1 mm) to form a substrate. Bubbles can be removed by degassing in an enclosed chamber using repeated exposures to vacuum followed by exposures to atmospheric pressure. The container can optionally then be covered, and the microstructure material (e.g., PDMS) can be cured (e.g., at 80° C. for 2 hours). After curing, the substrate can be separated from the tooling 1450 to form a substrate comprising a microstructured surface including pyramidal (i.e., triangular, or three-sided, pyramidal) recesses. As shown in FIG. 20, in some embodiments, the center-to-center spacing, or "pitch" (P) of the tool can be 0.42 mm. However, other ranges for P given above can also be employed in the tooling 1450.

FIGS. 6 and 9-19H represent exemplary embodiments of various microstructured surfaces that can be used with the systems and methods of the present disclosure to isolate analyte(s) of interest from a sample, if present, and detect their presence while retained in the microstructured surface. The microstructured surfaces 138, 238, 338, 438, 538, 638, 737, 838, 938, 1038, 1138, 1238 and 1338 are shown by way of example only, but it should be understood that any combination of the microstructured surfaces 138, 238, 338, 438, 538, 638, 737, 838, 938, 1038, 1138, 1238 and 1338 can be employed in the systems and methods of the present disclosure. In addition, or alternatively, any other disclosed or equivalent microstructured surface can be used in the second portions 104 and 204 to retain a concentrate of a sample of interest that can be interrogated.

In some embodiments, the microstructured surface of the present disclosure (e.g., any of the above-described microstructures 138, 238, 338, 438, 538, 638, 737, 838, 938, 1038, 1138, 1238 and 1338, other suitable microstructures, or combinations thereof) can include "land areas" (e.g., the tops of the primary walls 342 or the secondary walls 372 of the microstructured surface 338 of FIG. 9 or the tops of walls 442 of the microstructured surface 438 of FIG. 10, etc.) between recesses (e.g., the primary recesses 336 of FIG. 9, the secondary recesses 366 of FIG. 9, the recesses 436 of FIG. 10, etc.). In some embodiments, such land areas can be modified to facilitate movement of the sample (or portions thereof, such as the more dense matter) into the recesses. For example, as mentioned above, in some embodiments, the land areas can be modified to be pointed, convex, radiused, curved, arcuate, tapered (e.g., away from the bottoms or bases of the recesses) or otherwise shaped to encourage fluid movement into the recesses. In addition, or alternatively, such land areas can be formed of a material that is, or is modified (e.g., by surface treatment) to be, more hydrophobic than the surfaces forming the interior of the recesses, such that an aqueous sample would have greater affinity for the recesses than the land areas to inhibit drops of the sample from getting hung up on the land areas, or other undesirable portions of the microstructured surfaces. U.S. Pat. No. 6,391,578 describes methods and devices for partitioning samples using hydrophilic liquid-retaining zones and hydrophobic land areas, and is incorporated herein by reference in its entirety.

FIGS. 11-19H illustrate microstructured surfaces 538, 638, 737, 838, 938, 1038, 1138, 1238, 1338 that were used in the Examples section below. As a result, the specific dimensions and details of such microstructures that were tested in the Examples are shown in Table 1 in the Examples section below.

However, it should be understood that in some embodiments, the dimensions, volumes, angles, shapes, well densities, and configurations can vary from what is disclosed in the Examples, and can fall within the ranges given above for such variables.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

The following embodiments are intended to be illustrative of the present disclosure and not limiting.

EMBODIMENTS

Embodiment 1 is a method for detecting an analyte of interest in a sample, the method comprising:
provide a first container comprising a filter portion, the filter portion comprising a filter configured to retain the analyte of interest from the sample, the filter having a first side and comprising a filtrand of the sample on the first side;
coupling the filter portion to a detection portion to form a second container, the detection portion comprising a microstructured surface, the filter portion and the detection portion being coupled together such that the first side of the filter faces the microstructured surface of the detection portion;
centrifuging the second container toward the microstructured surface to move the filtrand from the filter to the microstructured surface of the detection portion to form a sediment and a supernatant of the sample; and
inverting the second container, after centrifuging the second container, to decant at least a portion of the supernatant from the detection portion, such that a concentrate of the sample is retained in the microstructured surface of the detection portion of the second container, the concentrate comprising the sediment.

Embodiment 2 is the method of embodiment 1, further comprising interrogating the concentrate in the microstructured surface for the analyte of interest.

Embodiment 3 is a method for detecting the presence of an analyte of interest in a sample, the method comprising:
providing a first container comprising a receptacle portion adapted to contain the sample and a filter portion adapted to be removably coupled to the receptacle portion, the filter portion comprising a filter configured to retain the analyte of interest from the sample, the filter having a first side;
filtering the sample by moving the sample in a first direction from the receptacle portion toward the first side of the filter to form a filtrand of the sample on the first side of the filter, while removing a filtrate of the sample;
decoupling the receptacle portion and the filter portion of the first container;
coupling the filter portion to a detection portion to form a second container, the detection portion comprising a microstructured surface, the filter portion and the detection portion being coupled together such that the first side of the filter faces the microstructured surface of the detection portion;
centrifuging the second container to move the filtrand in a second direction from the filter to the microstructured surface of the detection portion of the second container to form a sediment and a supernatant of the sample, the second direction being different from the first direction;
inverting the second container, after centrifuging the second container, to decant at least a portion of the supernatant of the sample from the detection portion, such that a concentrate of the sample is retained in the microstructured surface of the detection portion, the concentrate comprising the sediment; and
interrogating the concentrate in the microstructured surface for the analyte of interest.

Embodiment 4 is a system for detecting an analyte of interest in a sample, the system comprising:
a first container comprising a filter portion, the filter portion comprising a filter, the filter having a first side and comprising a filtrand of the sample on the first side;
a second container comprising the filter portion coupled to a detection portion, the detection portion comprising a microstructured surface, the filter portion and the detection portion being coupled together such that the first side of the filter portion faces the microstructured surface of the detection portion, the microstructured surface of the detection portion adapted to receive a concentrate of the sample when the second container is exposed to a centrifugal force, the microstructured surface of the detection portion further adapted to retain at least a portion of the concentrate of the sample under normal gravitational forces.

Embodiment 5 is a system for detecting an analyte of interest in a sample, the system comprising:
  a first container comprising
    a receptacle portion adapted to contain the sample, and
    a filter portion, the filter portion adapted to be removably coupled to the receptacle portion and comprising a filter, the filter having a first side and comprising a filtrand of the sample on the first side;
  a second container comprising the filter portion coupled to a detection portion, the detection portion comprising a microstructured surface, the filter portion and the detection portion being coupled together such that the first side of the filter portion faces the microstructured surface of the detection portion, the microstructured surface of the detection portion adapted to receive a concentrate of the sample when the second container is exposed to a centrifugal force, the microstructured surface of the detection portion further adapted to retain at least a portion of the concentrate of the sample under normal gravitational forces.

Embodiment 6 is the method of embodiment 3 or the system of embodiment 5, wherein the filter portion includes a first end comprising the filter and a second end adapted to be coupled to the receptacle portion and the detection portion.

Embodiment 7 is the method of embodiment 3 or 6 or the system of embodiment 5 or 6, further comprising a filter connection assembly configured to couple the receptacle portion and the filter portion together.

Embodiment 8 is the method of any of embodiments 3, 6, and 7 or the system of any of embodiments 5-7, further comprising a filter connection assembly coupled between the receptacle portion and the filter portion of the first container.

Embodiment 9 is the method of embodiments 2-3 and 6-8, wherein interrogating the concentrate in the microstructured surface includes interrogating for at least one of absorbance, transmittance, fluorescence, chemiluminescence, and a combination thereof.

Embodiment 10 is the method of any of embodiments 2-3 and 6-9, wherein interrogating the concentrate in the microstructured surface includes optically interrogating the concentrate in the microstructured surface.

Embodiment 11 is the method of embodiment 10, wherein optically interrogating includes interrogating the concentrate in the microstructured surface for fluorescence.

Embodiment 12 is the method of embodiment 10 or 11, wherein optically interrogating includes
  directing electromagnetic energy toward the concentrate in the microstructured surface at a first frequency, and
  detecting electromagnetic energy emitted from the concentrate in the microstructured surface at a second frequency.

Embodiment 13 is the method of embodiment 10, wherein optically interrogating includes interrogating the concentrate colorimetrically.

Embodiment 14 is the method of embodiment 10 or 13, wherein optically interrogating includes
  emitting electromagnetic energy at the concentrate in the microstructured surface at a broad range of frequencies, and
  detecting at least one of the transmittance and the absorbance of at least a portion of the concentrate in the microstructured surface.

Embodiment 15 is the method of any of embodiments 10-14, wherein optically interrogating the concentrate in the microstructured surface includes optically scanning the microstructured surface.

Embodiment 16 is the method of any of embodiments 10-15, wherein optically interrogating the concentrate in the microstructured surface includes imaging the microstructured surface.

Embodiment 17 is the method of any of embodiments 2-3 and 6-16, wherein interrogating the concentrate in the microstructured surface includes detecting light that is indicative of the analyte of interest.

Embodiment 18 is the method of any of embodiments 2-3 and 6-17, wherein interrogating the concentrate in the microstructured surface includes detecting light by absorbance, reflectance, or fluorescence.

Embodiment 19 is the method of any of embodiments 2-3 and 6-18, wherein interrogating the concentrate in the microstructured surface includes detecting the analyte of interest immunologically.

Embodiment 20 is the method of any of embodiments 2-3 and 6-19, wherein interrogating the concentrate in the microstructured surface includes detecting the analyte of interest genetically.

Embodiment 21 is the method of any of embodiments 2-3 and 6-20, wherein interrogating the concentrate in the microstructured surface includes detecting an enzyme released from a live cell in the sample.

Embodiment 22 is the method of any of embodiments 2-3 and 6-21, wherein interrogating the concentrate in the microstructured surface includes detecting the analyte of interest colorimetrically, fluorimetrically, luminetrically, or a combination thereof.

Embodiment 23 is the method of any of embodiments 2-3 and 6-22, wherein the microstructured surface is formed in a first side of the detection portion, and wherein interrogating the concentrate in the microstructured surface includes interrogating the concentrate in the microstructured surface from the first side of the detection portion.

Embodiment 24 is the method of any of embodiments 2-3 and 6-22, wherein the microstructured surface is formed in a first side of the detection portion and the first side is positioned to face the filter portion during centrifugation, wherein the detection portion further comprises a second side opposite the first side, and wherein interrogating the concentrate in the microstructured surface includes interrogating the concentrate in the microstructured surface from the second side of the detection portion.

Embodiment 25 is the method of embodiment 24, wherein the second side of the detection portion includes an optical window that is substantially transparent.

Embodiment 26 is the method of embodiment 25, wherein the optical window is coextensive with at least a portion of the microstructured surface.

Embodiment 27 is the method of embodiment 25 or 26, wherein the microstructured surface comprises a plurality of microstructured recesses, each recess having a base, and wherein each base is substantially transparent, such that the contents of the plurality of microstructured recesses are visible from the second side of the detection portion.

Embodiment 28 is the method of embodiment 27, wherein at least one of the plurality of microstructured recesses includes a sidewall, and wherein the sidewall is substantially non-transparent.

Embodiment 29 is the method of any of embodiments 2-3 and 6-28, wherein the filter portion and the detection portion of the second container remain coupled together during the centrifuging step, the inverting step, and the interrogating step.

Embodiment 30 is the method of any of embodiments 2-3 and 6-29, wherein interrogating the concentrate in the microstructured surface occurs while the detection portion of the second container remains coupled to the filter portion of the second container, such that the supernatant serves as a humidity reservoir.

Embodiment 31 is the method of any of embodiments 2-3 and 6-30, wherein the supernatant resides in the second container during the interrogating step to serve as a humidity reservoir.

Embodiment 32 is the method of any of embodiments 1-3 and 6-31, further comprising adding an elution solution to the filter portion, the elution solution adapted to elute the filtrand from the filter.

Embodiment 33 is the method of embodiment 32, wherein adding an elution solution to the filter portion occurs (i) prior to coupling the filter portion to a detection portion to form a second container and/or (ii) prior to centrifuging.

Embodiment 34 is the method of any of embodiments 1-3 and 6-33, further comprising agitating at least the filter portion of the second container prior to centrifuging, wherein agitating aids in removing the filtrand from the filter.

Embodiment 35 is the method of any of embodiments 1-3 and 6-34, further comprising adding a diluent to the filter portion prior to centrifuging the second container.

Embodiment 36 is the method of embodiment 35, further comprising agitating the second container prior to centrifuging the second container.

Embodiment 37 is the method of embodiment 36, wherein agitating occurs when the second container is in a first orientation, and wherein centrifuging occurs in a second orientation, wherein the second orientation is different from the first orientation.

Embodiment 38 is the method of any of embodiments 1-3 and 6-37, further comprising incubating the container prior to centrifuging to grow microorganisms in the sample, if present.

Embodiment 39 is the method of any of embodiments 1-3 and 6-38, wherein inverting the container includes inverting the container at a rotational speed of no greater than 0.3 rpm.

Embodiment 40 is the method of any of embodiments 1-3 and 6-38, wherein inverting the container includes inverting the container at a rotational speed of no greater than 0.2 rpm.

Embodiment 41 is the method of any of embodiments 1-3 and 6-40, further comprising:
  decoupling the detection portion from the filter portion of the second container, after inverting the second container; and
  sealing the microstructured surface to inhibit evaporation.

Embodiment 42 is the method of any of embodiments 1-3 and 6-41, further comprising decoupling the filter portion and the detection portion of the second container, after centrifuging.

Embodiment 43 is the method of any of embodiments 1-3 and 6-42, wherein the analyte is detected in the concentrate in no greater than 8 hours, if the analyte of interest is present in the sample.

Embodiment 44 is the method of any of embodiments 1-3 and 6-43, wherein the analyte is detected in the concentrate in no greater than 3 hours, if the analyte of interest is present in the sample.

Embodiment 45 is the method of any of embodiments 1-3 and 6-43 or the system of any of embodiments 4-8, wherein the analyte is selected from the group consisting of an enzyme, a coenzyme, an enzyme substrate, an indicator dye, a stain, and a combination thereof.

Embodiment 46 is the method of any of embodiments 1-3 and 6-45 or the system of any of embodiments 4-8 and 45, wherein the analyte is selected for detecting the presence or absence of *Escherichia coli* or other coliforms.

Embodiment 47 is the method of any of embodiments 1-3 and 6-46 or the system of any of embodiments 4-8 and 45-46, wherein the analyte comprises a reagent for detecting ATP.

Embodiment 48 is the method of any of embodiments 1-3 and 6-47 or the system of any of embodiments 4-8 and 45-47, wherein the analyte comprises a reagent for detecting Adenylate Kinase.

Embodiment 49 is the method of any of embodiments 1-3 and 6-48 or the system of any of embodiments 4-8 and 45-48, wherein the analyte comprises luciferase or luciferin.

Embodiment 50 is the method of any of embodiments 1-3 and 6-49 or the system of any of embodiments 4-8 and 45-49, wherein the filter portion is removably coupled to the detection portion.

Embodiment 51 is the method of any of embodiments 1-3 and 6-50 or the system of any of embodiments 4-8 and 45-50, wherein the filter portion includes a first end comprising the filter and a second end adapted to be coupled to the detection portion, and wherein the detection portion has a first end comprising the microstructured surface and a second end adapted to be coupled to the filter portion.

Embodiment 52 is the method of any of embodiments 1-3 and 6-51 or the system of any of embodiments 4-8 and 45-51, wherein the detection portion has a first end comprising the microstructured surface and a second end adapted to be coupled to the filter portion.

Embodiment 53 is the method of any of embodiments 1-3 and 6-52 or the system of any of embodiments 4-8 and 45-52, wherein the microstructured surface comprises a plurality of microstructured recesses, and wherein the concentrate is retained in at least one of the plurality of microstructured recesses.

Embodiment 54 is the method of any of embodiments 1-3 and 6-53 or the system of any of embodiments 4-8 and 45-53, wherein the microstructured surface is formed in a first side of the detection portion and the first side is positioned to face the filter portion during centrifugation, wherein the detection portion further comprises a second side opposite the first side, and wherein the second side of the detection portion includes an optical window that is substantially transparent.

Embodiment 55 is the method or system of embodiment 54, wherein the optical window is coextensive with at least a portion of the microstructured surface.

Embodiment 56 is the method of any of embodiments 1-3 and 6-55 or the system of any of embodiments 4-8 and 45-55, wherein the microstructured surface is formed in a first side of the detection portion and the first side is positioned to face the filter portion during centrifugation, wherein the detection portion further comprises a second side opposite the first side, and wherein the microstructured surface comprises a plurality of microstructured recesses, each recess having a base, and wherein each base is substantially transparent, such that the contents of the plurality of microstructured recesses are visible from the second side of the detection portion of the container.

Embodiment 57 is the method or system of embodiment 56, wherein at least one of the plurality of microstructured recesses includes a sidewall, and wherein the sidewall is substantially non-transparent.

Embodiment 58 is the method of any of embodiments 1-3 and 6-57 or the system of any of embodiments 4-8 and 45-57, further comprising a diluent positioned in the second container when the filter portion and the detection portion are coupled together, wherein the diluent serves as a humidity reservoir.

Embodiment 59 is the method of any of embodiments 1-3 and 6-58 or the system of any of embodiments 4-8 and 45-58, wherein the microstructured surface includes a recess density of at least about 100 recesses per square centimeter.

Embodiment 60 is the method of any of embodiments 1-3 and 6-59 or the system of any of embodiments 4-8 and 45-59, wherein the microstructured surface includes a recess density of at least about 800 recesses per square centimeter.

Embodiment 61 is the method of any of embodiments 1-3 and 6-60 or the system of any of embodiments 4-8 and 45-60, wherein the microstructured surface includes a recess density of at least about 3000 recesses per square centimeter.

Embodiment 62 is the method of any of embodiments 1-3 and 6-61 or the system of any of embodiments 4-8 and 45-61, wherein at least a portion of the microstructured surface includes a static water surface contact angle of at least 65 degrees.

Embodiment 63 is the method of any of embodiments 1-3 and 6-62 or the system of any of embodiments 4-8 and 45-62, wherein at least a portion of the microstructured surface includes a static water surface contact angle of at least 95 degrees.

Embodiment 64 is the method of any of embodiments 1-3 and 6-63 or the system of any of embodiments 4-8 and 45-63, wherein the microstructured surface comprises a plurality of recesses, and wherein at least one of the plurality of recesses has a frusto-pyramidal shape.

Embodiment 65 is the method of any of embodiments 1-3 and 6-64 or the system of any of embodiments 4-8 and 45-64, wherein the microstructured surface comprises a plurality of recesses, and wherein each of the plurality of recesses contains a volume of no greater than 1 microliter.

Embodiment 66 is the method of any of embodiments 1-3 and 6-65 or the system of any of embodiments 4-8 and 45-65, wherein the microstructured surface comprises a plurality of recesses, wherein the plurality of recesses define a collective volume, and wherein the collective volume is no greater than 100 microliters.

Embodiment 67 is the method of any of embodiments 1-3 and 6-66 or the system of any of embodiments 4-8 and 45-66, wherein the microstructured surface comprises a plurality of recesses, and wherein at least one of the plurality of recesses comprises a reagent.

Embodiment 68 is the method or system of embodiment 67, wherein the reagent includes at least one of a substrate, an enzyme, a growth reagent, a lysis reagent, or a combination thereof.

Embodiment 69 is the method of any of embodiments 1-3 and 6-68 or the system of any of embodiments 4-8 and 45-68, wherein the analyte of interest includes at least one of E. coli and coliforms.

Embodiment 70 is the method of any of embodiments 1-3 and 6-69 or the system of any of embodiments 4-8 and 45-69, wherein the sample is water.

Embodiment 71 is the method of any of embodiments 1-3 and 6-70 or the system of any of embodiments 4-8 and 45-70, wherein the filter includes at least one of a polyolefin porous membrane, an ethylene-chlorotrifluoroethylene copolymer porous membrane, a polyacrylonitrile porous membrane, a polycarbonate porous membrane, a polyester porous membrane, a cellulose ester porous membrane, a polyamide porous membrane, a polyethersulfone porous membrane, a polysulfone porous membrane, a polyvinylidene fluoride (PVDF) porous membrane, a polyacrylonitrile nanofiber membrane, a PVDF nanofiber membrane, a cellulose ester nanofiber membrane, a polyvinyl acetate or alcohol nanofiber membrane, or a polyvinyl butyral nanofiber membrane, or a combination thereof.

Embodiment 72 is the method of any of embodiments 1-3 and 6-71 or the system of any of embodiments 4-8 and 45-71, wherein the filter includes at least one of
a membrane formed by a thermally induced phase separation (TIPS) process, and
a nanofiber membrane.

Embodiment 73 is the method of any of embodiments 1-3 and 6-72 or the system of any of embodiments 4-8 and 45-72, wherein the filter includes multiple zones of porosity, and wherein the first side of the filter comprises the smallest pore zone.

The following working and prophetic examples are intended to be illustrative of the present disclosure and not limiting.

EXAMPLES

Definitions

MS: Microstructured Surface
Microstructure: The microstructures are wells formed in the surface of a thermoplastic or thermoset material. Each well is characterized by a two-dimensional (e.g., cross-sectional) shape (e.g., square, hexagon, circle) having a top opening, one or more sidewalls and a bottom. The volume, in nanoliters (nL) of each well is defined by the area of the top and bottom, measured as the distance in micrometers (μm) through the center point from one edge to the opposite edge and the depth—the distance in μm from the top of the well to the bottom of the well.
Draft angle α (Angle) in degrees: the angle formed by a line perpendicular to the bottom of the well and a sidewall of the well.
Density: The number of wells in one square centimeter of the surface
Pitch: the spacing in μm of the wells from a point on one well to the same point on an adjacent one (e.g., center-to-center spacing).
Onset: the time at which fluorescence is first observed on an image. Images of the microstructures are taken at fixed intervals, e.g., after 1 hour, 2 hours, 3 hours, etc. The times recorded in the examples represent the time at which the fluorescence was first observed in an image. The actual onset is a time between the image exhibiting fluorescence and the previous image.
Cap: centrifuge tube cover having threads for securing to a tube.
Lid: planar centrifuge tube or bottle cover secured to a tube using a friction fit.
Materials and Instruments
Polymers obtained from Topas Advanced Polymers Gmbh; Florence Ky.:
COC1—transparent cyclic olefin copolymer; Topas™ 8007X10

COC2—transparent cyclic olefin copolymer, high moisture barrier; Topas™ 8007S-04

COP—transparent cyclo olefin polymer; Zeonor™ 1430R; Zeon Chemicals L.P.; Louisville Ky.

PC—Lexan polycarbonate; HPS1R; SABIC Americas Corp.; Houston Tex.

PMMA—WF100 poly(methyl methacrylate); Mitsubishi Rayon Co Ltd, Tokyo, Japan

PP—polypropylene 5724; Total Petrochemicals; Houston, Tex.

Colilert™ media—Colilert™ coliform/E. coli test media; IDEXX Laboratories, Inc.; Westbrook, Me. The media was prepared for the examples by mixing the media from a Snap Pack for a 100 mL sample in 100 mL of sterile water.

Readycult® media—Readycult® Coliforms 100 coliform/E. coli test media; EMD Chemicals; Gibbstown, N.J. The media was prepared for the examples by mixing the media from a Snap Pack for a 100 mL sample in 100 mL of sterile water.

Filter A—30 mm diameter to fit device used, 0.34 µm multi-zone TIPS membrane coated with polyethylene glycol (R1933-7/PEG) prepared according to the examples and description of International Patent Application Serial No. US2011/039220, entitled "Filtration Methods and Devices" filed Jun. 6, 2011, (U.S. Provisional Patent Application Ser. No. 61/352,229, filed Jun. 7, 2010). The membranes were coated with polyethylene glycol (PEG) using the materials and procedures described in U.S. Provisional Patent Application Ser. No. 61/350,154, entitled "PROCESS FOR MAKING COATED POROUS MATERIALS," filed Jun. 1, 2010.

Filter B—30 mm diameter to fit device used, Isopore Membrane, polycarbonate—0.40 micrometer; Millipore, Billerica, Mass.

Filter C—30 mm diameter to fit device used, MF-Millipore Membrane, Type HAWP—mixed cellulose ester—0.45 micrometer; Millipore; Billerica Mass.

Centrifuge tube—50 mL Self-Standing centrifuge tube (No. 430921) with cap (CentriStar™ centrifuge cap) both obtained from Corning, Inc.; Corning, N.Y.

Multipurpose Centrifuge—multipurpose centrifuge (Model 5804) with a swinging bucket rotor (A-4-44), both manufactured by Eppendorf; Hauppauge N.Y.

Benchtop Centrifuge—benchtop centrifuge (Allegra 25R Refrigerated Benchtop Centrifuge) with swinging bucket rotor (TS-5.1-500), both from Beckman Coulter, Inc., Brea, Calif.

Imaging system—illuminated/fluorescent stereo microscope model SteREO Lumar.V12 using either illuminated light (Illuminated Imager) or fluorescent light (Fluorescent Imager); images were captured with an AxioCam MRc 5 camera and the AxioVision Release 4.6.3 program, all obtained from Carl Zeiss Microimaging, Inc., Thornwood N.J.

Vacuum assembly—AIR CADET Vacuum/Pressure Station, Model No. 420-3901; Barnant Company; Barrington Ill.

Preparation of Microstructures

1—Cast PDMS (MS1)

An array of cylindrically shaped micro projections was prepared by forming a pattern on a photoresist coated silicon wafer and wet chemical etching. A Microstructured Surface MS1 having the inverse structure of the array (wells) was prepared by placing the etched silicon wafer in a 100 mm×15 mm Petri dish (catalog number 25384-302; VWR International, West Chester, Pa.). A thermally curable polydimethylsiloxane composition was prepared by mixing polydimethylsiloxane (PDMS available under the trade designation SYLGARDB 184 from Dow Corning Corporation, Midland, Mich.) reagents in a 10:1 weight ratio and pouring onto the etched silicon wafer to a thickness of about 1 millimeter. Bubbles were removed from the PDMS by placing the dish in a glass dessicator jar and exposing to vacuum (600 mm Hg) followed by exposure to atmospheric pressure. This process was repeated three times. The dish was removed from the dessicator, covered with a lid, and the PDMS cured at 80° C. for 2 hours.

After curing the PDMS with an array of micro cavities formed on the surface was separated from the silicon wafer. The physical dimensions of each cavity, or well, are shown in Table 1. An optical micrograph, shown in FIG. 11, of the PDMS replicated structure was taken using the Illuminated Imager at a 25× magnification.

2—Cast Polypropylene Films (MS2A-MS2F)

Molten polypropylene resin (DOW C700-35N PolyPropylene Resin DA, Dow Automotive, Auburn Hills, Mich.) was cast onto a master tool roll to form films having microstructured surfaces. The general procedure for casting a resin with a microstructured surface is described in U.S. Pat. No. 6,617,002 (Wood). A different tool was used to mold each surface MS2A-MS2F shown in Table 1. The physical dimensions of the microstructured surfaces on the tools for surfaces MS2C, MS2D, and MS2F are shown in Table 2. The cast polypropylene sheets with microstructured surfaces were about 0.1 to 0.5 mm thick.

Optical micrographs of polypropylene sheets with replicated structures MS2-MS2F were taken using the Illuminated Imager at a 25× magnification and are shown in FIGS. 12-17, respectively. The physical dimensions of the structures on the sheets are shown in Table 1: MS (microstructured surface); Density (well density in number of features/square centimeter); Shape (shape of structures in the sheet); Pitch (center to center spacing); Top (dimension across top in µm); Bottom (dimension across bottom in µm); Depth (dimension from top of well to bottom of well in µm); Angle (draft angle in degrees); and volume of each well in nanoliters (nL).

3—Injection Molded Lids (MS3A-MS3B)

Electronic discharge machining (EDM) was used to make insert tools comprising an array of square posts for injection molding lids having a microstructured surface MS3A (FIGS. 18A-18H) and MS3B (FIGS. 19A-19H) with the physical dimensions shown in Table 1. The physical dimensions of the microstructured surface on the tool for surface MS3A are shown in Table 2. For each microstructure the insert tool was assembled in a mold base to produce a lid having the microstructure on the interior surface, with a flange around the periphery for coupling to the top of a centrifuge tube. The non-structured side of the lid was flat. The mold was designed such that the insert tool for molding the microstructured surface was interchangeable with other insert tools to mold lids having various microstructured surfaces, e.g., with varying well densities, sizes and shapes of structures, etc.

Lids 24 mm in diameter with a flange around the periphery were injection molded with a microstructured surface, MS3A or MS3B, in a KraussMaffei injection molding machine (Model K65-CX; KraussMaffei technologies; Munich, Germany) with various resins, COC1, COC2, COP, PP, PMMA, and PC. The resin pellets for each lid were melted (COC1, COC2 and COP at 232 to 238° C., PP at 204 to 215° C., PC at 285 to 288° C., PMMA at 215 to 227° C.)

and then injected at 16,000 psi. The mold temperature was held at 38° C. for PP, 66° C. for COC1, COC2, and PMMA, and 71° C. for PC and the injection time was 0.78 sec for all resins. Each lid was molded individually. The physical properties of the microstructured surfaces (MS3A and MS3B) are shown in Table 1.

TABLE 1

Physical Dimensions of Microstructured Surfaces (MS)

| MS | FIG. | Density/sq cm | Shape | Pitch (μm) | Top (μm) | Bottom (μm) | Depth (μm) | Calculated draft Angle (degrees) | Volume nL | Aspect Ratio** |
|---|---|---|---|---|---|---|---|---|---|---|
| 1 | 11 | 1600 | Circular | 250 | 200 | 200 | 100 | 0 | 3 | 0.50 |
| 2A | 12 | 31 | Square | 1796 | 300 | 100 | 325 | 17 | 14 | 1.08 |
| 2B | 13 | 74 | Hexagonal | 1160 | 344* | 200⁺ | 254 | 16 | 14 | 0.74 |
| 2C | 14 | 149 | Square | 820 | 254 | 100 | 254 | 17 | 8 | 1.00 |
| 2D | 15 | 286 | Square | 592 | 254 | 100 | 254 | 17 | 8 | 1.00 |
| 2E | 16 | 930 | Hexagonal | 338 | 344* | 200⁺ | 254 | 16 | 14 | 0.74 |
| 2F | 17 | 3720 | Square | 165 | 120 | 76 | 127 | 10 | 1 | 1.06 |
| 3A | 18A-18H | 151 | Square | 813 | 228 | 100 | 254 | 14 | 7 | 1.11 |
| 3B | 19A-19H | 826 | Square | 348 | 228 | 100 | 254 | 14 | 7 | 1.11 |

*inscribed distance (diameter of a circle inscribed in a hexagon)
⁺diameter of circular base; tips of tools used were circular
**Aspect ratio (depth divided by top dimensions)

TABLE 2

Tool Dimensions* for FIGS. 21A-24B

| MS | Tool | FIGS. | $X_t$ inches (μm) | $Y_t$ inches (μm) | $X_b$ inches (μm) | P inches (μm) | d inches (μm) | $H_r$ inches (μm) | $H_T$ inches (μm) | α (°) | Aspect Ratio** |
|---|---|---|---|---|---|---|---|---|---|---|---|
| 2C | 850 | 21A-21B | 0.0037 (94) | 0.0037 (94) | 0.010 (250) | 0.0323 (820) | 0.022 (560) | 0.002 (50) | 0.017 (430) | 12.5 | 1.72 |
| 2D | 950 | 22A-22B | 0.0037 (94) | 0.0037 (94) | 0.010 (250) | 0.0233 (592) | 0.014 (360) | 0.002 (50) | 0.017 (430) | 12.5 | 1.72 |
| 2F | 1150 | 23A-23B | 0.0030 (76) | 0.0030 (76) | 0.0047 (120) | 0.0065 (160) | 0.0017 (43) | N/A | 0.005 (120) | 10 | 1.0 |
| 3A | 1250 | 24A-24B | 0.0040 (~100) | 0.0040 (~100) | 0.009 (228) | 0.0320 (813) | 0.023 (580) | N/A | 0.010 (250) | 10 | 1.10 |

*Dimensions were taken from the design drawings for the tools.
**Aspect ratio (depth divided by base dimensions).

Preparation of Microstructured Centrifuge Tube Closures

Cap 1—Adhered Film Disks

Circular disks 24 mm in diameter were die cut using a hole punch from each of the films having microstructured surfaces MS1 or MS2A-MS2F (Table 3). Each disk was adhered to the underside of a flat centrifuge tube cap using a silicone polyurea transfer adhesive, prepared according to the procedure described in U.S. Pat. No. 6,730,397 (Melancon et al.), which is incorporated herein by reference in its entirety. To prevent leaking during centrifugation, a one-inch internal diameter O-ring gasket having a round, 0.100-inch cross section (Part number AS568A-120; Grainger, Inc., Lake Forest, Ill.) was placed in the outer groove of the cap. The cap was used to close a 50-mL centrifuge tube.

Lid 1—Transparent Lid with Adhered Film Disks

Transparent friction fit lids were assembled by first machining 24 mm diameter circular disks from 3-4 mm thick sheets of clear cyclic olefin polymer (COC1) and clear poly(methyl methacrylate) polymer (Plexiglas; Altuglas International; Bristol Pa.). Circular disks (24 mm in diameter) were cut from polypropylene films having microstructured surfaces MS2A-MS2F and adhered to the underside of the transparent lids with the silicone urea transfer adhesive of Cap1. A groove was machined in the outer periphery of the lid and an O-ring was placed in the groove to provide a tight seal and to prevent leaking during centrifuging. To further secure the lid and to provide a viewing window, a 24 mm diameter hole was punched in the center of a centrifuge tube cap, which was threaded on to the tube and tightened against the lid. While both COC1 and PMMA performed adequately to provide a transparent substrate to view the microstructure from outside the tube, the COC1 had a lower fluorescence background in UV-region and higher transmission in the UV-region.

Lid 2—Transparent Injection Molded Lid

Transparent lids with microstructured surfaces (MS3A and MS3B) were injection molded using various polymers (COC1, COC2, COP, PC, PMMA, and PP) as described above. The lids were used to seal 50-mL centrifuge tubes and the tubes were further secured using the regular centrifuge tube caps when centrifuging. A 24 mm diameter hole was punched in the center of each cap so that when the cap and lid were placed on a centrifuge tube, microstructured surface could be viewed and/or imaged though the transparent lid without opening the tube.

Preparation of Bacterial Cultures for Testing

Bacterial cultures used in the examples are shown in Table 3 and were obtained from American Tissue Culture Collection (ATCC); Manassas, Va.

TABLE 3

Bacteria strains used in examples

| Bacteria | ATCC No. |
|---|---|
| Escherichia coli | 51813 |
| Citrobacter freundii | 14135 |
| Enterobacter aerogenes | 29007 |
| Klebsiella pneumonia | 4352 |
| Enterococcus faecalis | 700802 |

A culture for testing was prepared by inoculating a pure culture of a target bacteria strain from Table 1 into TSB (BD Tryptic Soy Broth; Bection, Dickinson and Co., Franklin Lakes, N.J.) and grown overnight at 37° C. The culture was diluted serially in Butterfield's phosphate buffer (Whatman Inc.; Piscataway, N.J.) to obtain the desired colony forming units (cfu) per milliliter desired for inoculating into water samples. Typically the final two serial dilutions containing about $10^1$-$10^2$ cfu/mL were used to prepare a sample for testing or plating. E. coli and other coliform bacteria concentrations were quantified for the bacterial dilutions using 3M™ Petrifilm™ E. coli/Coliform Count Plates. E. faecalis was quantified using 3M™ Petrifilm™ Aerobic Count Plate (both available from 3M Co., St. Paul, Minn.). The plates were prepared and used according to manufacturer's instruction and incubated overnight at 37° C. The plates were read using a 3M PETRIFILM Plate Reader (3M Co.) to determine the cfu/mL.

Preparation of Sugar Dye Substrate Culture Media

A culture medium was prepared by mixing 5 grams (g) of tryptose (Difco laboratories, Detroit, Mich.), 5 g of sodium chloride, 1 g of sorbitol, 1 g of tryptophan, 2.7 g of di-potassium hydrogen phosphate, 2 g of potassium di-hydrogen phosphate, and 0.1 g laurylsulfate sodium salt (all obtained from Sigma Aldrich, St. Louis, Mo.) with 1000 mL of double distilled water. The culture media was autoclaved at 121° C. for 15 min.

Dye substrates shown in Table 4 were dissolved in DMSO (Dimethyl sulfoxide (DMSO, Sigma Aldrich, St. Louis, Mo.) to form a solution containing 100 milligrams sugar substrate per milliliter of DMSO. The substrate solution was added to the culture media to provide a final concentration of 40 micrograms of sugar substrate/milliliter of culture medium (μg/mL).

TABLE 4

Sugar-dye substrates

| Name | Abbreviation | Excitation Wavelength (nm) | Emission Wavelength (nm) |
|---|---|---|---|
| Sugar-dye substrates obtained from Marker Gene Technologies, Eugene OR | | | |
| 4-Methylumbelliferyl β-D-galactopyranoside | Mu-Gal | 350 | 450 |
| 4-Methylumbelliferyl β-D-glucuronide | Mu-GlcU | 350 | 450 |
| Fluorescein di-β-D-galactopyranoside | Flu-di-Gal | 485 | 520 |
| Resorufin β-D-galactopyranoside | Res-Gal | 530 | 590 |
| Sugar-dye substrates obtained from MP Biomedical, Solon OH | | | |
| Resorufin β-D-glucuronide | Res-GlcU | 530 | 590 |
| Synthesized according to Chilvers et al, (J. Appl. Microbiol. 2001, 91, 1118-1130) | | | |
| Ethyl-7-hydroxycoumarin-3-carboxylate-β-D-galactopyranoside | MHC-Gal | 400 | 450 |
| Synthesized according to U.S. Pat. No. 6,566,508 (Bentson et al.) | | | |
| 3-(thiophen-2-yl)-umbelliferone-β-D-galactopyranoside | TU-Gal | 425 | 500 |

Note:
Three samples were generally prepared and tested for the Reference Example and for each example. While the example is described in singular, three replicates were generally prepared and tested. Counts are reported as the average of the results. Onset of fluorescence records the first instance that fluorescence was observed in an image.

Reference Example

Selection of Sugar Dye Substrates for E. coli/Coliform Detection a) Detection of E. coli Using Galactosidase Substrates Culture media with sugar enzyme substrates were prepared according to the procedure above and dispensed into a black 96-well optical bottom microtiter plate (Nalgene Nunc International, Rochester, N.Y.). An E. coli culture was prepared as described above and serially diluted to obtain desired amount of cfu per mL. The media in the 96-well plates were inoculated with 10 μl of serially diluted cells to obtain wells containing approximately 1 cfu, 10 cfu or 100 cfu in each wells and a minimum of three wells were used for each of the substrates. A control well was prepared with 10 microliters of Butterfield's buffer. The plates were incubated at 37° C. and read in a kinetic mode using a Tecan Infinite 200 PRO multimode reader (Tecan US, Inc. Durham, N.C.). The fluorescence intensity was recorded as a function of time. Time to detection was established as the time point where the signal was 50 times greater than the initial reading (background). Results are shown in Table 5. All the substrates tested showed fluorescence upon growth of E. coli and it took about 15 to 17 hr to detect 1 cfu of E. coli in 100 microliters.

TABLE 5

Detection of E. coli using galactosidase substrates

| | Time to detect E. coli (S/B ratio of 50:1) | | |
|---|---|---|---|
| Sugar Substrate | 1 cfu | 10 cfu | 100 cfu |
| MHC-gal | 15 hr | 10 hr | 7 hr |
| Mu-gal | 16 hr | 11 hr | 8 hr |
| Flu-di-gal | 16 hr | 11 hr | 8 hr |
| Tu-gal[1] | 17 hr | 12 hr | 10 hr |
| Res-gal | 15 hr | 10 hr | 8 hr |

[1]S/B Ratio only 5:1 b) Detection of Coliforms Using MHC-Gal

The procedure for the detection of E. coli outlined in example a) was repeated using the bacteria listed in Table 6.

The culture medium prepared with MHC-gal was dispensed into 96-well microtiter plates and inoculated with serially diluted cultures to obtain approximately 1 cfu, 10 cfu or 100 cfu in each of the wells. A minimum of three wells were used for each bacteria. The data in Table 6 indicates that MHC-gal is a suitable substrate for galactosidase for detecting of coliforms.

TABLE 6

Detection of coliforms using MHC-gal

| Bacteria | Time to detect coliforms (S/B ratio of 50:1) | | |
|---|---|---|---|
| | 1 cfu | 10 cfu | 100 cfu |
| E. coli | 13 hr | 12 hr | 10 hr |
| E. aerogenes | 15 hr | 13 hr | 10 hr |
| C. freundii | 13 hr | 12 hr | 8 hr |
| K. pneumonia | 17 hr | 13 hr | 10 hr | c) Detection of E. coli Using Combination of Glucuronidase and Galactosidase Substrates Culture medium was prepared, tested, and the resulting data was analyzed according to the procedure for detection of E. coli, except that a combination of glucuronidase substrates (Mu-GlcU or Res-GlcU) and galactosidase substrates (MHC-Gal or Flu-di-Gal or Res-Gal) was used as the sugar dye substrate as shown in Table 7. The culture medium was dispensed into 96-well microtiter plates and the wells were inoculated with serially diluted culture to obtain approximately 1 cfu, 10 cfu or 100 cfu. The data in Table 7 show that when a combination of two different substrates are used in a single well, the enzyme activities of the glucuronidase and galactosidase can each be detected by fluorescence at different times (hr). The reaction is detected sooner for higher bacteria concentrations.

TABLE 7

Detection of E. coli using glucuronidase and galactosidase substrates

| Sugar Dye Substrate | Glucuronidase | | | Galactosidase | | |
|---|---|---|---|---|---|---|
| | 1 cfu | 10 cfu | 100 cfu | 1 cfu | 10 cfu | 100 cfu |
| Mu-Glcu + Res-gal | 17 hr | 10 hr | 8.5 hr | 15 hr | 8.5 hr | 7.5 hr |
| Mu-Glcu + Flu-di-gal | 16 hr | 10 hr | 8.5 hr | 16 hr | 12 hr | 11 hr |
| Res-Glcu + Flu-di-gal | 17 hr | 8.5 hr | 7 hr | 16 hr | 12 hr | 11 hr |
| Res-Glcu + Mu-gal | 17 hr | 8.5 hr | 7 hr | 16 hr | 10 hr | 7.5 hr |
| Res-Glcu + MHC-gal | 16 hr | 8.5 hr | 7 hr | 15 hr | 9 hr | 7 hr |

Example 1

Concentration of Bacteria in Microstructures by Centrifugation

Bacterial suspensions of E. coli, E. aerogenes, and E. faecalis were each prepared in 10 mL of Butterfield's buffer (Whatman) to provide approximately $10^1$-$10^2$ cfu/mL of buffer, and transferred into 50 mL centrifuge tubes. Six tubes of each bacterial suspension were prepared and closed tightly with Cap 1 with microstructured film disks (MS2A to MS2F). The tubes were placed with the cap-down in a swinging bucket centrifuge rotor and centrifuged in the Multipurpose Centrifuge for 10 minutes at 4000 RPM (2800 g). The tube holder was modified to spin the tubes cap-down. After centrifuging, the tubes were removed and slowly inverted to allow excess supernatant buffer to drain off the surface of the microstructured film and back to the tube. A small portion of the buffer remained in the microstructures. The supernatant in each tube was filtered through a 0.45 µm mixed cellulose ester filter (HAWP02500, Millipore, Billerica, Mass.).

3M™ Petrifilm™ E. coli/Coliform Count Plates (used for E. coli and E. aerogenes) and 3M™ Petrifilm™ Aerobic Count (used for E. faecalis) were hydrated according to the manufacturer's instructions. The filters were carefully removed from the filter funnel with sterile forceps and placed on the appropriate hydrated plate, and the plates were incubated overnight at 37° C. The plates were read on a 3M™ Petrifilm™ Plate Reader (3M Co.; St, Paul Minn.) and/or manually to determine colony forming units (cfu). The percent recovery in the microstructures, i.e., the percentage of bacteria captured in the microstructures, was calculated by subtracting the cfu on the filter from the cfu that were in the initial 10 mL sample prior to centrifuging, dividing by the cfu in the initial 10 mL sample and multiplying by 100. The percent Recovery in Microstructures is shown for different well densities in Table 8.

TABLE 8

Percent recovery of bacteria in microstructured surfaces

| MS | Well Density/ sq cm | % Recovery in microstructures | | |
|---|---|---|---|---|
| | | E. coli | E. aerogenes | E. faecalis |
| 2A | 31 | 47 | 46 | 43 |
| 2B | 74 | 59 | 54 | 49 |
| 2C | 149 | 80 | 80 | 78 |
| 2D | 286 | 88 | 84 | 84 |
| 2E | 930 | 90 | 94 | 91 |
| 2F | 3720 | 92 | 89 | 85 |

Example 2

Detection of Bacteria in Cast PDMS Microstructures

An E. coli suspension containing approximately a total of 100 cfu (10 cfu/mL) was prepared in 10 mL of Colilert media and dispensed into a 50 mL centrifuge tube and closed tightly with Cap 1 prepared using cast PDMS with cylindrically shaped microstructured surface MS1. Control samples were prepared similarly, but received 100 µL of Butterfield's buffer. The centrifuge tube was then placed cap-down in the tube holder in a swinging bucket rotor in a multipurpose centrifuge (Centrifuge 1) and centrifuged for 20 minutes at 4000 RPM (2800 g). The tube holder was modified to spin the tubes cap-down. After centrifuging, the tubes were removed and slowly inverted to allow the media to drain back into the tube, leaving media in the microstructures held by capillary action and surface tension. The microstructured wells were then sealed with 24 millimeter diameter clear adhesive film (MicroAmp™ Optical Adhesive Film; Applied Biosystems; Foster City Calif.). The structures were incubated at 37° C. and imaged every hour through the tape using the Imager described under Materials and Instruments.

The same initial E. coli suspension was used to prepare 100 mL of Colilert media containing approximately a total of 100 cfu (1 cfu/mL) of bacteria. The solution was tested using a commercial water safety testing kit (Colilert Quantitray; IDEXX Laboratories, Inc.; Westbrook, Me.) according to the manufacturer's instructions. The Quantitray device has two zones, one with 200 microliter compartments and one with 2 mL compartments.

The cap with cast PDMS microstructures and the water safety tray were incubated at 37° C. and imaged each hour. Onset of fluorescence was observed in approximately 4 hours in the microcylinders compared with about 13 hours for the commercial device. No fluorescence was seen in control samples.

Example 3

Rapid Detection of Bacteria in Cast Polypropylene Microstructures

An *E. coli* suspension containing $10^1$-$10^2$ cfu was prepared in 10 mL of Colilert™ media, dispensed into 50 mL centrifuge tubes and the tubes were closed tightly using Cap1 with microstructured surfaces MS2A, B, C, D, E or F. Control samples were prepared similarly, but received 100 µL of Butterfield's buffer. The tubes were centrifuged and slowly inverted to allow the media to drain back into the tube. The caps were removed, and excess media was carefully removed from the edges of the caps using a tissue (Kimwipes). The microstructured surface containing small portions of media was then sealed with 24 millimeter diameter clear adhesive film (MicroAmp™ Optical Adhesive Film; Applied Biosystems) and incubated at 37° C. and imaged each hour according to the procedure of Example 2. The onset of fluorescence was observed at approximately 5 hours in the microstructured surfaces. No fluorescence was seen in control samples.

Example 4

Detection of Bacteria in Cast Polypropylene Microstructures

Bacteria suspensions containing $10^1$-$10^2$ cfu of bacteria (*E. coli, E. aerogenes, C. freundii, K. pneumoniae*) were prepared in 10 mL of Colilert™ media dispensed into 50 mL centrifuge tubes. Control samples were prepared similarly, but received 100 µL of Butterfield's buffer. The Colilert™ media was supplemented with 40 µg/mL of MHC-gal or Mu-gal or Flu-gal for each bacteria suspension containing *E. aerogenes, C. freundii*, or *K. pneumonia*, to provide three different samples for each strain of bacteria.

A bacterial suspension containing *E. faecalis* was prepared in the same manner in 10 mL of Enterolert for *Enterococcus* spp., (IDEXX Laboratories, Inc.; Westbrook Me.) and dispensed into a 50 mL centrifuge tube. Control samples were prepared similarly, but received 100 µL of Butterfield's buffer.

Two sets of tubes were prepared with each bacteria strain. One set of tubes was capped with Cap1 with MS2C, and the other with Cap1 with MS2D. The tubes were centrifuged and inverted according to the procedure of Example 2. The caps were then opened and excess media from the edges of the caps was removed using a tissue (Kimwipes). Each tube was re-closed with the same cap and incubated at 37° C. The caps were periodically opened and the microstructured surfaces were imaged on the Fluorescent Imager.

The onset of fluorescence was observed with both *E. coli* and *E. faecalis* at approximately 3 hours in the microstructured surfaces. The onset of fluorescence was observed with the other coliforms in about 4 to 5 hrs. No fluorescence was seen in control samples.

Example 5

Detection of Bacteria in Cast Polypropylene Microstructures Using Large Sample Volume Circular disks 40 mm in diameter were cut with a hole punch from microstructured polypropylene sheets, of MS2C and MS2D. The disks were adhered to the flat inner surface of the sealing caps of 250 mL polypropylene centrifuge bottles (3141 Centrifuge Bottles with Sealing Cap; Nalgene Labware; Rochester N.Y.) using silicone polyurea transfer adhesive to provide a Cap1 construction. The protrusions were removed from tops of the caps to flatten the tops and to allow the bottles to be centrifuged with the cap down in the bottle holder. The caps had sealing gaskets to help prevent leakage during centrifugation.

*E. coli* suspensions each containing $10^1$-$10^2$ cfu were prepared in 100 mL of Colilert™ media and dispensed into 250 mL centrifuge tube bottles. Control samples were prepared similarly, but received 100 µL of Butterfield's buffer. The bottles were tightly closed with the microstructured caps and placed cap-down in a swinging bucket centrifuge rotor and centrifuged in the Benchtop Centrifuge for 30 min at 5000 RPM (5300 g). After centrifuging, the bottles were removed and inverted slowly to allow the media to drain into the bottle. Caps were removed and excess media was carefully removed from the edges using a tissue. The bottles were re-closed with the same caps and incubated at 37° C. The caps were removed periodically and the microstructured surface was imaged using the Fluorescent Imager.

Samples were prepared in the same manner except that the bottles were centrifuged for 1 hour before incubating. Onset of fluorescence was seen in 5 to 6 hrs. Centrifuging for 1 hour showed a greater number of positive wells than centrifuging for 30 minutes. No fluorescence was seen in control samples.

Example 6

External Detection of Bacteria in Transparent Polypropylene Replicated Structures An *E. coli* suspension containing $10^1$-$10^2$ cfu was prepared in 10 mL of Colilert™ media and dispensed into a 50 mL centrifuge tube. Control samples were prepared similarly, but received 100 µL of Butterfield's buffer. The centrifuge tube was closed with Lid 1 formed from COC1, with a cast polypropylene film having microstructured surface MS2C adhered to it, and further secured with a standard centrifuge cap to avoid leakage. The tube was centrifuged with the cap-down in the Multipurpose Centrifuge, and inverted according to the procedure of Example 2. The standard centrifuge tube cap was replaced with a cap having a hole in the center, and incubated at 37° C. The microstructures were imaged periodically on the Fluorescent Imager according to the procedure of Example 2 by removing the cap and imaging the microstructured surface, and also directly through the lid before removing the cap. The images obtained through the lid were comparable to those obtained by direct imaging of the microstructured wells. No fluorescence was seen in control samples.

The ability to image through the cap or a surface of the tube avoids the handling issues that can occur with opening the tube and applying a cover tape over the microstructures to prevent evaporation of the liquid from the wells. The microstructures in the cap retained sufficient liquid, because of surface tension and capillary action forces, to allow for growth of the bacteria. The media in remaining in the bottom of the tube provided sufficient humidity to prevent evaporation of liquid from the wells. No condensation was observed in the closed tubes at room temperature over a period of one week.

Example 7

External Detection of Bacteria in Injection Molded Structures

Lids in this example were prepared using the Lid 2 construction. The lids were molded from COC1 with microstructured surfaces MS3A and MS3B. Tubes were further secured using the standard threaded centrifuge tube caps for centrifugation and replaced with the cap with a hole in the center for incubating and imaging.

An $E.$ $coli$ suspension containing $10^1$-$10^2$ cfu was prepared in 10 mL of Colilert™ media and dispensed into a 50 mL centrifuge tube. Control samples were prepared similarly, but received 100 µL of Butterfield's buffer. The centrifuge tube was capped with Lid 2 molded with COC1 and having microstructured surface MS3A, and further secured with a standard centrifuge tube cap. A second tube was prepared using a lid molded with COC1 and MS3B. The centrifuge tubes were centrifuged cap-down, and slowly inverted according to the procedure of Example 2. The standard caps were replaced with the caps having a hole in the center and incubated at 37° C. The structures were imaged according to the procedure of Example 2 except that the measurement was done directly through the lid without removing the cap. The supernatant resulting from centrifugation remained in the tube and served as a humidity reservoir.

The same initial $E.$ $coli$ suspension was tested in Colilert™ media in a 96-well microtiter plate as described in the Reference Example.

As shown in Table 9, the onset of Mu-glcU fluorescence was observed in both lids (MS3A and MS3B) in about 4 hours and in 18 hours in the microtiter plates (see Table 9). No fluorescence was seen in the control samples.

TABLE 9

Comparison of time to detect 1 cfu of $E.$ $coli$

| | Mu-glcU fluorescence* | | |
|---|---|---|---|
| Time | MS3A (7 nL) | MS3B (7 nL) | 96-well microtiter plate (100 microliters) |
| 1 hr | No | No | No |
| 2 hr | No | No | No |
| 3 hr | No | No | No |
| 4 hr | Yes | Yes | No |
| 5 hr | Yes | Yes | No |
| 7 hr | Yes | Yes | No |
| 8 hr | Yes | Yes | No |
| 18 h | Yes | Yes | Yes |

*"Yes" refers to fluorescence observed; "No" refers to no fluorescence observed.

Example 8

Polymers for Molded Microstructures

Lids of the Lid 2 construction having microstructured surface MS3A were molded from the following polymers: COC1, COC2, COP, PMMA, PC, and PP. All of the molded lids were substantially transparent except for the PP ones which were too cloudy to permit imaging. The other lids made with COC1, COC2, COP, PMMA, and PC worked well for detection of bacteria in the molded structures. COC1, COC2, and COP had the lowest fluorescence background in UV-region and were optically clearer with higher transmission in UV-region, making them more desirable in many cases.

Example 9

External Detection of Bacteria in Molded Structures after Initial Growth

An $E.$ $coli$ suspension containing $10^1$-$10^2$ cfu was prepared in 10 mL of Colilert™ media and dispensed into a 50 mL centrifuge tube. The tube was sealed with Lid 2 molded from COC2 with MS3A and further secured with a standard centrifuge tube cap. A second sample was prepared in the same manner except that the microstructured surface of Lid 2, molded from COC2, with MS3B. Control samples were prepared similarly, but received 100 µL of Butterfield's buffer. The tubes were shaken at 300 RPM at 37° C. in an incubator shaker (Innova Model 4000 Incubator Shaker; New Brunswick Scientific; Edison N.J.) for 2 hrs. The tubes were then centrifuged cap-down, then slowly inverted, and the media drained back to the tube according to the procedure in Example 2. The standard caps were replaced with caps having a hole in the center, and incubated at 37° C. The structures were imaged through the lid using the Fluorescent Imager.

Growth of $E.$ $coli$ was detected in about 5 hrs through both microstructured surfaces as measured by Mu-glcU fluorescence. The initial growth for 2 hours followed by centrifuging of cells into microstructures resulted in an increased number of positive wells compared to centrifuging without prior incubation. No fluorescence was seen in control samples.

Example 10

Prophetic External Detection of Bacteria in Bottles/Tubes Molded with Microstructured Surfaces In this illustration, the bottle/tube is molded so that the microstructured surface(s) are at the bottom of the sample bottle/tube (see, for example, FIGS. 6A-6C of co-pending U.S. Patent Application No. 61/503,328, filed on Jun. 30, 2011. Typically between 10 mL to 100 mL, is collected and a growth medium is added to the sample in the bottle/tube. Alternatively, growth medium may be coated in the microstructured surface(s) or on a sidewall of the bottle/tube. The sample is mixed thoroughly to dissolve the growth media and the bottle/tube is centrifuged in an appropriate centrifuge, e.g., the Multipurpose Centrifuge for a 10 to 100 mL sample. Time of centrifuging is typically 10 to 30 minutes, but may be more depending on the sample size. After centrifuging, the sample bottles/tubes are removed and inverted slowly to drain the media away from the microstructured surface and incubated at suitable temperatures, e.g., 37° C. The microstructured surface is imaged/read at periodic intervals using a suitable reader and detection of wells showing a positive signal indicates presence of bacteria in the sample. The medium may include one or more dye substrates to indicate the presence of bacteria, e.g., galactosidase and glucuronidase substrates can be used individually or in combination for detection of coliforms and E. coli.

Example 11

Detection of Bacteria in Microstructured Surfaces Adhered to Bottom of a Bottle Circular disks measuring 40 mm in diameter were cut from polypropylene sheets having MS2B, MS2C, and MS2D using a hole punch. Each of the disks was adhered to the bottom of an empty dilution bottle (3M Flip-Top dilution bottle; 3M Company) using the silicone polyurea transfer adhesive described for Capt. An E. coli suspension containing $10^1$-$10^2$ cfu was prepared in 100 mL of Colilert™ media and dispensed into each bottle with the microstructured surface. Control samples were prepared similarly, but received 100 μL of Butterfield's buffer. The bottles were centrifuged according to the procedure of Example 2 except that the bottle was placed with the cap up as the microstructured surface was at the bottom of the bottle, and the bottle was centrifuged for 20 min at 5000 RPM (4500 g). After centrifuging, the bottles were removed, inverted slowly to drain the media away from the microstructures, and incubated at 37° C. in the inverted position. The bottles were incubated for 8 to 10 hours, the media was drained, and the bottle was cut in the middle so that the bottle fit into the Fluorescent Imager for imaging. The bottles were imaged in the upright position as the polypropylene used was not transparent to UV. After 8 to 10 hours of incubation fluorescence from E. coli was seen in all of the structures. No fluorescence was seen in control samples. This experiment shows that bacteria from a large sample can be concentrated by centrifugation and detected in microstructures adhered to the bottom of a bottle.

Example 12

Contact Angle Measurements of PMMA, COC1, COC2, PC, COP

The static and dynamic contact angles of molded polymers were determined using the sessile drop method on a VCA 2500 XE Video Contact Angle System. The data was analyzed using VCA-2500XE image analysis software. The instrument and software were obtained from AST Products, Inc., Billerica Mass. Molded lids of the Lid 2 construction with microstructured surface MS3A were prepared using PMMA, COC1, COC2, PC, and COP polymers. The lids were tested on the flat side without the microstructure.

For the static contact angle, 1 μL droplets of water were delivered to the surfaces at room temperature. The right and left contact angles were measured immediately after the drop formed on the surface with the syringe tip retracted.

For the dynamic contact angle, 1 μl droplets were delivered to the surfaces and water was added or withdrawn from the droplet with the syringe set at medium speed. Frames of video images were obtained showing when the drop expanded or contracted most symmetrically to determine the Advancing and Receding dynamic contact angles. The hysteresis was calculated as the difference between the advancing and receding contact angles. Results are shown in Table 10.

TABLE 10

Static and Dynamic Contact Angle Measurements

| Polymer | Static contact Angle/ Std Dev | | Dynamic Contact Angle/ Std Dev. | | Hysteresis |
|---|---|---|---|---|---|
| | Left Angle | Right Angle | Advancing | Receding | |
| PMMA | 86.9/5.4 | 86.7/5.6 | 84.8/1.0 | 44.6/1.4 | 40.2 |
| PC | 89.9/1.4 | 89.8/1.7 | 93.6/2.0 | 37.8/1.6 | 55.8 |
| COC1 | 96.4/2.1 | 96.1/1.7 | 91.2/2.2 | 41.1/3.5 | 50.1 |
| COC2 | 95.7/1.5 | 95.5/1.4 | 97.7/1.5 | 41.5/0.8 | 56.2 |
| COP | 85.4/5.0 | 85.2/4.9 | 95.1/1.1 | 25.4/1.2 | 69.7 |

Example 13

Contact Angle Measurement of Microstructure Surfaces of Injection Molded Lids with and without Surface Treatments Molded lids of construction Lid 2, with microstructured surface MS3A and MS3B prepared using COC2 were used in this example.

The molded side with microstructures was first plasma treated using an apparatus described in detail in U.S. Pat. No. 5,888,594, which is incorporated herein by reference in its entirety. The molded lids were mounted onto the cylindrical drum electrode with microstructures facing up and the chamber was pumped down to a base pressure of $5 \times 10^{(-4)}$ Torr. Argon gas was introduced into the chamber at a flow rate of 500 sccm (standard cubic centimeters per minute) and plasma ignited and maintained at a power of 500 watts for 30 seconds. After the argon plasma treatment, tetramethylsilane (TMS) vapor was introduced into the chamber at a flow rate of 360 sccm and the plasma sustained at a power of 500 watts for 30 seconds. After the plasma treatment in tetramethylsilane vapor, oxygen gas was introduced into the chamber at a flow rate of 500 sccm and plasma sustained at a power of 500 watts for 60 seconds. The pressure in the chamber during these plasma treatment steps was in the 5-10 mTorr range. The plasma chamber was then vented to atmosphere and the plasma treated molded lids were removed from the chamber and labeled as MS3A-4 and MS3B-4 (Table 11).

Another set of molded lids were treated similarly with Argon plasma followed by TMS vapor. After the plasma treatment in tetramethylsilane vapor, oxygen gas was introduced into the chamber to achieve desired TMS to oxygen ratio and plasma sustained at a power of 500 watts for 60 seconds. The pressure in the chamber during these plasma treatment steps was in the 5-10 mTorr range. The plasma chamber was then vented to atmosphere and the plasma treated molded lids were removed from the chamber and labeled as MS3A-3, MS3B-3, MS3A-2 and MS3B-2 (Table 11).

Another set of molded lids were treated similarly with Argon plasma followed by TMS vapor. The molded lids were not treated with oxygen gas. The plasma chamber was vented after TMS vapor treatment to atmosphere and the plasma treated molded lids were removed from the chamber and labeled as MS3A-1 and MS3B-1 (Table 11).

Untreated molded lids were labeled as MS3A-0 and MS3B-0 (Table 11).

The static contact angles of treated and untreated microstructure surfaces were determined using the sessile drop method on a VCA 2500 XE Video Contact Angle System as described in Example 12.

TABLE 11

Static contact angle measurements of treated and untreated microstructure surfaces of injection molded lids

| Treatment | MS 3A Lid | Static contact Angle/Std Dev Left Angle | Static contact Angle/Std Dev Right Angle | MS3B Lid | Static contact Angle/Std Dev Left Angle | Static contact Angle/Std Dev Right Angle |
|---|---|---|---|---|---|---|
| Untreated | MS3A-0 | 90.72/2.04 | 90.57/2.26 | MS3B-0 | 86.27/2.45 | 85.82/2.58 |
| 1:0 (TMS:$O_2$) | MS3A-1 | 98.91/3.49 | 98.53/3.65 | MS3B-1 | 86.309/1.81 | 86.309/2.03 |
| 1:3.3 (TMS:$O_2$) | MS3A-2 | 71.19/2.37 | 71.22/2.63 | MS3B-2 | 81.85/3.11 | 82.14/3.56 |
| 1:10 (TMS:$O_2$) | MS3A-3 | 73.15/3.04 | 72.48/2.94 | MS3B-3 | 82.57/3.66 | 83.33/3.86 |
| Silane Oxygen | MS3A-4 | 68.28/7.70 | 67.6/9.62 | MS3B-4 | 76.82/4.60 | 75.633/4.32 |

Example 14

Effect of Rate of Inversion Times on Residual Droplet Formation on Microstructures Lids of construction Lid 2 were molded with microstructured surfaces MS3A and MS3B from various polymers shown in Table 12.

A solution of fluorescein sodium salt (Sigma Aldrich), prepared by dissolving 1 mg of fluoroscein in 10 mL of distilled water was dispensed into a 50 mL centrifuge tube. The centrifuge tube was closed with the molded lid and capped with a standard centrifuge tube cap. The centrifuge tube was centrifuged according to the procedure in Example 2. The tube was then placed cap-down down in a Thermolyne Vari Mix rocker Model M8474 (Barnstead Thermolyne, Dubuque, Iowa) and turned at varying speeds shown in Table 12. The angle of rotation was 60 degrees (−30 degrees in the inverted position to +30 degrees in the upright position) and based on time taken to complete 60 degrees, the speed was calculated as degrees/sec. After completing the turn so that the tube was in an upright position, the microstructures were imaged and analyzed through the top using the Fluorescent Imager.

The images were examined for residual droplets remaining on the top surface of the microstructures. Results in Table 12 show the presence of residual droplets bridging multiple wells at inversion speeds greater than about 20 degrees/sec (0.3 rpm). At higher speeds of inversion the number of drops increased as well as the size of the drops so that a single drop bridged a greater number of wells. The contact angle of the materials tested ranged from varied from 85.2 to 96.4 degrees.

TABLE 12

Effect of inversion speed on bridging

| Degrees/sec | Revolutions per minute (rpm) | MS3A COC1 | MS3A COC2 | MS3A COP | MS3A PMMA | MS3A PC | MS3B COC2 |
|---|---|---|---|---|---|---|---|
| 4.3 | 0.72 | No | No | No | No | No | No |
| 10 | 0.2 | No | No | No | No | No | No |
| 20 | 0.3 | No | Few | No | No | No | Few |
| 30 | 0.5 | Some | Some | Some | Some | Some | Some |
| 60 | 1 | Some | Some | Some | Some | Some | Some |

No = No drops were observed around the structures - no bridging.
Few = occasionally small (millimeter diameter) drops were observed to bridge two or more wells
Some = Drops were observed more frequently; drops were larger (several millimeters) and bridged a larger number of wells within the drop Example 15

Evaporation Rates of Water in Injection Molded Microstructures

Lids in this example were prepared using the Lid 2 construction. The lids were molded from COC2 with microstructured surfaces MS3A and MS3B. Tubes were further secured using the standard threaded centrifuge tube caps for centrifugation and replaced with the cap with a hole in the center for incubating. Ten mL of distilled water was dispensed into a 50 mL centrifuge tube. The centrifuge tube was capped with the molded lid with MS3A or MS3B and further secured with a standard centrifuge tube cap. The centrifuge tubes were then centrifuged cap-down, and slowly inverted according to the procedure of Example 2.

In one experiment, one set of filled lids were opened and weighed at periodic intervals at room temperature using a Mettler Toledo AG204 Balance (Mettler-Toledo Inc., Columbus, Ohio). Another set of lids were opened and sealed immediately with a 24 millimeter diameter clear adhesive film (MicroAmp™ Optical Adhesive Film; Applied Biosystems) and weighed at periodic intervals at room temperature. The sealed lids were also incubated at 37° C. for and weighed at periodic intervals.

In another experiment, Ten mL of distilled water was dispensed into a 50 mL centrifuge tube. The centrifuge tube was capped with the molded lid with MS3B and further secured with a standard centrifuge tube cap. The centrifuge tubes were then centrifuged cap-down, and slowly inverted according to the procedure of Example 2. The lids were opened, weighed, and immediately sealed back to the same centrifuge tube and further secured with the standard centrifuge tube cap. The tubes with sealed lids were kept at 37° C. and the lids were weighed periodically. After each measurement, the lids were immediately sealed back to the centrifuge tube.

The results of the experiment are shown in Tables 13-15. All the water in lids with injection molded structures evaporated in 15 to 30 min at room temperature. The lids sealed with adhesive film showed no appreciable evaporation and upon incubation at 37° C. for 18 h, the sealed lids had 4 to 8% loss. The lids sealed into centrifuge tubes showed 17 to 20% loss after 18 h of incubation at 37° C. A portion of this loss was attributed to opening the lids for weighing.

TABLE 13

Evaporation of water from open and sealed lids at room temperature

| | MS3A | | | | MS3B | | | |
| --- | --- | --- | --- | --- | --- | --- | --- | --- |
| | Open | | Sealed | | Open | | Sealed | |
| Time | Trial 1 | Trial 2 | Trial 1 | Trial 2 | Trial 1 | Trial 2 | Trial 1 | Trial 2 |
| 5 min | 89% | 77% | 0% | 0% | 41% | 37% | 0% | 0% |
| 10 min | 94% | 88% | 0% | 0% | 58% | 63% | 0% | 0% |
| 15 min | 100% | 100% | 0% | 0% | 79% | 88% | 0% | 0% |
| 20 min | nd | nd | 0% | 0% | 93% | 100% | 0% | 0% |
| 25 min | nd | nd | 0% | 0% | 98% | 100% | 0% | 0% |
| 30 min | nd | nd | 0% | 0% | 100% | 100% | 0% | 0% | nd: not determined

TABLE 14

Evaporation of water from lids sealed with adhesive film at 37° C.

| Time | MS3A | MS3B |
| --- | --- | --- |
| 30 min | 0% | 0% |
| 1 hr | 1% | 1% |
| 3 hr | 1% | 1% |
| 18 hr | 8% | 4% |

TABLE 15

Evaporation of water from MS3B lids sealed to centrifuge tubes at 37° C.

| | % loss of water | |
| --- | --- | --- |
| Time | Trial 1 | Trial 2 |
| 30 min | 1% | 1% |
| 1 hr | 3% | 5% |
| 3 hr | 5% | 6% |
| 4 hr | 8% | 8% |
| 18 hr | 17% | 20% |

Example 16

Preparation of First Container Comprising a Closed Receptacle Portion

With reference to FIGS. 7-8, a filter housing 232 for a filter portion 208 of a closed receptacle portion 206 was constructed from CAD drawings using a UV curable epoxy composition (Accura® 60 epoxy resin) in a sterolithography machine (SLA—Model SLA-250/40 machine) according to the manufacturer's instructions. The epoxy composition and the machine were manufactured by 3D Systems Corporation; Rock Hill S.C.).

The filter housing 232 was formed as two separate parts, a tube 234 with threads 229 and a base 235 that was configured to form a friction fit with the tube 234 and to receive a filter 212 when assembled. The filter housing 232 was approximately 5 cm in height. A filter connection assembly 220 was constructed using CAD drawings with the same SLA machine. The assembly 220 included a gasket 224A and a connector 222 with a vent port 228 and a corresponding filter plug 230. The filter plug 230 was formed of POREX® hydrophobic polyethylene sheet POR-4902 (Porex Technologies, Fairburn, Ga.) and was cut to fit the vent port 228. Gaskets 224A and 224B were formed by using CAD drawings in a 3D printing system (EDEN 500V™ 3-Dimensional Printing System) using Objet Tango Gray FullCure 950 (semi-soft Gray), 75 Shore A or Objet Tango black 970 (soft black), 61 shore A resin (Objet Geometries Inc.; Billerica Mass.). Alternative gaskets may be formed for other types of materials such as silicones, rubbers vinyl, etc. using other methods, e. g. injection molding, die cutting from a sheet, etc.

The gasket 224A and 224B made by 3D printing were very fragile and after initial experiments, the gaskets were made by die cutting a sheet formed of silicone and a rubber. Example 20 used gaskets formed of Objet Tango Gray for *E. coli* samples and Objet Tango Black for *E. faecalis*. Examples 18, 19, 21, 22 and 23 used gaskets formed of silicone and a rubber.

The receptacle portion 206 for this example was a 1 liter polypropylene sample bottle (Nalgene 2087 Narrow-Mouth Economy Bottle—Cat. No. 2087-0032; Nalgene Nunc, Thermo Fisher Scientific; Rochester N.Y.). The combination of the receptacle portion 206 and the filter portion 208 formed a "first container" according to the present disclosure.

In use, a sample was prepared in the receptacle portion 206. A filter (Filter A, Filter B, or Filter C) was inserted into the filter housing 232, and the filter portion 208 connected to the receptacle portion 206 via the filter connection assembly 220. The other end of the filter portion 208 was then connected to a vacuum assembly and filtered to capture at least a portion of the bacteria. The vacuum assembly was connected to a vacuum flask or a vacuum manifold. The filter housing 232 was then disconnected from the bottle (i.e., receptacle portion 206) and a polyethylene cap (U.S. Plastic Corp, Lima, Ohio) was used to close the base 235. The threaded end of the filter portion 208 was removed from the filter connection assembly 220 and the receptacle portion 206 and closed with a second lid or cap (i.e., a detection portion 110; see FIGS. 3, 4 and 5) having a microstructured surface, e.g., Cap 1, Lid 1, or Lid 2, molded to fit tightly on the filter portion 208 to form a "second container" of the present disclosure. A gasket may be used to help prevent leakage during processing.

The same filter housing 232 (containing tube 234 and base 235) and filter connection assembly 220 were also constructed from CAD drawings on a 3D printing system (EDEN 500V™ 3-Dimensional Printing System) using an UV-curable acrylic composition (Objet VeroWhite—FullCure 830) according to the manufacturer's instructions. The acrylic composition and system were manufactured by Objet Geometries Inc.; Billerica, Mass.

In Example 20, the filter housing was formed of Object VeroWhite—FullCure 830. In Examples 18, 19, 21, 22 and 23, the filter housing was formed of the Accura® 60 epoxy resin.

Example 17

Preparation of a First Container Comprising an Open Receptacle Portion

With reference to FIGS. 1-5, a filter portion 108 comprising a filter housing 132, and a filter connection assembly 120 for use with an open receptacle portion 106 were constructed from a CAD drawing using a UV curable epoxy composition (Accura® 60 epoxy resin) in a stereolithography (SLA) machine (Model SLA-250/40 machine) according to the manufacturer's instructions and the procedure of Example 16. The filter housing 132 included a tube 134 with threads 129 on one end 145 and a base 135 on the other end 144. The tube 134 and base 135 were configured to form a friction fit with each other and to receive a filter 112 when assembled. The threaded end was connected to a receptacle portion 106 which can be molded using suitable materials, but in these examples, the below Corning™ bottle was used.

The receptacle portion 106 for this example was a 500 mL bottle top filter with a 33 mm diameter neck (Corning™ 500 mL Bottle Top Vacuum Filter Cat #430512; Corning Inc.; Lowell Mass.) in which the existing filter was removed. This receptacle portion 106 included the filter connection assembly 120 integrally formed therein and included a vent port 128 fit with the same filter plug as Example 16; however, the vent port 128 was not necessary in this case because the receptacle portion 106 was open to atmosphere. The combination of the receptacle portion 106 and the filter portion 108 formed a "first container" according to the present disclosure.

The first container and the second container were used according to the procedure of Example 16 except that the prepared sample was poured into the open end 114 the receptacle portion 106 and filtered.

Example 18

Recovery of Bacteria from a First Container Comprising a Closed Receptacle

A bacterial suspension of *E. coli* was prepared and serially diluted so that the dilution contained about 100 cfu/mL. Three 1000 mL sample bottles (Nalgene) were filled with 1000 mL of sterile water and 1 mL of the suspension was added to each bottle. A filter portion 208, constructed according to the procedure of Example 16, was assembled with Filter A, Filter B, or Filter C and connected to the filled sample bottle via the filter connection assembly 220. The base 235 of the filter portion 208 was placed over a vacuum flask attached to a vacuum assembly and the sample was filtered through the filter at a vacuum pressure of about 20 inches of mercury. After filtering, the filter portion 208 was removed from the vacuum apparatus, the filter connection assembly 220 was removed from the filter housing 232, the base 235 was pulled out, and each of the filter membranes was removed aseptically and placed on a hydrated 3M PETRIFILM *E. coli*/Coliform Count Plates (3M Co.), prepared according to the manufacturer's instructions, and incubated overnight at 37° C. The plates were read using a 3M™ PETRIFILM™ Plate Reader (3M Co.) and/or counted manually to determine colony forming units (cfu). Results shown in Table 16 indicate that over 90% of the bacteria were recovered.

TABLE 16

Recovery of *E. coli* by filtration

| Filter | Total cfu recovered Input - 125 cfu | % Recovery |
|---|---|---|
| Filter A | 114 | 91.2 |
| Filter B | 113 | 90.5 |
| Filter C | 115 | 92.0 |

Example 19

Recovery of Bacteria from Filtered Water Samples Followed by Elution

Three 1000 mL water samples containing *E. coli* were prepared and filtered according to the procedure of Example 18 using each of the Filters A-C. After filtering, the filter portion 208 was removed from the vacuum apparatus, base 235 of the filter portion 208 was capped and the filter connection assembly 220 was removed from the tube 234. Three mL of prepared Colilert™ media was added to the filter portion 208 and then closed with a 33 mm diameter threaded cap. The resulting container was vortexed (Fixed Speed Vortex Mixer, VWR Intl. LLC; Batvia Ill.) for 2 minutes at room temperature to elute the bacteria from the filter. The vortexed sample was plated on 3M™ PETRIFILM™ *E. coli*/Coliform Count Plates (3M Co.) according to manufacturer's instructions, and incubated overnight at 37° C. The plates were read using a 3M™ PETRIFILM™ Plate Reader (3M Co.) and colony forming units (cfu) were determined and are shown in Table 17 for each filter. The filtration times for 1000 mL samples under 20 mm Hg vacuum are also shown in min:sec. Filter A showed the highest recovery of *E. coli* (about 74%; Table 17).

TABLE 17

Recovery of *E. coli* by filtration and elution

| | Total cfu recovered | % Recovery | Filtration Time (min:sec) |
|---|---|---|---|
| | Input - 95 cfu | | |
| Filter A | 70 | 73.7 | 6:01 |
| Filter B | 38 | 40.0 | 2:41 |
| Filter C | 25 | 26.3 | 2:35 |

Example 20

Detection of Bacteria from Filtered Water Sample after Growth in Microstructures Three 1000 mL water samples each containing 10 cfu of *E. coli* were prepared and filtered according to the procedure of Example 18 using Filter A. After filtering, the filter portion 208 was removed from the vacuum apparatus, the base 235 of the housing 232 was capped and the filter connection assembly 220 was removed from the tube 234.

Three mL of prepared Colilert™ media was added to the sample (i.e., the filtrand) in the filter portion 208. The filter portion 208 was closed with a Lid 2 molded from COC2 and having microstructured surface MS3A. A second sample was prepared with Lid 2 with structure MS3B. The filter portions 208 were further secured with a threaded 33 mm diameter cap with an optical (i.e., viewing) window. The combination of the cap and Lid 2 with either microstructured surface functioned as the detection portion 110 in this example. The combination of the filter portion and the detection portion formed a "second container" according to the present disclosure.

Three 1000 mL water samples, each containing 10 cfu of *E. faecalis* were also prepared and filtered according to the same procedure and 3 mL of Enterolert media (IDEXX) were added to each second container after filtration. Lid 2 with each microstructure was used to cap the samples.

Control samples were prepared similarly, but received 1 mL of Butterfield's buffer.

The second containers were vortexed (Fixed Speed Vortex Mixer, VWR) for 2 minutes at room temperature and then centrifuged cap-down (i.e., detection portion down) in a multipurpose centrifuge for 20 min at 4000 RPM (2800 g). After centrifuging, the second containers were removed and inverted slowly to drain the media back into the container, away from the microstructured surface. The second containers were then incubated at 37° C. in the inverted position. The structures were imaged through the lids using the Fluorescent Imager. Onset of fluorescence was observed at approximately 4 to 5 hours in the microstructured surfaces. No fluorescence was seen in control samples.

Example 21

Detection of Bacteria from Water Samples Using a First Container Comprising an Open Receptacle A first container, constructed according to the procedure of Example 17 with Filter A was placed on a vacuum flask connected to the vacuum apparatus. One liter of sterile water was containing 10 cfu *E. coli* was prepared and poured into receptacle portion 106 and filtered under vacuum pressure of 20 inches mercury. The first container was removed from the vacuum flask and the base 135 was capped. The receptacle portion 106 was removed from the filter portion 108. A second sample was prepared and filtered according to the same procedure except it contained 10 cfu of *E. faecalis*. Control samples were prepared similarly, but received 1 mL of Butterfield's buffer and no bacteria.

Three mL of Colilert (for *E. coli*) or Enterolert (for *E. faecalis*) were added to the appropriate filter portions 108 and the filter portions 108 were closed with lids and caps (i.e., detection portions) according to the procedure in Example 20 to form "second containers." The second containers were vortexed (Fixed Speed Vortex Mixer) for 2 minutes at room temperature and then centrifuged with the cap-down (i.e., with the detection portion down) in a multipurpose centrifuge. After centrifuging, the second containers were removed and inverted slowly to drain back the media into the container, away from the microstructured surface. The samples were incubated at 37° C. in the inverted position. The structures were imaged using the Fluorescent Imager. Onset of fluorescence was observed at approximately 4 to 5 hours in the microstructured surfaces for *E. coli*, and in 5 hours for *E. faecalis*. No fluorescence was seen in control samples.

Example 22

Detection of Bacteria from Filtered Water Samples Followed by Growth in Cast Polypropylene Microstructures The first container of Example 16 was assembled with Filter B.

A 1 liter water sample containing 10 cfu of *E. coli* and a second 1 liter water sample containing 10 cfu *E. faecalis* were prepared in Nalgene bottles according to the procedure in Example 18. Filter A was inserted into the filter portion 208 of Example 16 and connected via the filter connection assembly 220 to the bottle (i.e., receptacle portion 206). The samples were filtered and after filtering, the filter portion 208 was removed from the vacuum apparatus, the connection assembly 220 was removed from the filter housing 232, base 235 was pulled out, and the membrane was aseptically transferred to a 50-mL centrifuge tube. One-liter control samples were prepared similarly, but received 1 mL of Butterfield's buffer and no bacteria.

Approximately 5 to 10 mL of Colilert media for *E. coli* or Enterolert for *E. faecalis* were added to the appropriate filter portion, and the filter portions for each were closed with Lid 1 with microstructure surface MS2C. A second set of identical tubes were closed with Lid 1 with structure MS2D. The combination of the cap and Lid 1 with either microstructured surface functioned as the detection portion 110 in this example. The combination of the filter portion and the detection portion formed a "second container" according to the present disclosure.

The second containers were vortexed, centrifuged, inverted slowly, and incubated according to the procedure of Example 18. The microstructures were imaged using the Fluorescent Imager through the lids.

Onset of fluorescence was again observed at approximately 4 to 5 hours in the microstructured surfaces. No fluorescence was seen in control samples.

Example 23

Fold Increase of Recovered Bacteria after Incubation

A filter portion 208 was assembled with Filter A, B or C. A 1000-mL water sample containing 10 cfu of *E. coli* was prepared in a Nalgene bottle. The filter portion 208 was connected to the bottle (i.e., the receptacle portion 206) and a vacuum apparatus according to the procedure in Example 18 and filtered. After filtering, the base 235 was capped and the filter portion 208 was detached from the receptacle portion 206. Five mL of Colilert™ media were added to the filter portion 208, and the filter portion 208 was closed with a threaded 33 mm diameter cap. A second filter portion 208 was prepared in the same manner except 5 mL of Readycult® media was used.

The samples were vortexed (Fixed Speed Vortex Mixer) for 2 minutes at room temperature, and then placed in an incubator shaker (Newbrunswik Scientific shaker, Model Innova 4000) and agitated at 300 rpm for 2 hours at 37° C. Controls were prepared by adding 10 cfu to 5 mL of Colilert media or 5 mL of Readycult® media to 50 mL centrifuge tubes, and shaken and incubated in the same manner. At the end of growth period, samples from each of the tubes were plated on 3M PETRIFILM *E. coli*/Coliform Count Plates according to the manufacturer's instructions, and incubated overnight at 37° C. The plates were read using a 3M™ PETRIFILM™ Plate Reader to determine colony forming units (cfu). The input number of cells was used to calculate the fold-increase. Results are shown in Table 18.

TABLE 18

Increase in cell number of *E. coli* after filtration and growth

| | Colilert™ Medium | | Readycult® Medium | |
| --- | --- | --- | --- | --- |
| Filter | cfu in 5 mL | Fold-increase | cfu in 5 mL | Fold-increase |
| | Input to 1 liter water - 11 cfu | | | |
| Control (no filtration) | 72 | 6.5 | 70 | 6.4 |
| Filter A | 65 | 5.9 | 65 | 5.9 |
| Filter B | 60 | 5.5 | 60 | 5.5 |
| Filter C | 45 | 4.1 | 82 | 7.5 |

Example 24

External Detection of Bacteria in Transparent Polypropylene Replicated Structures Using a Chromogen and a Fluorogen An *E. coli* suspension containing $10^1$-$10^2$ cfu was prepared in 10 mL of Readycult® media and dispensed into a 50 mL centrifuge tube. Control samples were prepared similarly, but received 100 µL of Butterfield's buffer. The centrifuge tube was closed with Lid 1 formed from COC1, with a cast polypropylene film having microstructured surface MS2C adhered to it, and further secured with a standard centrifuge cap to avoid leakage. The tube was centrifuged with the cap-down in the Multipurpose Centrifuge, and inverted according to the procedure of Example 2. The standard centrifuge tube cap was replaced with a cap having a hole in the center, and incubated at 37° C. The microstructures were imaged periodically directly through the lid in the imaging system using illuminated and fluorescent light.

The same initial *E. coli* suspension was tested in Readycult® media in a 96-well microtiter plate as described in the Reference Example.

Readycult® media contains a fluorogen (Mu-glcu) and a chromogen (X-gal). A color change to blue-green indicates cleavage of X-gal by galactodidase and a blue fluorescence under UV-light indicates cleavage of Mu-glcU by glucuronidase activity. Onset of fluorescence was seen in about 5 hrs and precipitated X-gal was visible in the microstructures in about 10 to 12 hrs. The microtiter wells inoculated with 1 cfu showed onset of fluorescence and color change in about 18 hrs. No fluorescence was seen in control samples.

Example 25

Measurement of Volume Retained in Microstructured Recesses

An injection molded container (i.e., bottle or tube) having an approximate included volume of 120 milliliters was prepared as described in Example 10. The container was molded from TOPAS 8007S-04 polymer, and included the microstructured surface MS3B in the base (see, e.g., FIGS. 6A-6C). A fluorescent solution was prepared by dissolving 0.5 milligrams of CY5 labeled streptavidin (Fluorolink PA45001, Amersham Biosciences, Buckinghamshire England) in 100 milliliters of distilled water. 10 milliliters of this solution was placed in the container. The container was capped and centrifuged toward the microstructured surface for 10 minutes at 4000 RPM. After centrifugation, the container was removed and inverted 180 degrees by manually rotating at approximately 0.2 RPM as described in Example 14. After inversion, the supernatant was left in the capped tube to provide a humidity reservoir to minimize evaporative loss of liquid in the microwells during analysis. The container was placed on the stage of a confocal microscope (Zeiss Axioplan 2 with LSM 510 Laser Module, Zeiss, Thornwood N.J.) equipped with an Achroplan 40X/0.8W objective. A three dimensional image of solution in a microstructured recess was obtained using 633 laser excitation at 50% power and a 650 nm long pass filter. The scanning parameters were set to define a field of view of 320 microns by 320 microns by 200 microns. Z axis slices were obtained every 1.31 microns using a pinhole of 68 microns. The resulting three-dimensional image was used to establish the Z axis position of the top of the sidewall of the recess (scattered/reflected light), the base of the recess, and the height of the fluorescent solution. Using the orthogonal viewing mode (X,Z and Y,Z slices), the top of the sidewall of the recess was determined to be at slice 131, the fluorescent liquid level at slice 94, and the base at slice 8. After subtracting the level of the base, the liquid level was determined to be 30% below the top plane of the microstructures (i.e., of the sidewall), coinciding with an inflection point in the sidewall where the radius of curvature of the sidewall changed and the sidewall transitioned from a radiused portion to a flat portion.

Various features and aspects of the present disclosure are set forth in the following claims.

What is claimed is:

1. A method for detecting an analyte of interest in a sample, the method comprising:
    providing a first container comprising a filter portion, the filter portion comprising a filter configured to retain the analyte of interest from the sample, the filter having a first side and comprising a filtrand of the sample on the first side;
    coupling the filter portion to a detection portion to form a second container, the detection portion comprising a microstructured surface configured to provide capillary forces to retain a sample of interest, the filter portion and the detection portion being coupled together such that the first side of the filter faces the microstructured surface of the detection portion;
    centrifuging the second container toward the microstructured surface to move the filtrand from the filter to the microstructured surface of the detection portion to form a sediment and a supernatant of the sample; and
    inverting the second container, after centrifuging the second container, to decant at least a portion of the supernatant from the detection portion, such that a concentrate of the sample is retained in the microstructured surface of the detection portion of the second container, the concentrate comprising the sediment.

2. The method of claim 1, further comprising interrogating the concentrate in the microstructured surface for the analyte of interest.

3. The method of claim 2, wherein the microstructured surface is formed in a first side of the detection portion, and wherein interrogating the concentrate in the microstructured surface includes interrogating the concentrate in the microstructured surface from the first side of the detection portion.

4. The method of claim 2, wherein the microstructured surface is formed in a first side of the detection portion and the first side is positioned to face the filter portion during centrifugation, wherein the detection portion further comprises a second side opposite the first side, and wherein interrogating the concentrate in the microstructured surface includes interrogating the concentrate in the microstructured surface from the second side of the detection portion.

5. The method of claim 2, wherein the filter portion and the detection portion of the second container remain coupled together during the centrifuging step, the inverting step, and the interrogating step.

6. The method of claim 2, wherein interrogating the concentrate in the microstructured surface occurs while the detection portion of the second container remains coupled to the filter portion of the second container, such that the supernatant serves as a humidity reservoir.

7. The method of claim 1,
wherein the first container further comprises a receptacle portion adapted to contain the sample, the filter portion adapted to be removably coupled to the receptacle portion;
filtering the sample by moving the sample in a first direction from the receptacle portion toward the first side of the filter to form a filtrand of the sample on the first side of the filter, while removing a filtrate of the sample;
decoupling the receptacle portion and the filter portion of the first container;
and
interrogating the concentrate in the microstructured surface for the analyte of interest.

8. The method of claim 1, wherein inverting the second container includes inverting the container at a rotational speed of no greater than 0.3 rpm.

9. A system for detecting an analyte of interest in a sample, the system comprising:
a first container comprising a filter portion, the filter portion comprising a filter, the filter having a first side and comprising a filtrand of the sample on the first side;
a second container comprising the filter portion coupled to a detection portion, the detection portion comprising a microstructured surface, the filter portion and the detection portion being coupled together such that the first side of the filter portion faces the microstructured surface of the detection portion, the microstructured surface of the detection portion adapted to receive a concentrate of the sample when the second container is exposed to a centrifugal force, the microstructured surface of the detection portion further adapted to retain at least a portion of the concentrate of the sample under normal gravitational forces, the microstructured surface comprising a plurality of microstructured recesses, each recess having a base and a sidewall, wherein the upper surface of each sidewall is radiused.

10. The system of claim 9, wherein the first container further comprises a receptacle portion adapted to contain the sample, the filter portion adapted to be removably coupled to the receptacle portion.

11. The system of claim 10, wherein the filter portion includes a first end comprising the filter and a second end adapted to be coupled to the receptacle portion or the detection portion.

12. The system of claim 10, further comprising a filter connection assembly configured to couple the receptacle portion and the filter portion together.

13. The system of claim 9, wherein the filter portion includes a first end comprising the filter and a second end adapted to be coupled to the detection portion, and wherein the detection portion has a first end comprising the microstructured surface and a second end adapted to be coupled to the filter portion.

14. The system of claim 9, wherein the microstructured surface is formed in a first side of the detection portion and the first side is positioned to face the filter portion during centrifugation, wherein the detection portion further comprises a second side opposite the first side, and wherein the microstructured surface comprises a plurality of microstructured recesses, each recess having a base, and wherein each base is substantially transparent, such that the contents of the plurality of microstructured recesses are visible from the second side of the detection portion of the container.

15. The system of claim 14, wherein at least one of the plurality of microstructured recesses includes a sidewall, and wherein the sidewall is substantially non-transparent.

16. The system of claim 9, wherein the microstructured surface comprises a plurality of recesses, and wherein each of the plurality of recesses contains a volume of no greater than 1 microliter.

17. The system of claim 9, wherein the microstructured surface comprises a plurality of recesses, wherein the plurality of recesses define a collective volume, and wherein the collective volume is no greater than 100 microliters.

18. The system of claim 9, wherein the filter includes at least one of a polyolefin porous membrane, an ethylene-chlorotrifluoroethylene copolymer porous membrane, a polyacrylonitrile porous membrane, a polycarbonate porous membrane, a polyester porous membrane, a cellulose ester porous membrane, a polyamide porous membrane, a polyethersulfone porous membrane, a polysulfone porous membrane, a polyvinylidene fluoride (PVDF) porous membrane, a polyacrylonitrile nanofiber membrane, a PVDF nanofiber membrane, a cellulose ester nanofiber membrane, a polyvinyl acetate or alcohol nanofiber membrane, or a polyvinyl butyral nanofiber membrane, or a combination thereof.

19. The system of claim 9, wherein the filter includes at least one of
a membrane formed by a thermally induced phase separation (TIPS) process, and
a nanofiber membrane.

20. The system of claim 9, wherein the filter includes multiple zones of porosity, and wherein the first side of the filter comprises the smallest pore zone.

21. A system for detecting an analyte of interest in a sample, the system comprising:
a first container comprising a filter portion, the filter portion comprising a filter, the filter having a first side and comprising a filtrand of the sample on the first side;
a second container comprising the filter portion coupled to a detection portion, the detection portion comprising a microstructured surface, the filter portion and the detection portion being coupled together such that the first side of the filter portion faces the microstructured surface of the detection portion, the microstructured surface of the detection portion adapted to receive a concentrate of the sample when the second container is exposed to a centrifugal force, the microstructured surface of the detection portion further adapted to retain at least a portion of the concentrate of the sample under normal gravitational forces, the microstructured surface comprising a plurality of recesses, wherein each of the plurality of recesses contains a volume of no greater than 1 microliter.

\* \* \* \* \*